US007563583B2

(12) United States Patent
Ballinger et al.

(10) Patent No.: US 7,563,583 B2
(45) Date of Patent: Jul. 21, 2009

(54) HEREGULIN VARIANTS

(75) Inventors: Marcus D Ballinger, Burlingame, CA (US); Jennifer T Jones, San Leandro, CA (US); Wayne J Fairbrother, Burlingame, CA (US); Mark S Sliwkowski, San Carlos, CA (US); James A Wells, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 465 days.

(21) Appl. No.: 11/347,808

(22) Filed: Feb. 2, 2006

(65) Prior Publication Data
US 2006/0183194 A1 Aug. 17, 2006

Related U.S. Application Data

(60) Division of application No. 10/082,747, filed on Feb. 22, 2002, which is a continuation of application No. 09/101,544, filed as application No. PCT/US98/01579 on Feb. 10, 1998, now Pat. No. 6,387,638, which is a continuation-in-part of application No. 08/799,054, filed on Feb. 10, 1997, now abandoned.

(51) Int. Cl.
G01N 33/53 (2006.01)
G01N 33/567 (2006.01)
A61K 38/00 (2006.01)

(52) U.S. Cl. .................. 435/7.1; 435/7.2; 435/7.21; 435/377; 514/12

(58) Field of Classification Search .................. None
See application file for complete search history.

(56) References Cited

U.S. PATENT DOCUMENTS

| 4,968,603 A | 11/1990 | Slamon et al. ............... 435/6 |
| 5,183,884 A | 2/1993 | Kraus et al. ............... 536/23.5 |
| 5,367,060 A | 11/1994 | Vandlen et al. ............. 530/399 |
| 6,033,660 A * | 3/2000 | Mather et al. .............. 424/93.7 |

FOREIGN PATENT DOCUMENTS

| EP | 444961 A1 | 9/1991 |
| EP | 505148 | 9/1992 |
| EP | 599274 | 6/1994 |
| WO | WO 92/18627 | 10/1992 |
| WO | WO 92/20798 | 11/1992 |
| WO | WO 93/22424 | 11/1993 |
| WO | WO 94/00140 | 1/1994 |
| WO | WO 94/04560 | 3/1994 |
| WO | WO 94/08007 | 4/1994 |
| WO | WO 94/26298 | 11/1994 |
| WO | WO 94/28133 | 12/1994 |
| WO | WO 95/32724 | 12/1995 |
| WO | WO 96/31599 | 10/1996 |
| WO | WO 96/36720 | 11/1996 |

OTHER PUBLICATIONS

Ayala et al., " Multiple Alleles," *Modern Genetics*, Benjamin/Cummings Pub. Co., Menlo Park, CA, 45-48 (1980).
Barbacci et al., "The structural basis for the specificity of epidermal growth factor and heregulin binding," *Journal of Biological Chemistry* (published erratum appears in *J. Biol. Chem.* Nov. 24, 1995; 270(47):28494) 270(16):9585-9589 (Apr. 21, 1995).
Bass, et al., "Hormone Phage: An Enrichment Method for Variant Proteins with Altered Binding Properties," *Proteins: Structure, Function, and Genetics* 8(4):309-314 (1990).
Brockes, "Assay and isolation of glial growth factor from the bovine pituitary," *Methods in Enzymology* 147:217-225 (1987).
Brockes et al., "Glial growth factor-like activity in Schwann Cell tumors," *Annals of Neurology* 20:3:317-322 (1986).
Brockes et al., "Purification and preliminary characterization of a glial growth factor from the bovine pituitary," *Journal of Biological Chemistry* 255(18):8374-8377 (1980).
Burden et al., "Neuregulins and their receptors: a versatile signaling module in organogenesis and oncogenesis," *Neuron* 18(6):847-855 (Jun. 1997).
Burgess et al., "Biosynthetic processing of neu differentiation factor. Glycosylation, trafficking, and regulated cleavage from the cell surface," *Journal of Biological Chemistry* 270(32):19188-19196 (1995).
Callard, et al., *The Cytokine Factsbook*, Academic Press, London, p. 31 (1994).
Carraway et al., "The erbB3 gene product is a receptor for heregulin," *Journal of Biological Chemistry* 269(19):14303-14306 (1994).
Carraway, et al., "Neuregulin-2, a new ligand of ErbB3/ErbB4-receptor tyrosine kinases," *Nature* 387:512-516 (1997).
Chang, et al., "Ligands for ErbB-family receptors encoded by a neuregulin-like gene," *Nature* 387:509-512 (1997).
Chau, B. N. et al., "The EGF Receptor Binding of Recombinant Heregulinβ1/EGF Hybrids is Blocked by Heregulin Residue Glutamate 195," *Biochemical & Biophysical Research Communications* 229:882-886 (1996).
Chu et al., "Regulation of the acetylcholine receptor & subunit gene by recombinant ARIA: an in vitro model for transynaptic gene regulation," *Neuron* 14(2):329-339 (Feb. 1995).
Corfas & Fischbach, "The number of Na$^+$ channels in cultured chick muscle is increased by ARIA, an in vitro model for acetylcholine receptor-inducing activity," *J. Neuroscience* 13(5):2118-2125 (1993).
Cunningham et al., "High Resolution Epitope Mapping of hGH-Receptor Interactions by Alanine-Scanning Mutagenesis," *Science* 244:1081-1085 (Jun. 1989).

(Continued)

*Primary Examiner*—David S Romeo
*Assistant Examiner*—Daniel C Gamett
(74) *Attorney, Agent, or Firm*—Weaver Austin Villeneuve & Sampson LLP; Emily M. Haliday

(57) ABSTRACT

The present invention provides heregulin variants that are capable of binding an ErbB receptor. Included in the invention are variants of human heregulins, and, in particular, variants of human heregulin-β1 having enhanced affinity for the ErbB-3 and ErbB-4 receptors. These variants include at least one amino acid substitution and can include further modifications. The invention also provides nucleic acid molecules encoding heregulin variants and related vectors, host cells, pharmaceutical compositions, and methods.

15 Claims, 4 Drawing Sheets

OTHER PUBLICATIONS

Cunningham et al., "Production of an Atrial Natriuretic Peptide Variant that is Specific for Type A Receptor," *EMBO Journal* 13(11):2508-2515 (1994).

Cwirla et al., "Peptides on phage: a vast library of peptides for identifying ligands," *Proc. Natl. Acad. Sci. USA* 87(16):6378-6382 (1990).

Danilenko et al., "Neu differentiation factor (NDF) accelerates epidermal migration and differentiation in excisional wounds," *FASEB* 8:4-5: abstract No. 3101, p. A535 (1994).

Falls et al., "ARIA, a Protein That Stimulates Acetylcholine Receptor Synthesis, is a Member of the Neu Ligand Family," *Cell* 72:801-815 (1993).

Friess et al., "Enhanced erbB-3 Expression in Human Pancreatic Cancer Correlates With Tumor Progression," *Clinical Cancer Research* 1:1413-1420 (1995).

Gorman et al., "Transient Production of Proteins Using an Adenovirus Transformed Cell Line," *DNA Prot. Eng. Tech.* 2(1):3-10 (1990).

Ho, W., et al., "Sensory and Motor Neuron-derived Factor," *Journal of Biological Chemistry* 270(24):14523-14532 (1995).

Holmes et al., Identification of heregulin, a specific activator of $p185^{erbB2}$ *Science* 256:1205-1210 (1992).

Jacobsen et al., "High-Resolution Solution Structure of the EGF-like Domain of Heregulin-α" *Biochemistry* 35(11):3402-3417 (1996).

King et al., "Ligand-independent tyrosine phosphorylation of EGF receptor and the erbB-2/neu proto-oncogene product is induced by hyperosmotic shock" *Oncogene* 4(1):13-18 (1989).

Kokai et al., "Synergistic Interaction of p185c-neu and the EGF Receptor Leads to Transformation of Rodent Fibroblasts," *Cell* 58:287-292 (1989).

Kraus et al., "Demonstration of ligand-dependent signaling by the erbB-3 tyrosine kinase and its constitutive activation in human breast tumor cells," *Proc. Natl. Acad. Sci.* 90:2900-2904 (1993).

Kraus et al., "Isolation and characterization of ERBB3, a third member of the ERBB/epidermal growth factor receptor family: Evidence for overexpression in a subset of human mammary tumors," *Proc. Natl. Acad. Sci. USA* 86:9193-9197 (1989).

Kunkel et al., "Rapid and Efficient Site-Specific Mutagenesis Without Phenotypic Selection," *Methods in Enzymology* 154:367-382 (1987).

Lee et al., "Assignment of Heregulin (HGL) to Human Chromosome 8p22-p11 by PCR Analysis of Somatic Cell Hybrid DNA," *Genomics* 16:790-791 (1993).

Lemke & Brockes, "Identification and purification of glial growth factor," *J. Neurosci.* 4(1):75-83 (1984).

Lemoine et al., "The erbB-3 gene in human pancreatic cancer," *J. Pathol.* 168:269-273 (1992).

Lemoine et al., "Expression of the ERBB3 gene product in breast cancer," *Br. J. Cancer* 66:1116-1121 (1992).

Levi et al., "The Functional Characteristics of Schwann Cells Cultured from Human Peripheral Nerve after Transplantation into a Gap within the Rat Schiatic Nerve," *J. Neuroscience* 14(3):1309-1319 (1994).

Lewis et al., "Growth Regulation of Human Breast and Ovarian Tumor Cells by Heregulin: Evidence for the Requirement of ErbB2 as a Critical Component in Mediating Heregulin Responsiveness," *Cancer Research* 56:1457-1465 (1996).

Li et al., "Identification of Gas6 as a Growth Factor for Human Schwann Cells," *Journal of Neuroscience* 16(6):2012-2019 (1996).

Lowman et al., "Selecting High-Affinity Binding Proteins by Monovalent Phage Display," *Biochemistry* 30:10832-10838 (1991).

Lu et al., "Post-translational processing of Membrane-associated *neu* Differentiation Factor Proisoforms Expressed in Mammalian Cells," *Journal of Biological Chemistry* 270(9):4775-4783 (1995).

Marchionni et al., "Glial growth factors are alternatively spliced erbB2 ligands expressed in the nervous system," *Nature* 362:312-318 (1993).

Meyer & Birchmeier, "Distinct isoforms of neuregulin are expressed in mesenchymal and neuronal cells during mouse development," *Proc. Natl. Acad. Sci.* 91:1064-1068 (1994).

Nagata et al., "Solution structure of the epidermal growth factor-like domain of heregulin-α, a ligand for $p180^{erbB-4}$" *EMBO J.* 13(15):3517-3523 (1994).

Parmley et al., "Antibody-selectable filamentous fd phage vectors: affinity purification of target genes," *Gene* 73:305-318 (1988).

Peles et al., "Cell-type specific interaction of Neu differentiation factor (NDF/heregulin) with Neu/HER-2 suggests complex ligand-receptor relationships," *EMBO Journal* 12(3):961-971 (1993).

Peles et al., "Isolation of the Neu/HER-2 Stimulatory Ligand: a 44 Kd Glycoprotein That Induces Differentiation of Mammary Tumor Cells," *Cell* 69(1):205-216 (1992).

Pinkas-Kramarski et al., "Brain neurons and glial cells express Neu differentiation factor/heregulin: A survival factor for astrocytes," *Proc. Natl. Acad. Sci. USA* 91:9387-9391 (1994).

Plowman et al., "Heregulin induces tyrosine phosphorylation of HER4/$p180^{erbB4}$" *Nature* (Letters to Nature) 366:473-475 (Dec. 2, 1993).

Plowman et al., "Ligand-specific activation of HER4/$p180^{erbB4}$, a fourth member of the epidermal growth factor receptor family," *Proc. Natl. Acad. Sci. USA* 90:1746-1750 (1993).

Poller et al., "Production and characterization of a polyclonal antibody to the c-erbB-3 protein: examination of c-erbB-3 protein expression in adenocarcinomas," *J. Pathol.* 168(3):275-280 (1992).

Puddicombe et al., "The Significance of Valine 33 as a Ligand-specific Epitope of Transforming Growth Factor α" *Journal of Biological Chemistry* 271(26):15367-15372 (1996).

Rajkumar et al., "Expression of the c-erbB-3 protein in gastrointestinal tract tumors determined by monoclonal antibody RTJ1," Published erratum appears in *J. Pathol.* 171(2):154 (1993).

Sadick et al., "Analysis of Heregulin-induced ErbB2 Phosphorylation with a High-Throughput Kinase Receptor Activation Enzyme-Linked Immunosorbant Assay," *Analytical Biochemistry* 235:207-214 (1996).

Sambrook et al., "Small-scale Preparations of Single-stranded Bacteriophage M13 DNA," *Molecular Cloning: A Laboratory Manual*, 2nd ed., New York: Cold Spring Harbor Laboratory Press, 1:4.29-4.30 (1989).

Sanger et al., "DNA Sequencing with Chain-terminating Inhibitors," *Proc. Natl. Acad. Sci. USA* 74(12):5463-5467 (1977).

Sanidas et al., "Expression of the c-erbB-3 gene product in gastric cancer," *Int. J. Cancer* 54:935-940 (1993).

Scott et al., "Searching for Peptide Ligands with an Epitope Library," *Science* 249:386-390 (1990).

Sklar et al., "A Novel Growth Factor for Muscle-rhGGF2," *J. Cell Biochem.* (abstract No.-W462) p. 540 (1994).

Slamon et al., "Human Breast Cancer: Correlation of Relapse and Survival with Amplification of the HER-2/*neu* Oncogene," *Science* 235:177-182 (1987).

Slamon et al., "Studies of the HER-2/*neu* Proto-oncogene in Human Breast and Ovarian Cancer," *Science* 244:707-712 (1989).

Sliwkowski et al., "Coexpression of erbB2 and erbB3 Proteins Reconstitutes a High Affinity Receptor for Heregulin," *Journal of Biological Chemistry* 269(20):14661-14665 (1994).

Smith, "Filamentous Fusion Phage: Novel Expression Vectors That Display Cloned Antigens on the Virion Surface," *Science* 228 (4705):1315-1317 (1985).

Souriau et al., "A simple luciferase assay for signal transduction activity detection of epidermal growth factor displayed on phage," *Nucleic Acids Research* 25(8):1585-1590 (1997).

Stern et al., "EGF-stimulated tyrosine phosphorylation of $p185^{neu}$: a potential model for receptor interactions," *EMBO Journal* 7(4):995-1001 (1988).

Tzahar, E., et al., "Bivalence of of EGF-like ligands drives the ErbB signalling network," *EMBO Journal* 16(16):4938-4950 (1997).

Wada et al., "Intermolecular Association of the $p185^{neu}$ Protein and EGF Receptor Modulates EGF Receptor Function," *Cell* 61:1339-1347 (1990).

Wen et al., "Neu Differentiation Factor: A Transmembrane Glycoprotein Containing an EGF Domain and an Immunoglobulin Homology Unit," *Cell* 69(3):559-572 (1992).

Wen et al., "Structural and Functional Aspects of the Multiplicity of Neu Differentiation Factors," *Molecular & Cellular Biology* 14(3):1909-1919 (1994).

Zhang et al., "Neuregulin-3 (NRG3): A novel neural tissue-enriched protein that binds and activates ErbB4," *Proc. Natl. Acad. Sci. USA* 94:9562-9567 (1997).

Zrihan-Licht et al., "Association of Csk-homologous Kinase (CHK) (formerly MATK) with HER-2/ErbB-2 in Breast Cancer Cells," *Journal of Biological Chemistry* 272(3):1856-1863 (1997).

Barbacci et al., "The structural basis for the specificity of epidermal growth factor and heregulin binding", *Journal of Biological Chemistry*; 270(16):9585-9589 (Apr. 21, 1995).

Lowman et al., "Selecting High-Affinity Binding Proteins by Monovalent Phage Display", *Biochemistry*, 30:10832-10838 (1991).

* cited by examiner

```
beta1:  177  SHLVRCAEKEKTFCVNGGECFMVKDLSNPSRYLCKCKPGFTGDRCQNYVMASFYKHLGIEFMEAEELYQKR   SEQ ID NO: 1
alpha:  177  SHLVRCAEKEKTFCVNGGECFMVKDLSNPSRYLCKCQPGFTGARCTENVPMKVQNQEK------AEELYQKR  SEQ ID NO: 2
beta2:  177  SHLVKCAEKEKTFCVNGGECFMVKDLSNPSRYLCKCPNEFTGDRCQNYVMASFYK-------AEELYQKR    SEQ ID NO: 3
beta3:  177  SHLVRCAEKEKTFCVNGGECFMVKDLSNPSRYLCKCPNEFTGDRCQNYVMASFYKHLGIEFMEAEELYQKR   SEQ ID NO: 4
ndfa2:  177  SHLIRCAEKEKTFCVNGGECFTVKDLSNPSRYLCKCQPGFTGARCTENVPMKVQTQEK-----AEELYQKR   SEQ ID NO: 5
ndfb1:  177  SHLIRCAEKEKTFCVNGGECFMVKDLSNPSRYLCKCPNEFTGDRCQNYVMASFYKHLGIEFMEAEELYQKR   SEQ ID NO: 6
ndfb2:  177  SHLIRCAEKEKTFCVNGGSCFTVKDLSNPSRYLCKCPNEFTGDRCQNYVMASFYK-------AEELYQKR    SEQ ID NO: 7
ndfb3:  177  SHLIKCAEKEKTFCVNGGECFTVKDLSNPSRYLCKCQPGFTGARCTENVPMFYSTSTPFLSLPE          SEQ ID NO: 8
ndfb4:  177  SHLVKCAEKEKTFCVNGGECFTVKDLSNPSRYLCKCQPGFTGARCTENVPMFYSMTSRRKRQETEKPLERKLFASLVKESK SEQ ID NO: 9
ggf  :  358  SHLVKCAEKEKTFCVNGGECFMVKDLSNPSRYLCKCPNEFTGDRCQNYVMASFYSTSTPFLSLPE         SEQ ID NO: 10
smdf :  232  SHLVRCAEKEKTFCVNGGECFMVKDLSNPSRYLCKCPNEFTGDRCQNYVMASFYSTSTPFLSLPE         SEQ ID NO: 11
gamma:  704  SHLVKCAEKEKTFCVNGGECYMVKDLSNPSRYLCKCPNEFTGDRCQNYVMASFYSTSTPFLSLPE         SEQ ID NO: 12
aria :  136  SHLTKCDIKQAFCVNGGECYLPNPPRYLCKCPNEFTGDRCQNYVMASFYKHLGIEFMEAEELYQKR        SEQ ID NO: 13
                                                               ###  #  ###  #
```

FIG. 1

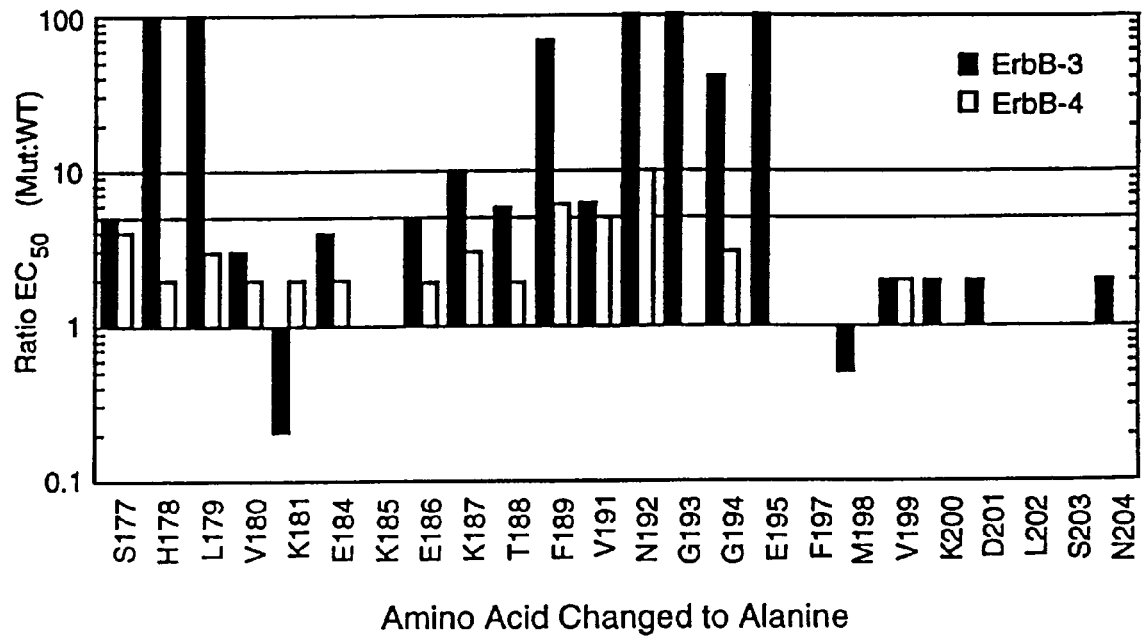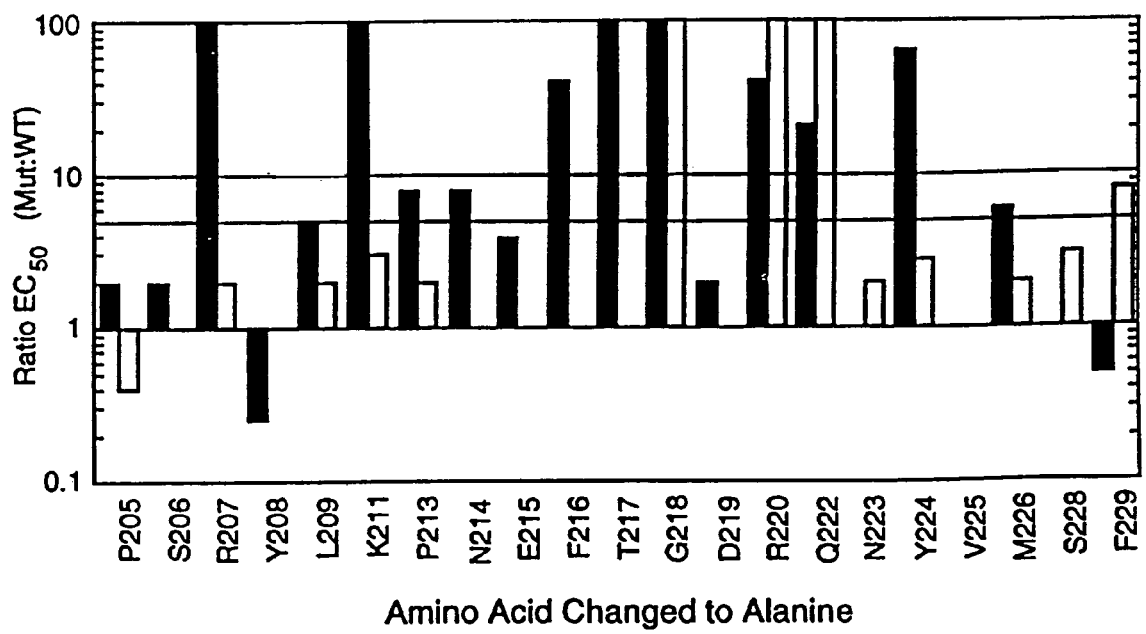
FIG. 2

|        | 177 180 |       |         | 190   |       |     | 200   |         | 210 |        |       | 220  |   | 228 |              |
|        | SHLVK   | C     | AEKEKT  | FC    | VNGGE | C   | FMVKD | LSNPSRYL | C   | KCPNEF | TGDR  | C    | QNYVM | AS | SEQ ID NO: 92 |
| HRG8   |         |       |         |       |       |     |       |          |     |        |       |      |       |    |              |
| HRG63  |         |       |         |       |       |     |       |          |     |        |       |      |       | R  | SEQ ID NO: 14 |
| EGF    | NSDSE   |       | PLSHDG  | Y.    | LHD.V |     | MYIEA | ---LDK.A |     | N.VVGY | I.E.  |      | YRDL  |    | SEQ ID NO: 15 |
|        | -1-     |       | -10-    |       |       |     | -20-  | -30-     |     |        | -40-  |      | -48-  |    |              |
| HRG 90 |         |       |         |       |       |     |       |          |     |        |       |      | I     |    | SEQ ID NO: 16 |
| HRG 37 | WE..P   |       | GWDREG  |       |       |     | YK.RI | ---YGYLM |     |        |       |      | I     |    | SEQ ID NO: 17 |
| HRG 38 | WE..P   |       | GWDREG  |       |       |     | YK.RI | ---YGYLM |     |        |       |      | I     |    | SEQ ID NO: 18 |
| HRG 40 | WE..P   |       | GWDREG  |       |       |     | YK.RI | ---YGYLM |     |        |       |      | I     |    | SEQ ID NO: 19 |
| HRG 41 | WE..P   |       |         |       |       |     | YK.RI | ---YRYRM |     |        |       |      | I     |    | SEQ ID NO: 20 |
| HRG 48 |         |       | G.EREG  |       |       |     | YR.KT | ---YGYLM |     |        |       |      | I     |    | SEQ ID NO: 21 |
| HRG 53 |         |       | G.EREG  |       |       |     |       | ---YGYLM |     |        |       |      |       |    | SEQ ID NO: 22 |
| HRG 54 |         |       | G.EREG  |       |       |     |       | ---YGYLM |     |        |       |      |       |    | SEQ ID NO: 23 |
| HRG 55 |         |       | G.EREG  |       |       |     |       | ---YGYLM |     |        |       |      |       |    | SEQ ID NO: 24 |
| HRG 56 |         |       |         |       |       |     | YR.KT | ---YGYLM |     |        |       |      | I     |    | SEQ ID NO: 25 |
| HRG 57 |         |       |         |       |       |     | YR.KT | ---YGYLM |     |        |       |      | I     |    | SEQ ID NO: 26 |
| HRG 58 |         |       |         |       |       |     | YR.KT | ---YGYLM |     |        |       |      | I     |    | SEQ ID NO: 27 |
| HRG 59 |         |       |         |       |       |     | YR.KT |          |     |        |       |      | I     |    | SEQ ID NO: 28 |
| HRG 60 |         |       | G.EREG  |       |       |     | YR.KT | ---YGYLM |     |        |       |      | I     |    | SEQ ID NO: 29 |
| HRG 61 |         |       | G.EREG  |       |       |     | YR.KT | ---YGYLM |     |        |       |      | I     |    | SEQ ID NO: 30 |
| HRG 62 |         |       | G.EREG  |       |       |     | YR.KT | ---YGYLM |     |        |       |      | I     |    | SEQ ID NO: 31 |
| HRG 71 |         |       |         |       |       |     | YR.KT | ---YGYLM |     |        |       |      | H..I  |    | SEQ ID NO: 32 |
| HRG 73 |         |       | G.EREG  |       |       |     | YR.KT | ---YGYLM |     |        |       |      | H..I  |    | SEQ ID NO: 33 |

FIG. 4

HEREGULIN VARIANTS

CROSS-REFERENCE TO RELATED APPLICATIONS

This application is a Divisional of U.S. Ser. No. 10/082,747, Filed Feb. 22, 2002, which is a Continuation of U.S. Ser. No. 09/101,544, Filed Jul. 17, 1998, which is a 371 of PCT/US98/01579, Filed Feb. 10, 1998, which is a CIP of Ser. No. 08/799,054, Filed Feb. 10, 1997, which are hereby incorporated by reference in their entireties.

GOVERNMENT LICENSE RIGHTS STATEMENT

The U.S. Government has a paid-up license in this invention and the right in limited circumstances to require the patent owner to license others on reasonable terms, as provided for by the terms of Grant No. GM16549-01 awarded by the National Institutes of Health.

BACKGROUND OF THE INVENTION

1. Field of the Invention

The present invention relates to heregulin variants, nucleic acid molecules encoding such variants, and related vectors, host cells, pharmaceutical compositions, and methods. In particular, the invention relates to amino acid substitution variants of human heregulin-β1 having an enhanced affinity for the ErbB-3 and ErbB-4 receptors.

2. Description of the Related Art

Transduction of signals that regulate cell growth and differentiation is regulated in part by phosphorylation of various cellular proteins. Protein tyrosine kinases are enzymes that catalyze this process. Receptor protein tyrosine kinases are believed to direct cellular growth via ligand-stimulated tyrosine phosphorylation of intracellular proteins. Growth factor receptor protein tyrosine kinases of the class I subfamily include the 170 kilodalton (kDa) epidermal growth factor receptor (EGFR) encoded by the erbB1 gene. erbB1 has been causally implicated in human malignancy. In particular, increased expression of this gene has been observed in more aggressive carcinomas of the breast, bladder, lung, and stomach.

The second member of the class I subfamily, p185$^{neu}$ (also called the ErbB-2 receptor or p185$^{HER2}$), was originally identified as the product of the transforming gene from neuroblastomas of chemically treated rats. The neu (erbB2 or HER2) gene encodes a 185 kDa receptor protein tyrosine kinase.

Amplification and/or overexpression of the human erbB2 gene correlates with a poor prognosis in breast and ovarian cancers. Slamon et al., Science 235:177-82 (1987); Slamon et al., Science 244:707-12 (1989). Overexpression of erbB2 has been correlated with other carcinomas including carcinomas of the stomach, endometrium, salivary gland, lung, kidney, colon and bladder. Accordingly, in U.S. Pat. No. 4,968,603, Slamon et al. describe and claim various diagnostic assays for determining erbB2 gene amplification or expression in tumor cells. Slamon et al. discovered that the presence of multiple copies of the erbB2 oncogene in tumor cells indicates that the disease is more likely to spread beyond the primary tumor site, and that the disease may therefore require more aggressive treatment than might otherwise be indicated by other diagnostic factors. Slamon et al. conclude that the erbB2 gene amplification test, together with the determination of lymph node status, provides greatly improved prognostic utility.

A further related gene, called erbB3 (or HER3), which encodes the ErbB-3 receptor (p180$^{HER3}$) has also been described. See U.S. Pat. No. 5,183,884; Kraus et al., PNAS USA 86:9193-97 (1989); EP Patent Application No. 444,961A1; Kraus et al., PNAS USA 90:2900-04 (1993). Kraus et al. (1989) discovered that markedly elevated levels of erbB3 mRNA were present in certain human mammary tumor cell lines indicating that erbB3, like erbB1 and erbB2, may play a role in human malignancies. Also, Kraus et al. (1993) showed that EGF-dependent activation of the ErbB-3 catalytic domain of a chimeric EGFR/ErbB-3 receptor resulted in a proliferative response in transfected NIH-3T3 cells. Furthermore, these researchers demonstrated that some human mammary tumor cell lines display a significant elevation of steady-state ErbB-3 receptor tyrosine phosphorylation, further implicating this receptor in human malignancies. The role of erbB3 in cancer has been explored by others, and this gene has been found to be overexpressed in breast (Lemoine et al., Br. J. Cancer 66:1116-21 [1992]), gastrointestinal (Poller et al., J. Pathol. 168:275-80 [1992]; Rajkumer et al., J. Pathol. 170:371-78 [1993]; Sanidas et al., Int. J. Cancer 54:935-40 [1993]), and pancreatic cancers (Lemoine et al., J. Pathol. 168:269-73 [1992], and Friess et al., Clinical Cancer Research 1:1413-20 [1995]).

The class I subfamily of growth factor receptor protein tyrosine kinases has been further extended to include the ErbB-4 (HER4) receptor, which is the product of the erbB4 (HER4) gene. See EP Patent Application No. 599,274; Plowman et al., PNAS USA 90:1746-50 (1993); and Plowman et al., Nature 366:473-75 (1993). Plowman et al. found that increased erbB4 expression closely correlated with certain carcinomas of epithelial origin, including breast adenocarcinomas. Diagnostic methods for detection of human neoplastic conditions (especially breast cancers) that evaluate erbB4 expression are described in EP Patent Application No. 599,274.

The quest for the activator of the erbB2 oncogene has lead to the discovery of a family of heregulin polypeptides. In humans, the heregulin polypeptides characterized thus far are derived from alternate splicing of a single gene which was mapped to the short arm of chromosome 8 by Lee and Wood, Genomics 16:790-91 (1993).

Holmes et al. isolated and cloned a family of polypeptide activators for the ErbB-2 receptor which they called heregulin-α (HRG-α), heregulin-β1 (HRG-β1), heregulin-β2 (HRG-β2), and heregulin-β3 (HRG-β3). See Holmes et al., Science 256:1205-10 (1992); WO 92/20798; and U.S. Pat. No. 5,367,060. These researchers demonstrated the ability of the purified heregulin polypeptides to activate tyrosine phosphorylation of the ErbB-2 receptor in MCF7 breast tumor cells. Furthermore, the mitogenic activity of the heregulin polypeptides on SK-ER-3 cells (which express high levels of the ErbB-2 receptor) was also demonstrated.

Heregulins are large multi-domain proteins that are typically expressed as "pro-heregulins." Pro-heregulins have been shown to undergo proteolytic processing to a mature soluble form (usually of about 44-45 kDa). Processing has been shown to occur intracellularly or at the cell surface. Domains in the soluble form include (in order from the N- to the C-terminus) an immunoglobulin homology (Ig-like) domain, a spacer region rich in glycosylation sites, and a domain similar to a domain found in EGF that is sufficient for ErbB receptor binding and activation. See Barbacci, et al., J. Biol. Chem. 270:9585-89 (1995).

The heregulin EGF-like domains are characterized by substantial structural similarities to (Jacobsen et al., Biochemistry 35:3402-17 [1996]), and limited sequence homology with, EGF residues 1-48 (Holmes, et al., supra). Functional similarities between the heregulin EGF-like domains and EGF have been established by data showing that blocks of EGF sequence substituted into heregulin-β1 do not impair binding to cells co-expressing ErbB-3 and ErbB-2. Barbacci et al., supra.

While heregulins are substantially identical in the first 213 amino acid residues, they are classified into two major types, α and β, based on two EGF-like domains that differ in their C-terminal portions. For example, the heregulin-α EGF-like domain differs from that of the β1-isoform by nine substitutions near the C-terminus. The β-isoform has been reported to bind ErbB receptors with approximately eight to 10-fold higher affinity than the α-isoform. Wen et al., *Mol. Cell. Biol.* 14:1909-19 (1994).

The solution structure of the heregulin-α EGF domain has recently been determined at high resolution by NMR: Jacobsen et al., supra; Nagata et al., *EMBO J.* 10, 3517-3523 (1994). The salient features of this domain include (1) an N-terminal subdomain containing a central three-stranded β-sheet with an intermittent helix and (2) a smaller C-terminal subdomain that contains a short stretch of β-sheet. The EGF domain is stabilized by three disulfide bonds, two in the N-terminal subdomain and one the C-terminal subdomain. The pairing of the six corresponding cysteine residues is conserved in EGF-like domains from all heregulins and from EGF.

The 44 kDa neu differentiation factor (NDF), which is the rat equivalent of human HRG, was first described by Peles et al., *Cell,* 69:205-16 (1992), and Wen et al., *Cell,* 69:559-72 (1992). Like the human heregulin polypeptides, NDF has an Ig-like domain followed by an EGF-like domain and lacks a N-terminal signal peptide. Subsequently, Wen et al. carried out "exhaustive cloning" to extend the family of NDFs. Wen et al., *Mol. Cell. Biol.,* 14:1909-19 (1994). This work revealed six distinct fibroblastic pro-NDFs. Adopting the nomenclature of Holmes et al., the NDFs were classified as either α or β polypeptides based on the sequences of the EGF-like domains. Isoforms 1 to 4 are characterized on the basis of a variable region between the EGF-like domain and transmembrane domain. Also, isoforms a, b and c are defined based on variable-length cytoplasmic domains. These researchers conclude that different NDF isoforms are generated by alternative splicing and perform distinct tissue-specific functions. See also EP 505 148; WO 93/22424; and WO 94/28133 (discussing NDF).

Falls et al., *Cell* 72:801-815 (1993) describe another member of the heregulin family which they call "acetylcholine receptor inducing activity (ARIA) polypeptide." The chicken-derived ARIA polypeptide stimulates synthesis of muscle acetylcholine receptors. See WO 94/08007. ARIA is a β-type heregulin and lacks the entire spacer region between the Ig-like domain and EGF-like domain of HRG-α and HRGβ1-β3.

Marchionni et al., *Nature* 362:312-318 (1993) identified several bovine-derived proteins that they call "glial growth factors (GGFs)." These GGFs share the Ig-like domain and EGF-like domain with the other heregulin proteins described above, but also have an amino-terminal kringle domain. GGFs generally do not have the complete spacer region between the Ig-like domain and EGF-like domain. Only one of the GGFs, GGFII, has an N-terminal signal peptide. See also WO 92/18627; WO 94/00140; WO 94/04560; WO 94/26298; WO 95/32724 (describing GGFs and uses thereof).

Ho et al. describe another member of the heregulin family called "sensory and motor neuron-derived factor (SMDF)." Ho et al., *J. Biol. Chem.* 270:14523-32 (1995). This protein has an EGF-like domain characteristic of all other heregulin polypeptides but a distinct N-terminal domain. In addition, SMDF lacks both the Ig-like domain and the spacer region found in other heregulin polypeptides. Another feature of SMDF is the presence of two stretches of hydrophobic amino acids near the N-terminus.

While the heregulin polypeptides were first identified based on their ability to activate the ErbB-2 receptor (see Holmes et al., supra), it has been discovered that certain ovarian cells expressing neu (erbB2) and neu-transfected fibroblasts did not bind or crosslink to NDF, nor did they undergo tyrosine phosphorylation in response to NDF. Peles et al., *EMBO J.* 12:961-71 (1993). This finding indicated that another cellular component was necessary for conferring full heregulin responsiveness.

Carraway et al. subsequently demonstrated that $^{125}$I-rHRG-β1 177-244 bound to NIH-3T3 fibroblasts stably transfected with bovine erbB3 but not to non-transfected parental cells. These researchers also expressed bovine ErbB-3 receptor in insect cells and showed that HRG-β1 177-244 bound to a preparation of ErbB-3 receptor solubilized from these cells. They concluded that ErbB-3 is a receptor for heregulin and mediates phosphorylation of intrinsic tyrosine residues as well as phosphorylation of ErbB-2 receptor in cells that express both receptors. Carraway et al., *J. Biol. Chem.* 269:14303-05 (1994). Sliwkowski et al. found that cells transfected with erbB3 alone show low affinities for heregulin, whereas cells transfected with both erbB2 and erbB3 show higher affinities. Sliwkowski et al., *J. Biol. Chem.* 269: 14661-65 (1994).

Plowman and his colleagues have similarly studied ErbB-4/ErbB-2 receptor activation. They expressed the ErbB2 receptor alone, the ErbB4 receptor alone, or the two receptors together in human T lymphocytes and demonstrated that heregulin is capable of stimulating tyrosine phosphorylation of ErbB-4, but could only stimulate ErbB-2 phosphorylation in cells expressing both receptors. Plowman et al., *Nature* 336:473-75 (1993).

These observations are consistent with the "receptor cross-talking" concept described previously by Kokai et al., *Cell* 58:287-92 (1989), Stern et al., *EMBO J.* 7:995-1001 (1988), and King et al., 4:13-18 (1989). These researchers found that binding of EGF to the EGFR resulted in activation of the EGFR kinase domain and cross-phosphorylation of the ErbB-2 receptor. This is believed to be a result of ligand-induced receptor heterodimerization and the concomitant cross-phosphorylation of the receptors within the heterodimer. Wada et al., *Cell* 61:1339-47 (1990).

Thus, the ErbB receptors are believed to be activated by ligand-induced receptor dimerization. Specifically, heregulins can bind separately to ErbB-3 and ErbB-4 receptors, but not to the ErbB-2 receptor. However, ErbB-2 is required for signaling, and heterodimers containing ErbB-2 in combination with ErbB-3 or ErbB-4 bind heregulins with higher affinity than homodimers containing ErbB-3 or ErbB-4. Plowman et al., *Nature* 366:473-75 (1993); Sliwkowski et al., *J. Biol. Chem.* 269:14661-65 (1994).

The biological activities of heregulins have been investigated by several groups. For example, Holmes et al. (supra) found that heregulin exerts a mitogenic effect on mammary cell lines (such as SK-SR-3 and MCF-7). Lewis et al. reported that heregulin-β1 stimulated proliferation and enhanced colony formation in soft agar in a number of human breast and ovarian tumor cell lines. Lewis et al., *Cancer Research* 56:1457-65 (1996). These researchers also showed that ErbB-2 is a critical mediator of heregulin responsiveness.

Pinkas-Kramarski et al. found that NDF (rat heregulin) is expressed in neurons and glial cells in embryonic and adult rat brain and primary cultures of rat brain cells, and suggested that NDF may act as a survival and maturation factor for astrocytes. Pinkas-Kramarski et al., *PNAS USA* 91:9387-91 (1994). Danilenko et al. reported that the interaction of NDF and the ErbB-2 receptor is important in directing epidermal migration and differentiation during wound repair. Danilenko et al., Abstract 3101, *FASEB* 8 (4-5):A535 (1994).

Meyer and Birchmeier analyzed expression of mouse heregulin during embryogenesis and in the perinatal animal using in situ hybridization and RNase protection experiments. Meyer and Birchmeier, *PNAS USA* 91:1064-68 (1994). These authors conclude, based on expression of this molecule, that heregulin plays a role in vivo as a mesenchymal and neuronal factor. Their findings also indicated that heregulin functions in the development of epithelia.

Falls et al. (supra) found that chicken ARIA plays a role in myotube differentiation, namely affecting the synthesis and concentration of neurotransmitter receptors in the postsynaptic muscle cells of motor neurons. Corfas and Fischbach demonstrated that ARIA also increases the number of sodium channels in chick muscle. Corfas and Fischbach, *J. Neuroscience* 13:2118-25 (1993).

Bovine GGFs have been reported to be mitogenic for Schwann cells. See, e.g., Brockes et al., *J. Biol. Chem.* 255: 8374-77 (1980); Lemke and Brockes, *J. Neurosci.* 4:75-83 (1984); Brockes et al., *J. Neuroscience* 4:75-83 (1984); Brockes et al., *Ann. Neurol.* 20:317-22 (1986); Brockes, *Methods in Enzym.* 147:217-225 (1987); Marchionni et al., supra. Schwann cells provide myelin sheathing around the axons of myelinated neurons and thus play an important role in the development, function and regeneration of peripheral nerves. The implications of this role from a therapeutic standpoint have been addressed by Levi et al., *J. Neuroscience* 14:1309-19 (1994). Levi et al. discussed the potential for construction of a cellular prosthesis including Schwann cells that could be transplanted into areas of damaged spinal cord. Methods for culturing Schwann cells ex vivo have been described. See WO 94/00140; Li et al., *J. Neuroscience* 16:2012-19 (1996).

GGFII has been shown to be mitogenic for subconfluent quiescent human myoblasts, and differentiation of clonal human myoblasts in the continuous presence of GGFII results in greater numbers of myotubes after six days of differentiation. Sklar et al., *J. Cell Biochem.*, Abst. W462, 18D, 540 (1994); see also WO 94/26298.

The relationship between the structure and function of new proteins can be investigated using any of a variety of available mutational analysis techniques. Examples of such techniques include alanine scanning mutagenesis and phagemid display. Alanine scanning can be used to identify active residues (i.e., residues that have a significant effect on protein function) in a protein or protein domain. For example, Cunningham and Wells used alanine scanning to identify residues in human growth hormone that were important for binding its receptor. Cunningham and Wells, *Science* 244:1081-85 (1999). In alanine scanning, a gene encoding the protein or domain to be canned is inserted into an expression vector, and mutagenesis is carried out to generate a series of vectors that encode proteins or domains in which sequential residues are converted to alanine. The encoded proteins or domain are expressed from these vectors, and the activities of the alanine-substituted variants are then tested to identify those with altered activity. An alteration in activity indicates that the residue at the alanine-substituted position is an active residue.

Phagemid display was developed to allow the screening of a large number of variant polypeptides for a particular binding activity. Smith and Parmley demonstrated that foreign peptides can be "displayed" efficiently on the surface of filamentous phage by inserting short gene fragments into gene III of the fd phage. Smith, *Science* 228:1315-17 (1985); Parmley and Smith, *Gene* 73:305-18 (1985). The gene III coat protein is present in about five copies at one end of the phage particle. The modified phage were termed "fusion phage" because they displayed the foreign peptides fused to the gene III coat protein. As each fusion phage particle displayed approximately five copies of the fusion protein, this mode of phage display was termed "polyvalent display."

Scott et al. and Cwirla et al. showed that fusion phage libraries could be screened by sequential affinity selections known as "panning." Scott et al., *Science* 249:386-90 (1990); Cwirla et al., *PNAS USA* 87:6378-82 (1990). However, early efforts to select high affinity fusion phage failed, presumably due to the polyvalence of the phage particles. This problem was solved with the development of a "monovalent" phage display system in which the fusion protein is expressed at a low level from a phagemid and a helper phage provides a large excess of wild-type coat protein. Bass et al., *Proteins* 8:309-14 (1990); Lowman et al., *Biochem.* 30:10832-38 (1991). Monovalent phage display can be used to generate and screen a large number of variant polypeptides to isolate those that bind with high affinity to a target of interest.

SUMMARY OF THE INVENTION

The present invention provides a heregulin variant having an amino acid sequence not found in nature and the ability to bind an ErbB receptor. In one embodiment, the variant has an amino acid substitution at a selected residue corresponding to a residue of 645-amino acid native human heregulin-$\beta$1 selected from the group consisting of:

S177, H178, L179, V180, K181, E184, E186, K187, T188, V191, N192, G193, G194, E195, M198, V199, K200, D201, N204, P205, S206, R207, Y208, L209, K211, P213, N214, E215, T217, G218, D219, Q222, N223, Y224, S228, and F229.

In a variation of this embodiment, the amino acid substitution is not a replacement of the selected residue with an epidermal growth factor (EGF) residue corresponding to the selected residue.

The heregulin variant can be a variant of any member of the heregulin family from any species. In one embodiment, the heregulin variant is a variant of a human heregulin, such as, for example, human heregulin-$\beta$1. The invention provides a human heregulin-$\beta$1 variant including an amino acid substitution selected from the group consisting of:

S177W; H178S, E, R, or A; V180Q, I, or E; K181P or A; A183G; E184V, W, K, R, G, or N; K185E, S, Q, or G; E186R; K187E or A; T188Q; E195Q; F197Y; M198R or K; K200R; D201T or I; P205T or Y; S206K, H, G, P, or R; R207Y; Y208R or L; L209M or G; K211R; P213S, T, N, or K; N214I, K, S, or E; E216M; N223H or W; and M226I.

In a variation of this embodiment, the heregulin variant includes sets of amino acid substitutions selected from this group. Some heregulin variants of the invention having sets of amino acid substitutions exhibit at least a 50-fold increase in ErbB-3 receptor affinity, which is also accompanied by an increase in ErbB-4 receptor affinity.

The invention also includes a heregulin variant that has a greater specificity for the ErbB-4 receptor, relative to the ErbB-3 receptor, than the heregulin from which the heregulin variant is derived. In one embodiment, this heregulin variant has an amino acid substitution at a selected residue corresponding to a residue of 645-amino acid native human heregulin-β1 selected from the group consisting of H178, L179, and R207.

In another embodiment, a heregulin variant having a greater specificity for the ErbB-4 receptor, relative to the ErbB-3 receptor, has a deletion of amino acid residues corresponding to residues S228 to K231 of 645-amino acid native human heregulin-β1 and a substitution of a single methionine for the deleted residues.

In addition to including one or more of the mutations disclosed herein, the heregulin variant can have one or more other modifications, such as an amino acid substitution, an insertion of at least one amino acid, a deletion of at least one amino acid, or a chemical modification. For example, the invention provides a heregulin variant that is a fragment. In a variation of this embodiment, the fragment includes residues corresponding to a portion of human heregulin-β1 extending from about residue 175 to about residue 230 (i.e., the EGF-like domain). In a further variation of this embodiment, the fragment includes residues corresponding to a portion of human heregulin-β1 extending from about residue 175 to about residue 245.

One aspect of the invention is a method for producing such a modified heregulin variant. The modification(s) is selected so that the modified heregulin variant retains the ability to an ErbB receptor.

In addition to a heregulin variant, the invention provides a related nucleic acid molecule, vector, and host cell. The invention also provides a method of producing a heregulin variant in which a host cell containing an expression vector capable of expressing the heregulin variant is cultured under conditions that allow expression of the heregulin variant, and the heregulin variant then recovered from the culture.

Other aspects of the invention relate to various uses of a heregulin variant. For example, the invention provides a method for activating an ErbB receptor in which the heregulin variant is contacted with a cell that expresses an ErbB receptor. The heregulin variant can be contacted with cells in culture, for example, to promote ex vivo survival, proliferation, or differentiation of cells, such as glial, Schwann, or muscle cells.

Alternatively, the heregulin variant can be combined with a pharmaceutically acceptable carrier and used to treat one of a wide range of cancers as well as diseases and disorders affecting the nervous system, musculature, and epithelia. Thus, the present invention provides a pharmaceutical composition and a treatment method.

The invention also includes a method of determining whether a sample contains an ErbB receptor that binds a heregulin. In particular, a heregulin variant is contacted with a sample, and specific binding between the heregulin variant and a component of the sample is determined as an indication of the presence and/or amount of ErbB receptor(s) present in the sample.

BRIEF DESCRIPTION OF THE DRAWINGS

FIG. 1 shows an alignment between the amino acid sequences in the EGF-like domains of a number of heregulin polypeptides and the amino acid sequence of the human heregulin-β1 EGF-like domain ("beta1"). The aligned sequences are as follows: human heregulin-α (alpha), human heregulin-β2 and -β3 (beta2 and beta3), neu differentiation factors a2 and b1 to b4 (ndfa2 and ndfb1-4), glial growth factor II (ggf), sensory and motor neuron-derived factor (smdf), human heregulin-γ, and acetylcholine receptor inducing activity polypeptide (aria). The number shown for each sequence is the residue number of the first amino acid shown, as numbered from the N-terminus of the native polypeptide whose sequence is shown. "#" indicates the differences between the α- and β-type EGF-like domains.

FIG. 2 shows the results of an alanine scan of the heregulin-β1 EGF-like domain (heregulin-β1 residues 177-228). Individual amino acids in this domain were mutated to alanine and displayed monovalently on phage as gIII fusion proteins, as described in Example 2. The histogram shows the change in binding affinity of each alanine variant for ErbB-3 and ErbB-4 receptor-Ig fusions (ErbB-3-Ig and ErbB-4-Ig), as measured by phage ELISA. The X axis lists each amino acid that was changed to alanine and its position. The Y axis is the ratio of the $EC_{50}$ for each variant to the $EC_{50}$ for the wild-type heregulin-β1 EGF-like domain, also displayed on phage. The $EC_{50}$ was calculated as the concentration of soluble receptor fusion required to displace 50% of the total amount of phage bound to immobilized receptor fusion. ErbB-3 binding results are shown with black bars, and ErbB-4 binding results are shown with white bars.

FIG. 4 shows the amino acid substitutions in the EGF-like domains of combination variants described in Example 3. The amino acid sequence of the wild-type heregulin-β1 EGF-like domain (HRG8), a variant of this domain containing a deletion of heregulin-β1 residues 202-204 (HRG63), and the analogous domain in EGF are shown on top. The residue numbering for the portion of the heregulin-β1 amino acid sequence shown is indicated above this sequence (numbered from the N-terminus of native human heregulin-β1). The residue numbering for the portion of the EGF amino acid sequence shown is indicated below this sequence (numbered from the N-terminus of native human EGF). A “.” indicates a residue that is identical to the wild-type residue at the particular position. A “-” indicates the absence of a residue.

DETAILED DESCRIPTION OF THE INVENTION

The present invention provides heregulin variants having one or more amino acid substitutions at selected residues. Included within the scope of the invention are variants of human heregulins, and, in particular, variants of human heregulin-β1. A heregulin variant according to the invention can have a single amino acid substitution at a selected residue or combinations of such substitutions.

In addition to the amino acid substitutions specified herein, heregulin variants according to the invention can have further modifications, including, for example, deletions of amino acids. In one embodiment, a heregulin variant has N- and C-terminal deletions, leaving only amino acids corresponding to “the minimal EGF-like domain,” which is sufficient for binding and activation of an ErbB receptor.

A heregulin variant of the invention is capable of binding an ErbB receptor, such as ErbB-3 or ErbB-4. In one embodiment, the variant has an enhanced affinity for an ErbB receptor compared to the affinity of the most homologous native heregulin. In addition to ErbB receptor binding, the heregulin variant can possess one or more other biological activities of a native heregulin.

Figure 3:
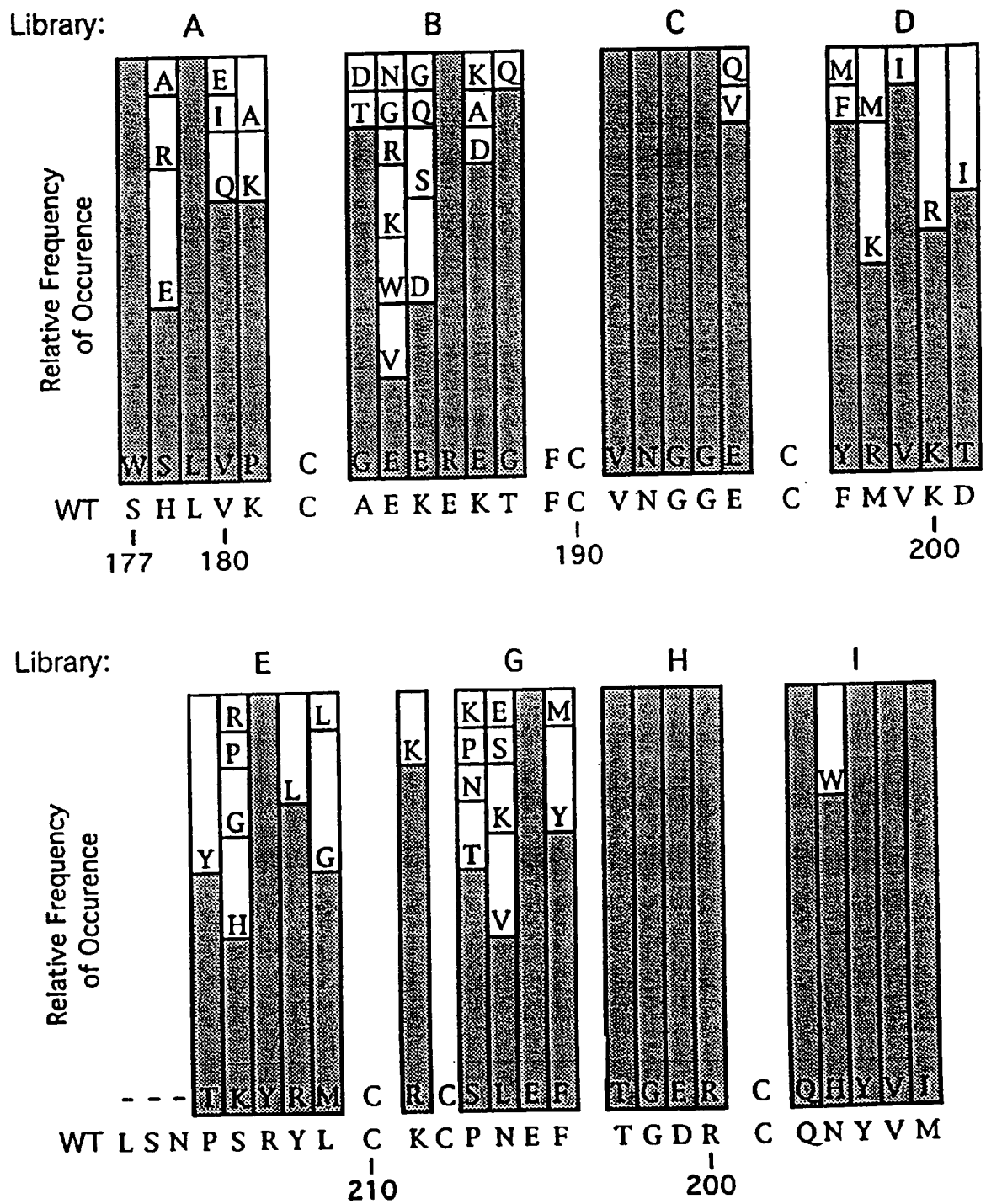
FIG. 3 shows the amino acids selected for binding to ErbB-3-Ig at each position in the heregulin-β1 EGF-like domain (heregulin-β1 residues 177-228) randomized in the phage display studies described in Example 3. The length of the bars indicates the frequency of occurrence of a particular amino acid at each position in the variants from phage display libraries A-E and G-I for which sequences were determined (i.e., a longer bar indicates a higher frequency). Twelve clones were sequenced from each library, although in library H, only one clone of the twelve represented a variant having mutations in the desired randomization window (see Example 3). "WT" indicates the wild-type amino acid sequence of the heregulin-β1 EGF-like domain.

The invention also provides nucleic acid molecules, vectors, and host cells related to the heregulin variants. A nucleic acid molecule of the invention encodes, or is complementary to a nucleic acid molecule encoding, a heregulin variant of the invention or a fragment thereof. The nucleic acid molecule can be double- or single-stranded DNA or RNA. A nucleic acid molecule of the invention can be inserted into an appropriate vector for propagation and/or expression of an encoded heregulin variant. Such vectors are introduced into suitable hosts, for example, to allow recombinant production of a heregulin variant.

The heregulin variants of the invention are useful in a variety of therapeutic and non-therapeutic applications. In particular, heregulin variants can be used in treating cancer and various diseases and disorders of the nervous system, musculature, and epithelia. Accordingly, the invention encompasses a pharmaceutical composition including a heregulin variant and related treatment methods.

Heregulin variants can also be employed in a variety of non-therapeutic applications, such as cell culture methods and diagnostic methods. For example, heregulin variants can be used to promote the ex vivo survival, proliferation, or differentiation of cells, including glial and muscle cells. In an exemplary diagnostic application, heregulin variants are employed in the diagnosis of a cancer characterized by erbB (e.g., erbB2) overexpression. Accordingly, the invention also includes kits useful in practicing the above-described methods.

DEFINITIONS

As used herein, the following words or phrases have the definitions indicated below, unless otherwise indicated.

The terms "amino acid" and "residue" are used interchangeably herein.

The term "wild-type amino acid" or "wild-type residue" means the amino acid present at a given position(s) in a native polypeptide.

Amino acids are denoted herein by the standard three-letter or one-letter code.

Residues in two or more polypeptides are said to "correspond" if the residues occupy an analogous position in the polypeptide structures. As is well known in the art, analogous positions in two or more polypeptides can be determined by aligning the polypeptide sequences based on amino acid sequence or structural similarities. Those skilled in the art understand that it may be necessary to introduce gaps in either sequence to produce a satisfactory alignment. For example, residues in human EGF that correspond to residues in human heregulin-β1 are shown in an alignment between the amino acid sequence of the heregulin-β1 EGF-like domain (heregulin-β1 residues 177-228) and the analogous EGF domain (EGF residues 1-48) in FIG. 4.

Residues in two or more heregulins are said to "correspond" if the residues are aligned in the best sequence alignment. The "best sequence alignment" between two polypeptides is defined as the alignment that produces the largest number of aligned identical residues. The best sequence alignment for a number of heregulin polypeptides is shown in FIG. 1.

Residue positions in heregulin-β1 are designated herein by the three-letter or one-letter code for the amino acid, followed by the position number, as numbered from the N-terminus of native human pro-heregulin-β1 (which is 645 amino acids in length). E.g., the serine at position 177 of heregulin-β1 is denoted "Ser177" or "S177."

Hereinafter, unless otherwise indicated, residue positions in a heregulin, heregulin variant, or related protein, such as EGF, are specified herein with reference to the amino acid numbering of native human heregulin-β1. For example, a heregulin-β1 variant can have a N-terminal deletion of residues 1-176. The first amino acid in this variant is identified herein as "the residue corresponding to Ser177 of 645-amino acid human heregulin-β1" because the first residue of the heregulin variant and Ser177 of heregulin-β1 are aligned in the best alignment between the two polypeptides.

Example 3 discloses heregulin-β1 variants containing residues corresponding to residues 177 to 228 of heregulin-β1, which is termed "the minimal EGF-like domain." For these variants, residue numbers also are expressed, in parentheses, in terms of the position of the residue in the minimal EGF-like domain (hereinafter "heregulin-β1 EGF" or "HRG-β1 EGF"), i.e., residues 1-52. Residue positions numbered according to native human heregulin-β1 can be converted to residue positions in the minimal EGF-like domain by subtracting 176 from the former position number. E.g., for heregulin-β1 Ser177, subtracting 176 from 177 gives 1, and thus heregulin-β1 EGF Ser1 identifies the same position as heregulin-β1 Ser177. The same numbering system is used in Example 4.

Amino acid substitutions are indicated by listing the residue position followed by the code for the amino acid substituted into the heregulin polypeptide. Thus, a substitution of alanine at Ser177 of heregulin-β1 is expressed as "heregulin-β1 Ser177Ala," "Ser177Ala", or "S177A." In this example, serine is the "replaced amino acid," and alanine is the "replacement amino acid."

As used to describe two amino acid sequences, the term "homologous" indicates that the amino acid sequences have some degree of amino acid sequence identity.

Heregulin Variants

The present invention includes a heregulin variant. The term "heregulin variant" means a polypeptide variant of a native heregulin. A native heregulin is defined as a polypeptide having the full-length amino acid sequence of any of the family of naturally occurring heregulin polypeptides. This family encompasses pro-heregulins as well as the soluble forms of these proteins The invention is exemplified with variants of human heregulin-β1. See Examples 1-3. However, the heregulin family encompasses any naturally occurring polypeptide having an EGF-like domain that has at least 70 percent sequence identity with the EGF-like domain of heregulin-β1 when these domains are aligned in the best alignment. Thus, a native heregulin can be from any species and one of a number of naturally occurring isoforms or allelic forms. Exemplary heregulin polypeptides include neu differentiation factors, glial growth factors, sensory and motor neuron-derived factor, and acetylcholine receptor inducing activity polypeptide.

In one embodiment, the heregulin variant is a variant of a mammalian heregulin. In a variation of this embodiment, the heregulin variant is a variant of a human heregulin. Examples of human heregulins include heregulin-α (HRG-α), heregulin-β1 (HRG-β1), heregulin-β2 (HRG-β2), heregulin-β3 (HRG-β3), and heregulin-γ (HRG-γ).

A heregulin variant according to the invention has an amino acid sequence not found in nature in which a wild-type residue in a native heregulin is replaced with a different residue. This amino acid substitution is at one or more selected residues corresponding to a residue of native human heregulin-β1. The selected residue(s) is chosen from the following group:

S177, H178, L179, V180, K181, E184, E186, K187, T188, V191, N192, G193, G194, E195, M198, V199, K200, D201, N204, P205, S206, R207, Y208, L209, K211, P213, N214, E215, T217, G218, D219, Q222, N223, Y224, S228, and F229.

In one embodiment, however, the amino acid substitution is not a replacement of the selected residue with an EGF residue corresponding to the selected residue. Substitution of any of the above residues in heregulin-β1 with alanine has at least a two-fold effect on affinity for the ErbB-3 or ErbB-4 receptors, as determined by phage ELISA. See Example 2.

In one embodiment, the selected residue is chosen from the following group:

S177, H178, L179, E186, K187, T188, V191, N192, G193, G194, E195, R207, L209, K211, P213, N214, T217, G218, Q222, Y224, and F229.

Substitution of the any of these residues in heregulin-β1 with alanine has at least a five-fold effect on affinity for the ErbB-3 or ErbB-4 receptors, as determined by phage ELISA. See Example 2.

In a variation of this embodiment, the selected residue is chosen from the following group:

H178, L179, K187, N192, G193, G194, E195, R207, K211, T217, G218, Q222, and Y224.

Substitution of the any of these residues in heregulin-β1 with alanine has at least a 10-fold effect on affinity for the ErbB-3 or ErbB-4 receptors, as determined by phage ELISA. See Example 2.

Generally, if function is to be preserved at a position selected for substitution, the residue used to replace the selected residue is not substantially different in character from the wild-type residue, i.e., the amino acid substitution is a conservative substitution. Amino acids can be grouped according to character as shown in Table 1.

TABLE 1

Groups of Amino Acids Having Similar Character

| Group | Character | Amino Acids |
|---|---|---|
| a | positively charged | Lys, Arg, His |
| b | negatively charged | Asp, Glu |
| c | amide | Asn, Gln |
| d | aromatic | Phe, Tyr, Trp |
| e | hydrophobic | Pro, Gly, Ala, Val, Leu, Ile, Met |
| f | uncharged hydrophilic | Ser, Thr |

To preserve function, therefore, the residue used to replace the wild-type residue is usually selected from the same group or a related group. In addition, serine or alanine can be used to replace most other residues. Table 2 shows conservative substitutions for each amino acid, identifying related groups for each and indicating which amino acids can be replaced with serine or alanine. Table 2 also shows preferred amino acid substitutions.

TABLE 2

Conservative Amino Acid Substitutions

| AA | Replacement Amino Acid Selected From | Preferred Substitutions |
|---|---|---|
| Ala | e*: Pro, Gly, Ala, Val, Leu, Ile, Met<br>f: Ser, Thr | Ser |
| Arg | a: Lys, Arg, His<br>Ser, Ala | Lys<br>Ser, Ala |
| Asn | a: Lys, Arg, His<br>c: Asn, Gln<br>Ser, Ala | Gln<br>Ser, Ala |
| Asp | b: Asp, Glu<br>c: Asn, Gln<br>Ser, Ala | Glu<br>Ser, Ala |
| Cys | e: Pro, Gly, Ala, Val, Leu, Ile, Met<br>f: Ser, Thr | Ala<br>Ser |
| Gln | a: Lys, Arg, His<br>c: Asn, Gln<br>Ser, Ala | Asn<br>Ser, Ala |
| Glu | b: Asp, Glu<br>c: Asn, Gln<br>Ser, Ala | Asp<br>Ser, Ala |
| Gly | e: Pro, Gly, Ala, Val, Leu, Ile, Met<br>f: Ser, Thr | Pro, Ala |
| His | a: Lys, Arg, His<br>Ser, Ala | Arg<br>Ser, Ala |
| Ile | e: Pro, Gly, Ala, Val, Leu, Met | Ala, Val, Leu |
| Leu | e: Pro, Gly, Ala, Val, Ile, Met | Ala, Val, Ile |
| Lys | a: Lys, Arg, His<br>Ser, Ala | Arg<br>Ser, Ala |
| Met | e: Pro, Gly, Ala, Val, Leu, Ile, Met | Ala, Val, Leu, Ile |
| Phe | a: Lys, Arg, His<br>d: Phe, Tyr, Trp<br>Ala, Val, Leu, Ile | Tyr<br>Ala, Val, Leu, Ile |
| Pro | a: Lys, Arg, His<br>d: Phe, Tyr, Trp<br>Gly, Ala | Phe<br>Gly, Ala |
| Ser | a: Lys, Arg, His<br>f: Ser, Thr<br>Ala | Thr<br>Ala |
| Thr | a: Lys, Arg, His<br>f: Ser, Thr<br>Ala | Ser<br>Ala |
| Trp | d: Phe, Tyr, Trp<br>Ala | Phe<br>Ala |
| Tyr | d: Phe, Tyr, Trp<br>Ala, Val, Leu, Ile | Phe,<br>Ala, Val, Leu, Ile |
| Val | e: Pro, Gly, Ala, Val, Leu, Ile, Met Ser, Ala | Leu, Ile,<br>Ser, Ala |

*Wild-type amino acid.
Lower-case letters refer to the groups of amino acids in Table 1.

In one embodiment, the heregulin variant is a variant of human heregulin-β1 and includes an amino acid substitution(s) chosen from the following group:

S177W; H178S, E, R, or A; V180Q, I, or E; K181P or A; A183G, T, or D; E184V, W, K, R, G, or N; K185E, S, Q, or G; E186R; K187E or A; T188Q; E195Q; F197Y; M198R or K; K200R; D201T or I; P205T or Y; S206K, H, G, P, or R; R207Y; Y208R or L; L209M or G; K211R; P213S, T, N, or K; N214L, K, S, or E; F216M; N223H or W; and M226I.

Another aspect of the invention is a variant of human heregulin-β1 including a set of amino acid substitutions, such as any of the heregulin variants described in Example 3. The set of amino acid substitutions is chosen from the group indicated below (the variant number from Example 3 is shown in the left-hand column, followed by the set of amino acid substitutions for that variant):

| | |
|---|---|
| B5: | A183G, E184W, K185D, E186R, K187E, T188G, M226I; |
| B10: | A183D, E184K, K185S, E186R, K187E, T188G, M226I; |
| D1: | F197Y, M198K, K200R, D201I, M226I; |
| E2: | P205Y, S206G, R207Y, Y208L, L209M; |
| E3: | P205Y, S206R, R207Y, Y208R, L209M, M226I; |
| E6: | P205T, S206H, R207Y, Y208R, L209M; |
| E8: | P205T, S206K, R207Y, Y208R, L209G; |
| I1: | N223W, M226I; |
| I2: | N223H, M226I; |
| HRG37: | S177W, H178E, K181P, A183G, E184W, K185D, E186R, K187E, T188G, M226I; |
| HRG48: | P205Y, S206G, R207Y, Y208L, L209M, M226I; |
| HRG53: | A183G, K185E, E186R, K187E, T188G, F197Y, M198R, D201T; |
| HRG54: | A183G, K185E, E186R, K187E, T188G, P205Y, S206G, R207Y, Y208L, L209M; |
| HRG55: | A183G, K185E, E186R, K187E, T188G, F197Y, M198R, D201T, P205Y, S206G, R207Y, Y208L, L209M; |
| HRG56: | A183G, K185E, E186R, K187E, T188G, M226I; |
| HRG57: | F197Y, M198R, D201T, P205Y, S206G, R207Y, Y208L, L209M; |
| HRG58: | F197Y, M198R, D201T, P205Y, S206G, R207Y, Y208L, L209M, M226I; |
| HRG59: | F197Y, M198R, D201T, M226I; |
| HRG60: | A183G, K185E, E186R, K187E, T188G, F197Y, M198R, D201T, M226I; |
| HRG61: | A183G, K185E, E186R, K187E, T188G, P205Y, S206G, R207Y, Y208L, L209M, M226I; |
| HRG62: | A183G, K185E, E186R, K187E, T188G, F197Y, M198R, D201T, P205Y, S206G, R207Y, Y208L, L209M, M226I; |
| HRG71: | F197Y, M198R, D201T, P205Y, S206G, R207Y, Y208L, L209M, N223H, M226I; and |
| HRG73: | A183G, K185E, E186R, K187E, T188G, F197Y, M198R, D201T, P205Y, S206G, R207Y, Y208L, L209M, N223H, M226I. |

Each of these sets of amino acid substitutions produces at least a five-fold increase in ErbB-3 receptor affinity, as determined by phage ELISA. See Example 3.

In a variation of this embodiment, the set of amino acid substitutions is chosen from the following group:

| | |
|---|---|
| B5: | A183G, E184W, K185D, E186R, K187E, T188G, M226I; |
| E2: | P205Y, S206G, R207Y, Y208L, L209M; |
| I2: | N223H, M226I; |
| HRG48: | P205Y, S206G, R207Y, Y208L, L209M, M226I; |
| HRG53: | A183G, K185E, E186R, K1872, T188G, F197Y, M198R, D201T; |
| HRG56: | A183G, K185E, E186R, K187E, T188G, M226I; |
| HRG57: | F197Y, M198R, D201T, P205Y, S206G, R207Y, Y208L, L209M; |
| HRG58: | F197Y, M198R, D201T, P205Y, S206G, R207Y, Y208L, L209M, M226I; |
| HRG59: | F197Y, M198R, D201T, M226I; |
| HRG60: | A183G, K185E, E186R, K187E, T188G, F197Y, M198R, D201T, M226I; |
| HRG61: | A183G, K185E, E186R, K187E, T188G, P205Y, S206G, R207Y, Y208L, L209M, M226I; |
| HRG62: | A183G, K185E, E186R, K187E, T188G, F197Y, M198R, D201T, P205Y, S206G, R207Y, Y208L, L209M, M226I; |
| HRG71: | F197Y, M198R, D201T, P205Y, S206G, R207Y, Y208L, L209M, N223H, M226I; and |
| HRG73: | A183G, K185E, E186R, K187E, T188G, F197Y, M198R, D201T, P205Y, S206G, R207Y, Y208L, L209M, N223H, M226I. |

Each of these sets of amino acid substitutions produces at least a 20-fold increase in ErbB-3 receptor affinity, as determined by phage ELISA. See Example 3.

In another variation of this embodiment, the set of amino acid substitutions is chosen from the following group:

| | |
|---|---|
| HRG58: | F197Y, M198R, D201T, P205Y, S206G, R207Y, Y208L, L209M, M226I; |
| HRG60: | A183G, K185E, E186R, K187E, T188G, F197Y, M198R, D201T, M226I; |
| HRG71: | F197Y, M198R, D201T, P205Y, S206G, R207Y, Y208L, L209M, N223H, M226I; and |
| HRG73: | A183G, K185E, E186R, K187E, T188G, F197Y, M198R, D201T, P205Y, S206G, R207Y, Y208L, L209M, N223H, M226I. |

Each of these sets of amino acid substitutions produces at least a 50-fold increase in ErbB-3 receptor affinity, as determined by phage ELISA. See Example 3.

The invention also includes a heregulin variant that has a greater specificity for the ErbB-4 receptor, relative to the ErbB-3 receptor, than the heregulin from which the heregulin variant is derived. Such enhanced ErbB-4 receptor specificity can be measured, for Example, as a lower variant:wild-type $EC_{50}$ ratio for binding to the ErbB-4 receptor than for binding to ErbB-3 receptor. Generally, a heregulin variant having enhanced ErbB-4 receptor specificity has approximately wild-type affinity for the ErbB-4 receptor or better together with a significantly reduced (i.e., at least about 5-10-fold) affinity for the ErbB-3 receptor.

In one embodiment, a heregulin variant having enhanced ErbB-4 receptor specificity has an amino acid substitution at a selected residue corresponding to a residue of 645-amino acid native human heregulin-β1 selected from the group consisting of H178, L179, and R207. For example, the invention provides a human heregulin-β1 variant including the amino acid substitution H178E or R207P.

In another embodiment, a heregulin variant having enhanced ErbB-4 receptor specificity has a deletion of amino acid residues corresponding to residues S228 to K231 of 645-amino acid native human heregulin-β1 and a substitution of a single methionine for the deleted residues. In a variation of this embodiment, the heregulin variant also includes the amino acid substitution H178L.

In addition to the above amino acid substitutions, the heregulin variant can optionally have any of the following modifications, singly or in combination: (1) one or more additional amino acid substitutions; (2) one or more amino acids added to the N- or C-terminus of, or inserted within, the amino acid sequence of the heregulin variant; (3) one or more amino acids deleted from the heregulin variant; and (4) one or more covalent modifications of an amino acid in the heregulin variant.

Thus, the heregulin variant can be "substantially full-length," which, as used herein, means that the heregulin variant is at least 90% as long as the native heregulin to which the variant is most homologous. Alternatively, the heregulin variant can be a "fragment" that is less than 90% as long as the most homologous native heregulin. Heregulin variants that are fragments are usually about 30 to about 100 amino acids, more usually about 40 to about 60 amino acids, even more usually about 45 to about 65 amino acids, and most usually about 50 amino acids in length.

For example, the heregulin variant can include amino acids corresponding to "the minimal EGF-like domain." The minimal EGF-like domain is a portion of a native heregulin that is sufficient for binding and activation of an ErbB receptor. In general, the minimal EGF-like domain is less than about 70 amino acids and usually less than about 60 amino acids in length. As used herein with reference to human heregulin-β1, the minimal EGF-like domain extends from residues 177-228. Unless otherwise indicated, "HRG-β1 EGF" refers to the minimal EGF-like domain.

Examples of suitable covalent modifications of a heregulin variant according to the invention include, but are not limited to, conjugation with a detectable label, "pegylation," and conjugation with a cytotoxic agent. A heregulin variant can be conjugated to any of a wide variety of available labels to produce a conjugate useful for detecting the presence of ErbB receptors in a sample. Suitable labels include a radioisotope, a fluorescent label, and an enzyme label. Exemplary radioisotope labels are $^{35}S$, $^{14}C$, $^{125}I$, $^{3}H$, and $^{131}I$. Heregulin variants can be conjugated to radioisotopes as described generally in *Current Protocols in Immunology* Vols. 1 & 2 (Coligen et al. ed., Wiley Publishers).

Fluorescent labels suitable for conjugation to a heregulin variant include a rare earth chelate (a europium chelate), fluorescein, rhodamine, dansyl, Lissamine, phycoerythrin, and Texas Red, and derivatives thereof. Conjugates can be prepared as described, for example, in *Current Protocols in Immunology* supra.

Various enzyme-substrate systems are available, and U.S. Pat. No. 4,275,149 provides a review of some of these. In general, enzymes useful in such systems catalyze a readily detectable chemical alteration of a substrate. For example, the enzyme can catalyze a color change, which can be measured spectrophotometrically, or a change in fluorescence or chemiluminescence, which can be detected using a fluorometer or chemiluminometer, respectively. Exemplary enzyme labels include a luciferase, malate dehydrogenase, urease, a peroxidase, alkaline phosphatase, β-galactosidase, glucoamylase, lysozyme, a saccharide oxidase, a heterocyclic oxidase, lactoperoxidase, microperoxidase, and the like. Heregulin variants can be conjugated to enzyme labels as described generally in O'Sullivan et al., *Methods in Enzyn.* 73:47-166 (1981), and in *Current Protocols in Immunology* (supra). Suitable substrates for use with a given enzyme label are well known to those skilled in the art.

Another exemplary modification of a heregulin variant of the invention is pegylation, which refers to the conjugation of one or more polyethylene glycol (PEG) groups to the ε-amino group(s) of a polypeptide. Pegylation may be desired when the heregulin variant is intended for pharmaceutical use, as pegylation can increase in vivo half-life and/or reduce immunogenicity and potential toxicity of therapeutic proteins. See, e.g., Abuchowski et al., *J. Biol. Chem.* 252:3582-86 (1977).

Conjugation of a heregulin variant with a cytotoxic agent produces a targeted cytotoxic agent that specifically binds cells expressing appropriate ErbB receptors on their surface. The term "cytotoxic agent" refers to a substance that inhibits or prevents the function of cells and/or causes destruction of cells. The term includes, for example, a radioactive isotope (e.g., I, Y, Pr) and a chemotherapeutic agent.

A "chemotherapeutic agent" is defined herein as any chemical compound useful in the treatment of cancer. The term "cancer" refers to the physiological condition in mammals that is characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Examples of chemotherapeutic agents include Adriamycin, Doxorubicin, 5-Fluorouracil (5-FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Carminomycin, Aminopterin, Dactinomycin, a Mitomycin, Nicotinamide, an Esperamicin, Melphalan and any related nitrogen mustard, and an endocrine therapeutic (such as diethylstilbestrol [DES], Tamoxifen, a leutinizing hormone releasing hormone-antagonizing drug, a progestin, an anti-progestin, etc.).

In addition to conjugation to a chemical compound, any of the above-described heregulin variants can be modified by fusion to a heterologous polypeptide to produce a "chimeric heregulin variant." (Chimeric heregulin variants are also referred to herein as "fusion proteins.") Typically, the heterologous polypeptide is fused at the N- or C-terminus of the heregulin variant to preserve the biological activity (described further below) of the heregulin variant. However, the heterologous polypeptide can also be introduced into regions of the heregulin variant that are not critical for biological activity. Generally, chimeric heregulin variants are produced by recombinant techniques. Examples of chimeric heregulin variants include a heregulin variant fused to a "signal sequence," a "purification handle" and an immunoglobulin sequence.

A "signal sequence" is an amino acid sequence that directs the secretion of a polypeptide fused thereto from a cell expressing the chimeric protein. Thus, fusion of a heregulin variant to a signal sequence facilitates recombinant production of the heregulin variant because the chimeric heregulin variant is secreted into the host cell culture medium, from which the chimeric heregulin variant can be recovered with relative ease.

A suitable signal sequence can be obtained from any protein that has a signal sequence and is typically (but not always) fused to the N-terminus of the heregulin variant. DNA encoding prokaryotic signal sequences can be obtained, for example, from lamB or ompF, MalE, PhoA, and other genes. A convenient prokaryotic signal sequence for practicing the invention is the *E. coli* heat-stable enterotoxin II (STII) signal sequence.

A "purification handle" is a polygon of a polypeptide that binds another polypeptide, termed a "binding partner." The fusion of a purification handle to a heregulin variant confers on the variant the ability to bind the binding partner, which facilitates purification of the resultant chimeric heregulin variant. Generally, the purification handle is selected so that the binding partner does not substantially cross-react with other components present in the mixture from which the chimeric heregulin variant is to be purified. As used herein, the term "does not substantially cross-react" means that the affinity of the binding partner for the purification handle is at least about 20-fold, usually at least about 100-fold, more usually at least about 1000-fold, any affinity for any other components present in the mixture.

In one embodiment, the purification handle is an epitope recognized by an antibody, and the chimeric heregulin variant is therefore termed an "epitope-tagged heregulin variant." Suitable epitopes generally have at least five amino acids, usually between about 10 and about 50 amino acids, and more usually between about 10 and about 30 amino acids.

A chimeric molecule that includes a heregulin variant fused to an immunoglobulin sequence is termed "a heregulin variant immunoadhesin." In one embodiment, the immunoglobulin sequence is an immunoglobulin constant domain. The immunoglobulin sequence in a heregulin variant immunoadhesin can be obtained from $IgG_1$, $IgG_2$, $IgG_3$ or $IgG_4$ subtypes, IgA, IgE, IgD, or IgM. In one embodiment, the immunoglobulin sequence is obtained from $IgG_1$ or $IgG_3$.

Other examples of chimeric heregulin variants include heregulin variants fused to thioredoxin, a "salvage receptor binding epitope," or a cytotoxic polypeptide. Fusion of a heregulin variant with thioredoxin enhances expression and provides a purification handle that facilitates purification using phenylarsine oxide, which can be covalently bound to a solid support, such as agarose. (Agarose functionalized with phenylarsine is available commercially as Thibond™ Resin from Invitrogen Corp., San Diego, Calif.) Exemplary thioredoxin-variant fusion proteins are described in Example 2.

The term "salvage receptor binding epitope" refers to an epitope of the Fc region of an IgG molecule (e.g., $IgG_1$, $IgG_2$, $IgG_3$, or $IgG_4$) that increases the in vivo serum half-life of the IgG. Salvage receptor binding epitopes suitable for fusion to a heregulin variant according the invention include any of the known salvage receptor binding epitopes.

The term "cytotoxic polypeptide" refers to a polypeptide that inhibits a cellular function or kills cells. Cytotoxic polypeptides suitable for fusion to a heregulin variant include an enzymatically active toxin of bacterial, fungal, plant, or animal origin and fragments thereof and an oncogene product/tyrosine kinase inhibitor, such as a peptide that inhibits binding of a tyrosine kinase to a SH2-containing substrate protein (see WO 94/07913, for example).

In one embodiment, a chimeric heregulin variant includes a heregulin variant fused to an enzyme that converts a "prodrug" to an active drug. Typically, the "prodrug" is a precursor or derivative form of a cytotoxic drug that is less cytotoxic than the drug itself and is capable of being enzymatically activated or converted to the cytotoxic drug. The prodrugs of this invention include, but are not limited to, a phosphate-containing prodrug, a thiophosphate-containing prodrug, a sulfate-containing prodrug, a peptide-containing prodrug, a D-amino acid-modified prodrug, a glycosylated prodrug, a β-lactam-containing prodrug, a phenoxyacetamide-containing prodrug, a phenylacetamide-containing prodrug, 5-fluorocytosine, a 5-fluorouridine prodrug, and derivatives thereof. Examples of cytotoxic drugs that can be derivatized to produce a prodrug for use in this invention include, but are not limited to, those chemotherapeutic agents described above.

A heregulin variant according to the invention is capable of binding an ErbB receptor. The term "ErbB receptor" refers to any of the mammalian class I tyrosine kinase receptors. Examples of such receptors include the ErbB-1 receptor (also known as "the EGF receptor"), the ErbB-2 receptor (also called "the HER2 receptor."), the ErbB-3 (or "HER3") receptor, and the ErbB-4 (or "HER4") receptor. The phrase "capable of binding" is used to describe a polypeptide that binds another polypeptide with a dissociation constant ($K_d$) of at least 1 mM.

Exemplary heregulin variants that are capable of binding the ErbB-3 and ErbB-4 receptors are discussed above and in the examples. The production of additional heregulin variants, having further modifications (e.g, additional amino acid substitutions, additions, insertions, or deletions, or covalent modifications) and of chimeric heregulin variants is within the level of skill in the art.

Furthermore, in light of the teachings herein, those skilled in the art can design a large number of additional variants that preserve the binding activity of the heregulin variants of the invention. For example, a conservative substitution in a non-critical residue of a heregulin variant (as identified in Example 2) is not expected to significantly alter ErbB receptor binding. Moreover, any effects on ErbB receptor binding can readily be determined in a simple binding assay, such as those described in Examples 1-3. Thus, the invention encompasses all heregulin variants having amino acid substitutions at the specific positions discussed above, regardless of any additional modifications that may be present.

In addition to ErbB receptor binding, a heregulin variant of the invention can possess one or more other biological activities of a native heregulin. For example, the heregulin variant can also have the ability to activate an ErbB receptor. The phrase "ability to activate an ErbB receptor" refers to the ability to cause the intracellular kinase domain of an ErbB receptor to phosphorylate tyrosine residues. Generally, receptor activation involves binding of a heregulin to a receptor complex of two or more ErbB receptors (e.g., an ErbB-2/ErbB-3 or ErbB-2/ErbB-4 complex). Receptor binding activates a kinase domain of one or more of the receptors, which results in phosphorylation of tyrosine residues in one or more of the receptors and/or phosphorylation of tyrosine residues in additional substrate polypeptides(s). ErbB receptor phosphorylation can be quantified using the tyrosine phosphorylation assays described in Example 3.

Furthermore, a heregulin variant of the invention can be capable of enhancing the survival, proliferation, and or differentiation of cells having suitable ErbB receptors. The phrase "enhancing survival of cells" refers to increasing the period of existence of cells, either in vitro or in vivo, relative to the period of existence of cells that have not been exposed to the heregulin variant ("untreated cells").

The expression "enhancing proliferation of cells" means increasing the rate or number of mitotic divisions, either in vitro or in vivo, relative to untreated cells. An increase in cell proliferation in cell culture can be detected by counting the number of cells before and after exposure to the heregulin variant or by microscopic examination of the degree of confluency. Cell proliferation can also be quantified by measuring $^3$H-thymidine uptake by the cells.

The phrase "enhancing differentiation of cells" refers to increasing the extent of cell specialization. Cell specialization is characterized by the acquisition of one or more characteristics that differ from those of the original cells. Thus, the extent of cell specialization is typically determined by screening for a change in the phenotype of the cell (e.g., identifying a change in cellular morphology).

Exemplary cells that express ErbB receptors, and are therefore responsive to heregulins, include SK-BR-3 cells, glial cells, glioblastoma cells, Schwann cells, hepatocytes, epithelial cells, and muscle cells. Glial cells are derived from the central nervous system and include oligodendrocytes and astrocytes. Muscle cells expressing ErbB receptors include muscle cell precursors (myoblasts) as well as the more specialized skeletal, cardiac, and smooth muscle cells.

Other biological activities that a heregulin variant of the invention can possess include induction of ion channel (e.g. $Na^+$ channel) formation; induction of acetylcholine receptor synthesis at the neuromuscular junction; enhancement of the formation of a synaptic junction between a neuron and a muscle, nerve, or glandular cell; downregulation of estrogen receptor; and cell internalization (possibly associated with nuclear localization).

A heregulin variant is produced by any suitable method, including peptide synthesis and recombinant techniques. Generally, recombinant techniques, which are described in detail below, are employed for a heregulin variant longer than about 50 or amino acids.

A heregulin variant having enhanced specificity for the ErbB-4 receptor, relative the ErbB-3 receptor, can be prepared by mutagenizing at one or more heregulin residues and selecting variants having enhanced ErbB-4 receptor specificity. Generally, a residue chosen for mutagenesis in this context is characterized by a difference in effect on binding to the ErbB-4 receptor, as compared the effect on binding to the ErbB-3 receptor. Such residues are evident, for instance, from the alanine-scanning data presented in Example 2.

Variants having enhanced ErbB-4 receptor specificity are selected by screening for binding to ErbB-4 receptor using any suitable screening method, such as monovalent phage display, which described in Example 4. The results can be improved by subjecting variants to "counter-selection," which in this case entails the removal of variants that bind with high affinity to the ErbB-3 receptor. Example 4 demonstrates that counter-selection against ErbB-3-Ig produces a significant enrichment in variants exhibiting greater specificity for ErbB-4-Ig, relative to ErbB-3-Ig, than that of wild-type HRG-β1.

Nucleic Acid Molecules

The present invention also includes a nucleic acid molecule related to the heregulin variant. The term "nucleic acid molecule" encompasses single-stranded and double-stranded DNA molecules, including genomic DNA, cDNA, DNA produced by an amplification reaction (such as polymerase chain reaction ["PCR"]), and DNA produced by oligonucleotide synthesis, as well as RNA molecules, such as mRNA. Genomic DNA can include non-transcribed and transcribed regions (such as 5' and 3' non-coding regions, introns, and heregulin variant coding regions). cDNA and mRNA molecules contain sequences corresponding to transcribed regions.

A nucleic acid molecule according to the invention has a nucleotide sequence not found in nature and encodes, or is complementary to a nucleic acid molecule encoding, a heregulin variant of the invention or a fragment thereof. A complementary nucleotide sequence is capable of forming Watson-Crick bonds with its complement, in which adenine pairs with thymine or uracil and guanine pairs with cytosine. A double-stranded DNA molecule encodes one of the heregulin variants, whereas a single-stranded DNA or RNA molecule is either the coding (sense) strand or the noncoding (anti-sense) strand. When the nucleic acid molecule encodes (or is complementary to a nucleic acid molecule encoding) a fragment of a heregulin variant, the fragment includes at least one amino acid substitution.

Because of the redundancy of the genetic code, there are a large number of possible nucleic acid molecules related to each heregulin variant. More specifically, because several different codons encode the same amino acid, a large number of different nucleic acid molecules encode (or are complementary to a nucleic acid molecule encoding) the same heregulin variant.

Generally, a heregulin variant of the invention is produced by mutating a naturally occurring DNA sequence to introduce the desired mutations into the heregulin variant amino acid sequence. However, it may also be advantageous to change one or more codons in a nucleic acid molecule without altering the encoded amino acid. Examples of such "silent mutations" within the scope of the present invention include, for example, mutations that create or destroy restriction endonuclease sites to facilitate construction of a desired vector and mutations that enhance expression of the encoded heregulin variant. Examples of the latter include nucleotide substitutions designed to reduce the formation of 5' stem and loop structures in the transcribed mRNA or to provide codons that are more readily transcribed by the selected host (e.g., the well-known preference codons for *E. coli* or yeast expression).

A nucleic acid molecule of the invention can be incorporated into a vector (as described further below) or used, for example, as a hybridization probe or an amplification primer. A hybridization probe according to the present invention is useful for detecting a nucleic acid molecule containing a desired mutation, such as, for example, in screening bacterial transformants to identify clones containing the mutated nucleic acid molecule.

Such probes are generally at least about 20 nucleotides and usually less than two kilobases. The probe includes a number of nucleotides that is sufficient, under the hybridization conditions used, to hybridize with a mutated sequence to be detected and to be substantially free from hybridization with other sequences. Typically, a probe of the present invention is at least about 50 nucleotides, and usually about 100 nucleotides in length.

An amplification primer according to the invention can be used in a conventional amplification protocol, such as PCR, to detect a nucleic acid molecule containing a desired mutation or to produce sufficient amounts of such a molecule for sequencing, insertion into a vector, etc. An amplification primer is typically used as a member of a primer pair, including a 5' upstream primer that hybridizes with the 5' end of the nucleic acid sequence to be amplified and a 3' downstream primer that hybridizes with the complement of the 3' end of the sequence to be amplified.

In general, a primer according to the invention includes a number of nucleotides that is sufficient, under the hybridization conditions used, to hybridize with a mutated sequence and to be substantially free from hybridization with other sequences. The specificity of the primer increases with the number of nucleotides that hybridize with the mutated sequence. In addition, specificity is correlated with the proportion of residues in the primer that hybridize with the mutated sequence. A primer of the present invention generally includes at least about 15 nucleotides, and usually at least about 20 nucleotides. The primer need not exceed about 30 nucleotides, and usually does not exceed about 25 nucleotides. In one variation of this embodiment, the primer includes between about 20 and about 25 nucleotides. Generally, the primers should have a $T_m$ in the range of about 55° C. to about 75° C. In practice, the $T_m$ is usually between about 60° C. to about 65° C. to facilitate amplification under stringent conditions.

Vectors and Host Cells

A nucleic acid molecule of the present invention can be incorporated into a vector for propagation and/or expression in a host cell. Such vectors typically contain a replication sequence capable of effecting replication of the vector in a suitable host cell (i.e., an origin of replication) as well as sequences encoding a selectable marker, such as an antibiotic resistance gene. Upon transformation of a suitable host, the vector can replicate and function independently of the host genome or integrate into the host genome. Vector design depends, among other things, on the intended use and host cell for the vector, and the design of a heregulin variant vector for a particular use and host cell is within the level of skill in the art.

If the vector is intended for expression of a heregulin variant, the vector includes one or more control sequences capable of effecting and/or enhancing the expression of an operably linked heregulin variant coding sequence. Control sequences that are suitable for expression in prokaryotes, for example, include a promoter sequence, an operator sequence, and a ribosome binding site. Control sequences for expression in eukaryotic cells include a promoter, an enhancer, and a transcription termination sequence (i.e., a polyadenylation signal).

The term "operably linked" means that two nucleic acid sequences are in a functional relationship with one another. For example, a promoter (or enhancer) is operably linked to a coding sequence if it effects (or enhances) the transcription of the sequence. A ribosome binding site is operably linked to a coding sequence if it is positioned to facilitate translation. Operably linked nucleic acid sequences are often contiguous, but this is not a requirement. For example, enhancers need not be contiguous with a coding sequence to enhance transcription of the coding sequence.

A heregulin variant expression vector can also include other sequences, such as, for example, nucleic acid sequences encoding a signal sequence or an amplifiable gene. As discussed above, a signal sequence directs the secretion of a polypeptide fused thereto from a cell expressing the chimeric protein. In the expression vector, nucleic acid encoding a signal sequence is linked to a heregulin variant coding sequence so as to preserve the reading frame of the heregulin variant coding sequence. The inclusion of an amplifiable gene (e.g., the dihydrofolate reductase [DHFR] gene) in a heregulin variant expression vector allows selection of host cells containing multiple copies of the nucleic acid molecule encoding the heregulin variant.

A vector of the present invention is produced by linking desired elements by ligation at convenient restriction sites. If such sites do not exist, suitable sites can be introduced by standard mutagenesis (e.g., site-directed or cassette mutagenesis) or synthetic oligonucleotide adaptors or linkers can be used in accordance with conventional practice.

The present invention also provides a host cell containing a vector of this invention. A wide variety of host cells are available for propagation and/or expression of vectors. Examples include prokaryotic cells (such as *E. coli* and strains of *Bacillus, Pseudomonas*, and other bacteria), yeast or other fungal cells, insect cells, plant cells, and phage, as well as higher eukaryotic cells (such as Chinese hamster ovary cells and other mammalian cells). Host cells according to the invention include cells in culture and cells present in live animals, such as transgenic animals. See U.S. Pat. No. 5,364,934 for more information on vectors and host cells suitable for use in the recombinant production of a heregulin variant.

A vector of the present invention is introduced into a host cell by any convenient method, which will vary depending on the vector-host system employed. Generally, a vector is introduced into a host cell by transformation (also known as "transfection") or infection with a virus (e.g., phage) bearing the vector. If the host cell is a prokaryotic cell (or other cell having a cell wall), convenient transformation methods include the calcium treatment method described by Cohen et al., *PNAS USA* 69:2110-14 (1972), and the polyethylene glycol method of Chung et al., *Nuc. Acids. Res.* 16:3580 (1988). If a prokaryotic cell is used as the host and the vector is a phagemid vector, the vector can be introduced into the host cell by infection, as described in Example 1. Yeast cells can be transformed using polyethylene glycol, for example, as taught by Hinnen, *PNAS U.S.A.* 75:1929-33 (1978). Mammalian cells are conveniently transformed using the calcium phosphate precipitation method described by Graham et al., *Virology* 52:546 (1978), and Gorman et al., *DNA and Protein Eng. Tech.* 2:3-10 (1990). However, other known methods for introducing DNA into host cells, such as nuclear injection, electroporation (see Example 1), and protoplast fusion also are suitable for use in the invention.

In one embodiment, a host cell containing a nucleic acid molecule encoding a heregulin variant is produced by homologous recombination, as described in WO 91/06667. Briefly, this method involves transforming a host cell containing an endogenous heregulin gene with a homologous recombination vector that includes the sequence to be introduced. The homologous recombination vector also includes at least one sequence of at least about 150 nucleotides in length that is homologous with an endogenous sequence flanking the endogenous heregulin gene. Suitable flanking sequences are readily identified, for example, by the method of genomic walking, using a known native heregulin nucleic acid sequence as a starting point. The homologous recombination vector additionally includes an amplifiable gene, such as the DHFR gene.

Transformation is carried out under conditions such that the vector integrates into the host cell genome by recombination. Cells that integrate the vector are then cultured under conditions that select for amplification of the amplifiable gene. The resulting cells are then screened for high levels of heregulin variant production.

Recombinant Production of Heregulin Variants

To produce a heregulin variant recombinantly, host cells containing a heregulin variant expression vector are prepared and cultured under conditions suitable for cell growth and for expression of the heregulin variant. In particular, the culture medium contains appropriate nutrients and growth factors for the host cell employed. The nutrients and growth factors required for growth of a selected host cell are, in many instances, well known or can be readily determined empirically by those skilled in the art. Suitable culture conditions for mammalian host cells, for instance, are described in *Mammalian Cell Culture* (Mather ed., Plenum Press 1984), and in Barnes and Sato, *Cell* 22:649 (1980).

In addition, the culture conditions should allow transcription, translation, and protein transport between cellular compartments. Factors that affect these processes are well-known and include, for example, DNA/RNA copy number; factors that stabilize RNA; nutrients, supplements, and transcriptional inducers or repressors present in the culture medium; temperature, pH, and osmolality of the culture; and cell density. The adjustment of these factors to promote expression in a particular vector-host cell system is within the level of skill in the art. Principles and practical techniques for maximizing the productivity of in vitro mammalian cell cultures, for example, can be found in *Mammalian Cell Biotechnology: a Practical Approach* (Butler ed., IRL Press 1991).

The cell culture procedure employed in the production of a heregulin variant of the present invention can be any of a number of well-known procedures for large- or small-scale production of proteins. These include, but are not limited to, the use of a fluidized bed bioreactor, a hollow fiber bioreactor, a roller bottle culture system, and a stirred tank bioreactor system. A heregulin variant can be produced, for instance, in a batch, fed-batch, or continuous mode process.

Methods for recovery of recombinant proteins produced as described above are well-known and vary depending on the expression system employed. For example, if, as is typical, the heregulin variant is fused to a signal sequence, the heregulin variant is recovered from the culture medium or the periplasm. Conveniently, the variant is secreted into the periplasmic space as a mature protein. The heregulin variant can also be expressed intracellularly and recovered from cell lysates.

The heregulin variant can be purified from culture medium or a cell lysate by any method capable of separating the variant from components of the host cell or culture medium. Typically the heregulin variant is separated from host cell and/or culture medium components that would interfere with the intended use of the heregulin variant. As a first step, the culture medium or cell lysate is usually centrifuged or filtered to remove cellular debris. The supernatant is then typically concentrated or diluted to a desired volume or diafiltered into a suitable buffer to condition the preparation for further purification.

The heregulin variant is typically further purified in the same manner as the most homologous native heregulin, taking account of any substantial differences in properties between the two molecules. For example, if the heregulin variant is an epitope-tagged heregulin variant, purification can be carried out using an immunoaffinity column containing antibody to the epitope tag. The following exemplary procedures for purifying heregulins can be used or adapted for purifying a heregulin variant of the invention: fractionation on an immunoaffinity column, fractionation on an ion-exchange column, ammonium sulphate or ethanol precipitation, reverse phase HPLC, chromatography on silica, chromatography on heparin Sepharose, chromatography on a cation exchange resin, chromatofocusing, SDS-PAGE, and gel filtration (e.g., using a High Load Superdex 75™ prep grade column).

If the heregulin variant is expressed initially as an insoluble, aggregated form (especially in bacterial host cells), it may be necessary to solubilize and renature the heregulin variant using techniques available in the art for solubilizing and renaturing recombinant protein refractile bodies. See, e.g., U.S. Pat. No. 4,511,502.

In one variation of this embodiment, the heregulin variant is purified (1) to a degree sufficient too obtain at least 15 residues, and preferably 20 residues, of N-terminal or internal amino acid sequence, using a spinning cup sequenator, or (2) to homogeneity by SDS-PAGE under non-reducing or reducing conditions using Coomassie blue stain. As used herein, "homogeneity" means less than about 5% contamination with other source proteins, as determined by staining with Coomassie blue.

Utility of Heregulin Variants

Generally speaking, heregulin variants according to the invention can be used in the same applications as native heregulins. Of course, some heregulin variants within the scope of the invention may be better suited for one application than for other applications. However, those skilled in the art can readily ascertain which heregulin variants are appropriate for a given application by using one or more conventional assays to determine the biological activity of the variants.

Pharmaceutical Compositions and Treatment Methods

Heregulins are useful in treating a wide range of diseases and disorders affecting the nervous system, musculature, and epithelia. In addition, heregulins can be used in the treatment of cancer. As used herein, "treatment" encompasses the treatment of an existing disease or disorder as well as prophylactic measures.

Accordingly, the present invention provides a pharmaceutical composition including a heregulin variant that is useful in treating any of a variety of diseases or disorders. In one embodiment, a pharmaceutical heregulin variant composition is employed to treat a mammal. In particular, the composition is useful for treating humans, farm animals (e.g., cows and sheep), zoo animals, animals used in sports (e.g., horses), and pets (e.g., dogs and cats). In a variation of this embodiment, the composition is used to treat a human patient.

A heregulin variant according to the invention can be useful in promoting the development, maintenance, and/or regeneration of a neuron in vivo. Neurons that respond to such a variant include central nervous system (brain and spinal chord) neurons, peripheral nervous system neurons (including sympathetic, parasympathetic, sensory, and enteric neurons), and motorneurons. Diseases or disorders amenable to heregulin variant treatment arise in individuals who have suffered nervous system damage due, for example, to trauma, surgery, stroke, ischemia, infection, metabolic disease, nutritional deficiency, malignancy, or a toxic agent.

A heregulin variant can provide therapeutic benefits to such individuals by promoting the survival, proliferation, or differentiation of neurons. For example, a heregulin variant can be used to promote the survival or proliferation of motorneurons that have been damaged by trauma or surgery. A heregulin variant can also be employed to treat motoneuron disorders, such as amyotrophic lateral sclerosis (Lou Gehrig's disease), Bell's palsy, and various conditions involving spinal muscular atrophy or paralysis. In addition, a heregulin variant can also be useful for treating a human neurodegenerative disorder, such as Alzheimer's disease, Parkinson's disease, epilepsy, multiple sclerosis, Huntington's chorea, Down's Syndrome, nerve deafness, and Meniere's disease.

Furthermore, a heregulin variant of the invention can be used to treat neuropathy, especially peripheral neuropathy. As used herein, the term "peripheral neuropathy" refers to a disorder affecting the peripheral nervous system, most often manifested as one or a combination of motor, sensory, sensorimotor, or autonomic neural dysfunctions. Examples include, but are not limited to, distal sensorimotor neuropathy and autonomic neuropathies, such as reduced motility of the gastrointestinal tract or atony of the urinary bladder. Peripheral neuropathies amendable to heregulin variant treatment can be inherited, can result from a systemic disease, or can be induced by a toxic agent. Examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome. Examples of neuropathies associated with systemic disease include post-polio syndrome, and examples of neuropathies induced by a toxic agent include those caused by treatment with a chemotherapeutic agent.

A heregulin variant can also be employed to improve neural function. The beneficial effects of heregulin variant treatment are attributed to induction of the formation of ion channels in cell membranes and enhancement of the formation of synaptic junctions.

A heregulin variant according to the invention can also be used to treat muscle cells and medical conditions affecting muscle cells. In particular, such heregulin variant can be useful for treating muscle damage, decreasing atrophy of muscle cells, and increasing muscle cell survival, proliferation and/or regeneration. Examples of pathophysiological conditions of the musculature amenable to treatment with a heregulin variant include skeletal muscle diseases (e.g., myopathy or dystrophy), cardiac muscle disorders (including atrial cardiac arrhythmias, cardiomyopathy, ischemic damage, congenital disease, and cardiac trauma), and smooth muscle disorders (such as arterial sclerosis, vascular lesion, or congenital vascular disease). A heregulin variant can also be employed to reduce hypertension and to increase functional acetylcholine receptors on muscle cells (e.g., in individuals having myasthenia gravis or tachycardia).

A heregulin variant of the invention can also enhance repair and/or regeneration of tissues that express ErbB receptors, especially ErbB-2 and either ErbB-3 or ErbB-4 receptors. Accordingly, a heregulin variant can be useful for treating dermal wounds, gastrointestinal disease, Barrett's esophagus, cystic or non-cystic end stage kidney disease, or inflammatory bowel disease. A heregulin variant can also be employed to promote reepithelialization in the human gastrointestinal, respiratory, reproductive, or urinary tract.

In addition, a heregulin variant according to the invention can be useful for inhibiting tumor cell invasion and metastasis. In particular, a tumor characterized by reduced endogenous heregulin levels (Park et al., *Proc. Am. Assoc. Cancer Res.* 34:521 [1993]) is responsive to treatment with a heregulin variant of the intention. Additionally, a tumor that overexpresses ErbB receptors can be treated by using a heregulin variant conjugated to a cytotoxic agent (described above) to direct the cytotoxic agent to the tumor tissue. A heregulin variant-enzyme conjugate can also be employed to target a prodrug (described above) therapy to cells expressing ErbB receptors.

A pharmaceutical composition according to the invention is prepared for storage by mixing a heregulin variant having the desired degree of purity with an optional physiologically acceptable carrier, excipient, or stabilizer, such as are described in *Remington's Pharmaceutical Sciences* 16th Edition (Osol ed., 1980). The composition can be stored in the form of a lyophilized cake or an aqueous solution. A pharmaceutically acceptable carrier, excipient, or stabilizer is nontoxic to recipients at the dosages employed, and can include a buffer (such as a phosphate buffer, citrate buffer, and buffers made from other organic acids), an antioxidant (e.g., ascorbic acid), a low-molecular weight (less than about 10 residues) polypeptide, a protein (such as serum albumin, gelatin, and an immunoglobulin), a hydrophilic polymer (such as polyvinylpyrrolidone), an amino acid (such as glycine, glutamine, asparagine, arginine, and lysine), a monosaccharide, a disaccharide, and other carbohydrates (including glucose, mannose, and dextrins), a chelating agent (e.g., ethylenediaminetetratacetic acid [EDTA]), a sugar alcohol (such as mannitol and sorbitol), a salt-forming counterion (e.g., sodium), and/or a nonionic surfactant (such as Tween™, Pluronics™, and PEG). In one embodiment, the physiologically acceptable carrier is an aqueous pH-buffered solution.

A heregulin variant composition intended for in vivo administration is typically sterile. Sterilization is readily accomplished by filtration through a sterile filtration membrane. If the composition is stored in lyophilized form, the composition can be filtered before or after lyophilization and reconstitution.

A pharmaceutical heregulin variant composition of the invention is generally placed into a container having a sterile access port, such as, for example, an intravenous solution bag or a vial having a stopper pierceable by a hypodermic injection needle.

Methods for administering a pharmaceutical heregulin variant composition do not differ from known methods for administering therapeutic proteins. Suitable routes of administration include, for example, intravenous, intraperitoneal, intracerebral, intramuscular, intraocular, intraarterial, or intralesional routes. A pharmaceutical heregulin variant composition can be administered continuously by infusion or by bolus injection.

If desired, a sustained-release preparation can also be used to administer a heregulin variant. An exemplary sustained-release preparation has a semipermeable matrix of a solid hydrophobic polymer to which the heregulin variant is attached. Examples of suitable polymers include a polyester, a hydrogel, a polylactide, a copolymer of L-glutamic acid and γ-ethyl-L-glutamate, non-degradable ethylene-vinyl acetate, a degradable lactic acid-glycolic acid copolymer, and poly-D-(−)-3-hydroxybutyric acid. Such matrices are in the form of shaped articles, such as films, or microcapsules.

In one embodiment, a sustained-release heregulin variant preparation includes a liposomally entrapped heregulin variant. Liposomes are small vesicles composed of various types of lipids, phospholipids, and/or surfactants. These components are typically arranged in a bilayer formation, similar to the lipid arrangement of biological membranes. Liposomes containing heregulin variants are prepared by known methods, such as, for example, those described in Epstein et al., *PNAS USA* 82:3688-92 (1985), and Hwang et al., *PNAS USA* 77:4030-34 (1980). Ordinarily the liposomes in such preparations are of the small (about 200-800 Angstroms) unilamellar type in which the lipid content is greater than about 30 mol. percent cholesterol, the specific percentage being adjusted to provide the optimal therapy. Useful liposomes can be generated by the reverse-phase evaporation method, using a lipid composition including, for example, phosphatidylcholine, cholesterol, and PEG-derivatized phosphatidylethanolamine (PEG-PE). Liposomes are extruded through filters of defined pore size to yield liposomes with the desired diameter.

For treatment of neurologic diseases or disorders, a heregulin variant can be adsorbed onto a membrane, such as a silastic membrane, which can be implanted in proximity to damaged neural tissue, as described in WO 91/04014.

The dosage of a heregulin variant composition to be employed therapeutically depends, for example, upon the therapeutic objectives, the route of administration, and the condition of the patient. Accordingly, it is necessary for the clinician to titer the dosage and modify the route of administration as required to obtain the optimal therapeutic effect. A typical daily dosage can range from about 1 μg/kg to up to 100 mg/kg of body weight or more per day, but is typically between about 10 μg/kg/day to 10 mg/kg/day. Generally, the clinician begins with a low dosage of a pharmaceutical heregulin variant composition and increases the dosage until the desired therapeutic effect is achieved.

The administration of a heregulin variant of the invention can be combined with other therapeutic regimens. For the treatment of neurological conditions, a heregulin variant is optionally combined, or administered in concert, with another neurotrophic factor to achieve a desired therapeutic effect. For example, a heregulin variant can be used together with nerve growth factor (NGF), a neurotrophin (e.g., NT-3, -4, or -5), bone-derived nerve factor (BDNF), an insulin-like growth factor (e.g., IGF-1 or IGF-2), gas6, or another neurotrophic factor to achieve a synergistic stimulatory effect on neurons. Suitable dosages for the neurotrophic factors do not differ from those known in the art for such molecules.

For the treatment of cancer, radiation and/or a chemotherapeutic agent can be administered concomitantly with a heregulin variant. Suitable preparation and dosing schedules for such chemotherapeutic agents are as recommended by the manufacturer or as determined empirically by the clinician. For preparation and dosing schedules for standard chemotherapeutic agents, see *Chemotherapy Service* (Perry ed., Williams & Wilkins 1992). Administration of the chemotherapeutic agent can precede, or follow, administration of the heregulin variant, or the chemotherapeutic agent can be given simultaneously therewith. Antibodies against tumor-associated antigens, such as antibodies that bind EGFR, ErbB-2, ErbB-3, or ErbB-4 receptor, or vascular endothelial factor (VEGF) can also be co-administered with an heregulin variant, as can one or more cytokines.

Non-Therapeutic Methods

Heregulin variants according to the invention also be employed in a variety of non-therapeutic applications, such as cell culture methods and diagnostic methods. For example, a heregulin variant can be used to promote the ex vivo survival, proliferation, or differentiation of cells, such as glial, Schwann, and muscle cells. Cultures of such cells are useful for producing cell-specific factors, such as, for example, the nerve growth factor receptor ($P75^{NGFR}$) which is a Schwann cell-specific factor. Cell-specific factors can be employed directly as diagnostic tools or employed to generate antibodies for diagnostic use.

Ex vivo cell cultures can also be used as cellular prostheses for transplantation. For example, Schwann cell cultures can be transplanted into areas of damaged spinal cord to promote regeneration of interrupted central axons or can be used to assist the repair of peripheral nerve injuries.

Accordingly, the present invention provides a cell culture method in which heregulin-responsive cells are provided in a suitable cell culture medium. Suitable tissue culture media are well known to those skilled in the art and include, but are not limited to, Minimal Essential Medium (MEM), RPMI-1640, and Dulbecco's Modified Eagle's Medium (DMEM). These tissue culture media are commercially available from Sigma Chemical Company (St. Louis, Mo., and GIBCO (Grand Island, N.Y.). The cells are cultured in the cell culture medium under conditions that permit the cells to grow in the presence of a heregulin variant. Suitable procedures for cell culture do not differ from known procedures and include, for example, liquid culture, culture in agar, and culture in a clot.

The cells are cultured in the presence of an effective amount of a heregulin variant. The amount of heregulin variant can vary, depending on the cell type and cell culture conditions, but generally is in the range of about 10 ng/ml to about 1 mg/ml. An appropriate concentration for a given cell culture can readily be determined empirically by those skilled in the art.

Techniques for culturing Schwann cells ex vivo are described in Li et al. (supra), and Sklar et al. (supra) describe ex vivo culture of clonal human myoblasts. A heregulin variant of the invention can replace the other heregulin polypeptides used in these methods.

A heregulin variant can also be employed in the diagnosis of a cancer characterized by erbB (e.g., erbB2) overexpression. In a diagnostic method according to the invention, a sample is obtained from an individual and contacted with a heregulin variant under conditions that allow specific binding between the variant and any ErbB receptors present in the sample. The sample can be a tissue sample, a bodily fluid sample, or a cell. In the case of a solid tumor, a tissue sample can be taken from a surgically removed tumor and prepared for testing by conventional techniques. In the case of lymphomas and leukemias, a sample containing lymphocytes, leukemic cells, or lymph tissues is obtained. Other samples, including samples of urine, tear drops, serum, cerebrospinal fluid, feces, sputum, cell extract, and the like, can be useful for diagnosing particular tumors. As used with regard the this method, the term "specific binding" means that the heregulin variant binds an ErbB receptor with an affinity that is sufficiently high that the heregulin variant does not substantially cross-react with other components present in the sample under the suitable reaction conditions.

The amount of heregulin variant that specifically binds to the sample is determined as an indication of ErbB receptor content. For example, a tissue sample can be obtained from a primary tumor and used to prepare formalin-fixed, paraffin-embedded blocks. See Muss et al., supra; Press et al., *Cancer Research* 54:2771-77 (1994). Tissue sections are then prepared according to known techniques.

A heregulin variant is contacted with a tissue section under conditions that permit specific binding between the variant and ErbB receptors present in the section. Binding is generally detected using a label, such as a radioisotope, a fluorescent label, or an enzyme-substrate labelling system. The label can be conjugated directly to the heregulin variant, as described above.

Alternatively, the label can be bound to the heregulin variant indirectly. For example, the label can be conjugated to an anti-heregulin variant antibody or conjugated to biotin or avidin and used with an anti-heregulin variant antibody conjugated to avidin or biotin (respectively), as described generally in *Current Protocols in Immunology* (supra). Selective binding between biotin and avidin links the label to the heregulin variant.

While in vitro analysis is normally contemplated, in vivo analysis using a heregulin variant conjugated to a suitable detectable label (e.g., In for imaging) can also be performed. See, e.g., U.S. Pat. No. 4,938,594.

A diagnostic method of the invention can be used in combination with other diagnostic/prognostic evaluations such as determining lymph node status, primary tumor size, histologic grade, estrogen or progesterone status, tumor DNA content (ploidy), or cell proliferation (S-phrase fraction). See Muss et al., *New Eng. J. Med.* 330:1260-66 (1994).

A heregulin variant according to the invention is also useful as a standard in assays for heregulins (such as a radioimmunoassay, an enzyme-linked immunoassay, and a radioreceptor assay), in an affinity purification technique (e.g., for an ErbB receptor such as ErbB-3 or ErbB-4 receptor), and in a competitive receptor binding assay. A heregulin variant can also be employed as an immunogen for generating anti-heregulin variant antibodies useful in detection and/or purification of heregulin variants.

In addition to the applications discussed above, a heregulin variant that has an enhanced specificity for the ErbB-4 receptor, relative to the ErbB-3 receptor, can be used to bind and stimulate the ErbB-4 receptor preferentially over the ErbB-3 receptor. Such a variant is useful in studies designed to distinguish between the presence of ErbB-3 and ErbB-4 receptors in a sample or to determine whether particular biological actions are mediated by one or both receptors. For instance, in cell types having a relatively small number of ErbB-4 receptors and a large number of ErbB-3 receptors, in the absence of receptor-specific heregulin variants, it is difficult to identify signal transduction pathways activated by the different receptors and to link particular biological actions to one or both receptors. A variant that preferentially binds to the ErbB-4 receptor can be used to help elucidate the roles of the ErbB-3 and ErbB-4 receptors in heregulin action.

Diagnostic Kits and Articles of Manufacture

The present invention also provides kits useful in practicing the above-described methods. In one embodiment, the invention provides a diagnostic kit, i.e., a packaged combination of reagents for use in testing a sample. The components of the kit are typically provided in predetermined ratios. A kit for detecting ErbB receptors can include, for example, a heregulin variant labelled with a suitable label or a heregulin variant with a labelled reagent(s) for indirect labelling. If the label is an enzyme, the kit typically includes any substrate or cofactor required by the enzyme label. Other additives, such as stabilizers, buffers and the like, can also be included in the kit. Kit reagents can be provided as dry powders, usually lyophilized, together with excipients for preparing kit reagent solutions of the appropriate concentration. Kits also typically include instructions for carrying out the assay for which the kit is designed.

The present invention also provides an article of manufacture containing a pharmaceutical heregulin variant composition useful for the treatment of a disorder described above. The article of manufacture includes a container and a label. Suitable containers include, for example, bottles, vials, syringes, and test tubes. The container can be made from any of a variety of materials, such as glass or plastic and can have a sterile access port. The label on, or associated with, the container indicates the disorder that the composition is to be used to treat.

The article of manufacture can be a component of a kit that includes a second container including a pharmaceutically-acceptable buffer, such as phosphate-buffered saline, Ringer's solution, or dextrose solution. The kit can also include other materials that are desirable from a commercial or user standpoint, such as other buffers, diluents, filters, needles, syringes, and package inserts with instructions for use.

The following examples are offered by way of illustration and not by way of limitation. The disclosures of all citations in the specification are expressly incorporated herein by reference.

Example 1

Determination of the Heregulin-β1 Minimal EGF-Like Domain

The smallest portion of HRG-β1 EGF that provides high-affinity receptor binding in the context of phage display was determined by preparing phagemid vectors that produced HRG-β1 147-227, 147-244, 177-227, or 177-244 fused to the C-terminus of M13 pIII. These HRG-β1 EGF-like domain fragments were amplified from the vector pHL89 (which is described in Holmes, et al., *Science* 256: 1205-10 [1992]) by PCR with primers having NsiI/XbaI-containing overhangs.

These fragments were inserted into the phagemid display vector pam-g3 by restriction digest-ligation at the same sites to generate constructs pHRG1-g3 (177-227), pHRG2-g3 (177-244), pHRG4-g3 (147-227), and pHRG5-g3 (147-244). pam-g3 was a derivative of phGHam-g3, which was designed for phage display of human growth hormone (hGH) and was described in Lowman et al., *Biochemistry* 30:10832-36 (1991). pam-g3 was produced by removing the hGH gene present in phGHam-g3 and replacing this gene with a stuffer fragment, which provides space for cleavage at the restriction sites used for cloning.

pHRG1-g3 contained an Ala227Val mutation that had been introduced in generating the construct. Single-stranded uracil-containing template was produced from this construct and used in site-directed mutagenesis to restore Ala227, generating pHRG6-g3 (177-227). In each of the above-described constructs, the HRG-β1 EGF-like domain fragment was attached to residue 247 of pIII.

In an effort to determine whether the inclusion of an extended flexible linker at the junction between HRG-β1 EGF and pIII would alleviate potential pIII interference of binding to ErbB-3, two constructs having linkers at this junction were prepared from the pHRG1-g3 template. pHRG8-g3 expressed HRG-β1 177-228 attached to pIII 323 through a linker containing three consecutive CGGS (SEQ ID NO:34) repeats, and pHRG11-g3 expressed HRG-β1 177-230 attached to pIII 247 through a GGGSGGG (SEQ ID NO:35) linkage.

The HRG-β1 EGF-like domains expressed from the above-described constructs are designated herein by removing the "p" and the "-g3" that appear in the name of the construct. Thus, the HRG-β1 EGF-like domain expressed from the pHRG2-g3 construct is designated "HRG2."

The domains were displayed monovalently on phage as pIII fusion proteins, as described by Bass et al., *Proteins* 8:309-14 (1990), and then analyzed for their binding to the high-affinity ErbB-2/3 receptor-Ig fusion (ErbB-2/3-Ig) using the phage ELISA technique described by Cunningham et al., *EMBO J.* 13:2508-15 (1994), with slight modifications. To produce phage displaying the domains, mutagenesis reaction mixtures were electrotransformed into XL1-Blue™ cells (Stratagene, Inc., La Jolla, Calif.), according to the manufacturer's protocol. The transformed cells were then infected with $10^{14}$ plaque-forming units (pfu) M13K07 helper phage (Promega Corp., Madison, Wis.). Phage stocks (about $10^{14}$ phagemid/mL) were prepared by precipitating culture broths from the cells after 18-24 hours (h) of growth with 20% PEG(2000)/2.5 M NaCl, according to the method of Sambrook and Maniatis, *Molecular Cloning a Laboratory Manual Cold Spring Harbor Press* 429 (1989). The phage were resuspended in phosphate-buffered saline (PBS: 0.01 M sodium phosphate, 0.1 M NaCl, pH 7.5).

ErbB receptor-Ig fusions where prepared using vectors that expressed the extracellular domain (ECD) of the ErbB-2, ErbB-3, or ErbB-4 receptor fused to a human IgG constant domain. First, a unique MluI site was engineered into a vector expressing a human IgG heavy chair: (pDR2) at the region encoding the hinge domain of the immunoglobulin. MluI sites were also engineered into a set of ErbB expression vectors at the region encoding the ECD/transmembrane junctions of these receptors. All mutagenesis was performed according to the method of Kunkel et al., *Methods Enzymol.* 154:367-82 (1987).

The MluI sites were used to make constructs that expressed the desired ErbB receptor-Ig fusion. The fusion junctions of the various receptor fusions were as follows (in order from the N-terminus to the C-terminus): for ErbB-2, Glu646 of ErbB2 was fused to Thr-Arg-Asp-Lys-Thr (TRDKT; SEQ ID NO:36), which was fused to His224 of VH (H224$_{VH}$); for ErbB-3, Leu617 of ErbB-3 was fused to TRDKT-H224$_{VH}$; for ErbB-4, Gly640 of ErbB-4 was fused to TRDKT-H224$_{VH}$. The ErbB receptor residue numbers are indicated according to the numbering system of Plowman et al. *PNAS USA* 90:1746-50 (1993). The conserved TR sequence was derived from the MluI site, and the conserved DKT sequence was derived from a linker. The final expression constructs had a pRK-type plasmid backbone wherein eukaryotic expression was driven by a cytomegalovirus (CMV) promoter.

Receptor fusions were expressed from these constructs, purified, and allowed to form disulfide-linked dimers. Homodimeric ErbB-2, ErbB-3 and ErbB-4 receptor-Ig fusions were produced by transfecting cells with the construct encoding the appropriate receptor fusion. Heterodimeric receptor fusions were generated by co-transfecting two expression vectors encoding different receptor fusions into the same cells. The resulting secreted receptor fusions were mixtures of two types of homodimers and the expected heterodimer.

To express the receptor fusions, adherent HEK-293 cells (ATCC No. CRL1573) were transfected with the appropriate expression vector(s) using the calcium phosphate precipitation method described by Gorman et al., *DNA and Protein Eng. Tech.* 2:3-10 (1990). Serum-containing medium was replaced with serum-free medium at 15 h post-transfection, and the transfected cells were cultured serum-free for 5-7 days.

The resulting conditioned medium was harvested and passed through Protein A columns (1 mL Pharmacia HiTrap™, Piscataway, N.J.). Purified receptor fusions were eluted with 0.1 M citric acid (pH 4.2) into tubes containing 1 M Tris-HCl (pH 9.0). The eluted proteins were then dialyzed against PBS and concentrated using Centri-prep-30™ filters (Amicon, Beverly, Mass.). Glycerol was added to a final concentration of 25%, and the preparations stored at –20° C. The receptor fusion concentration was determined via a Fc-ELISA.

Microtiter plates (Nunc Maxisorp™ 96-well plates, Inter Med, Denmark) for phage ELISA were prepared as follows. The wells were precoated overnight with 0.5 µg of rabbit anti-human IgG (Fc gamma fragment-specific) antibodies (Jackson Immunoresearch, West Grove, Pa.) in 100 µL 50 mM NaCO$_3$ (pH 9.6). The wells were blocked for 30 minutes (min) with 200 µL PBS containing 0.1% bovine serum albumin (BSA) and rinsed with wash buffer (PBS containing 0.05% Tween 20™). The wells were then coated with 0.1 µg ErbB-2/3-Ig in binding buffer (PBS, 0.1% BSA, 0.05% Tween 20™) for 1 h, and washed again.

Serial dilutions of soluble ErbB-2/3-Ig (competitor) and a concentration of phage predetermined to give 60% saturation (without competitor) were added to the wells in 100 µL binding buffer. Following incubation for 2 h at room temperature, plates were washed extensively and treated with a 1:900 dilution of anti-M13 horseradish peroxidase conjugate (Pharmacia, Piscataway, N.J.) for 20 min. The amount of phage binding was determined by assaying horseradish peroxidase activity using o-phenylenediamine dihydrochloride) substrate solution (Sigma Chemical Company, St. Louis, Mo.).

EC$_{50}$ values were calculated as the concentration of soluble ErbB-2/3-Ig required to compete half of the phage off the plate.

The results are set forth in Table 3.

TABLE 3

Initial Heregulin-Phage, Variants

| Construct | Heregulin-β1 residues | Linker and pIII fusion point | ErbB-2/3-Ig EC$_{50}$ (nM)* |
|---|---|---|---|
| HRG2 | 177-244 | pIII 247 | 6.0 |
| HRG4 | 147-227 | pIII 247 | 38.0 |
| HRG5 | 147-244 | pIII 247 | 4.7 |
| HRG6 | 177-227 | pIII 247 | 40.0 |
| HRG7 | 177-228 | pIII 247 | 42.0 |
| HRG8 | 177-228 (1-52) | (GGGS)$_3$-pIII 323 | 11.0 |
| HRG11 | 177-230 | GGGSGGG-pIII 247 | 19.0 |

*Average of duplicate experiments

All phage stocks bound specifically to immobilized ErbB-2/3-Ig and could be competed off with similar EC$_{50}$ values (5-42 nM). These values were about 100-fold higher than the previously measured dissociation constant (K$_d$). Holmes, et. al., supra. However, EC$_{50}$ values obtained from phage ELISA are often higher than the true K$_d$, particularly for high-affinity interactions. This may be due to the high receptor coat concentration required to give a reasonable signal for the bound phage, a low percentage of active receptor in competitor solutions, or interference from the linkage of the protein to pIII.

In any event, the HRG-β1 147-176 did not appear to enhance the binding of phage displaying the HRG-β1 EGF-like domain to ErbB-3-Ig, whereas HRG-β1 228-244 contributed slightly to binding affinity. Thus, the minimal EGF-like domain of HRG-β1 was defined as HRG-β1 177-228.

Phage ELISA was also carried out for the constructs encoding HRG-β1 EGF-pIII fusions containing linkers inserted between HRG-β1 EGF and the pIII fragment. Mild enhancements in binding affinity were observed for the linker-containing fusions, along with increased expression of functional fusions, as determined by binding titrations of the phage stocks. The fusion of HRG-β1 EGF via a inker to pIII residue 323, instead of residue 247 (pHRG8-g3) resulted in a slight affinity enhancement. This construct was therefore used as the template vector for construction of phage display libraries.

Example 2

Identification of Active Residues in the Heregulin-β1 EGF Domain by Alanine Scanning This example describes the identification of active residues in the heregulin-β1 (HRG-β1) EGF-like domain (HRG-β1 177-229) that play a role in the binding of HRG-β1 to the ErbB-3 and ErbB-4 receptors. Active residues were identified by mutating individual amino acids in this domain to alanine. The mutated domains (hereinafter "variants") were displayed monovalently on phage as pIII fusion proteins and variant affinities for ErbB-3 and ErbB-4 were determined by phage ELISA. Selected variants were expressed as thioredoxin fusion proteins, which were also assayed for ErbB-3 and ErbB-4 affinity.

Alanine Scanning Mutagenesis and Phage Display

Alanine-substituted variants were generated by site-directed mutagenesis according to Kunkel et al., *Methods Enzy-* mol. 154:367-82 (1987) (hereinafter "Kunkel mutagenesis"), using uracil-containing single-stranded DNA template prepared from pHRG2-g3. pHRG2-g3, which is described in Example 1, expressed HRG-β1 177-244 fused to pIII 247. A series of oligonucleotides was used to generate a series of constructs that expressed a series of variants in which consecutive residues were mutated to alanine. Phage stocks were prepared from these constructs as described in Example 1, except that PEG(8000) was used to precipitate the phage. The affinities of the alanine-substituted variants for ErbB-3-Ig and ErbB-4-Ig was determined by phage ELISA as described in Example 1. The results are shown in FIG. 2, which indicates the ratio of the $EC_{50}$ for each variant compared to the $EC_{50}$ for wild-type HRG-β1 177-244, also displayed on phage. In this plot, a ratio of one indicates that there was no difference in affinity for variant binding compared to wild-type HRG-β1 177-224, and a ratio of, e.g., five indicates that the variant bound the receptor with an affinity five-fold less than that of wild-type HRG-β1 177-224.

Expression, Purification, and Assay of Soluble Alanine-Substituted Variants

A number of alanine-substituted variants were expressed in soluble form as thioredoxin (Trx) fusion proteins. To prepare suitable expression vectors, a Trx expression vector was first generated from pET23a (Novagen, Inc., Madison, Wis.). pET23a was digested with NdeI (which cuts at base 238) and HindIII (which cuts at base 173), and a fragment encoding Trx was inserted. This fragment was obtained from pTrxFus (bases 2722-3180; Invitrogen Corp., San Diego, Calif.). The NdeI site, which includes the Trx translation start site, was then destroyed by cutting with NdeI and religating with Klenow. This removed the NdeI site, while retaining the Trx translation start.

Vectors encoding HRG-β1 alanine-substituted variants were initially generated by Kunkel mutagenesis in a pRK5.gDhrgB1 vector (described in Gorman et al., *DNA Prot. Eng. Tech.* 2:2-10 [1990]). The sequences encoding the variants could be cleaved from these vectors using NdeI and BamHI. To facilitate cloning of such fragments into the Trx expression vector, Kunkel mutagenesis was used to engineer a KpnI site into the pRK5.gDhrgB1 vector encoding wild-type HRG-β1 146-244 immediately upstream of the NdeI site (at base 5407). A KpnI-BamHI fragment encoding wild-type HRG-β1 146-224 was then cleaved from pRK5.gDhrgB1 and inserted to the Trx expression vector at KpnI and BamHI cloning sites at the 3' end of the sequence encoding Trx. This introduced an NdeI site immediately downstream of the KpnI site. In the resultant vector, the wild-type HRG-β1 sequence could be removed by digesting with NdeI and BamHI and replaced with an NdeI-BamHI fragment encoding a variant. The series of Trx-variant expression vectors thus obtained expressed Trx-variant fusions that contained an enterokinase protease recognition site (DDDDK; SEQ ID NO:37) between the Trx and the variant sequences.

Expression of Trx-variant fusion proteins was driven by the inducible T7 promoter from pET23a. Cloning, cell growth, and expression were carried out as described in the Novagen pET system manual. Briefly, cloning was done in XL1-Blue™ cells (Stratagene, Inc., La Jolla, Calif.) and expression of soluble protein in BL21DE3 host cells (Novagen, Inc., Madison, Wis.). BL21DE3 cells containing a Trx-variant expression vector were grown at 37° C. in LB medium until the $OD_{550}$ reached 0.3-0.6. Expression of Trx-variant was then induced by addition of 0.4 nM isopropyl-β-D-thiogalactopyranoside (IPTG), and growth was allowed to continue for 2-4 h at 28° C. Cells were collected by centrifugation, resuspended in 0.02 M Tris-HCl, 0.025 M EDTA (pH 7.5) to a volume that was ½oth the cell culture volume.

Cells were lysed by freezing on dry ice, thawing at 37° C., followed by vigorous sonication. The freeze, thaw, and sonication cycle was repeated three times. Protein was further solubilized in 6 M GdHCl, 0.1 M Tris-HCl (pH 8.8), sulfitolized by the addition of 0.1 M $Na_2SO_3$, 0.2 M $Na_2S_4O_6$, and stirred at room temperature for 1.5 h. Protein was dialyzed into 0.05 M Tris-HCl (pH 7.5), 0.01 M methionine. After dialysis, the insoluble material was removed by centrifugation at 35K×g for 15 min.

The supernatant was purified by Fast Flow Q Sepharose™ (Pharmacia, Piscataway, N.J.) chromatography using a 15-ml column equilibrated with 0.01 M Tris-HCl (pH 7.5). Protein was eluted using a 0-2 M NaCl gradient with a flow rate of 5 mL/min. The Trx-variant fusions eluted between 0.5-0.6 M NaCl and were refolded overnight at room temperature after addition of 1 mM cysteine. The resultant preparation was dialyzed into 0.05 M Tris-HCl (pH 7.5), 0.01 M methionine. Trx-variant fusions were found to be essentially homogeneous as determined by amino acid analysis and SDS-PAGE.

The affinities of the Trx-variant fusions for ErbB receptor-Ig fusions were determined by measuring inhibition of $^{125}$I-HRG-β1 177-244 binding to ErbB-3-Ig and ErbB-4-Ig. Receptor fusions were coated on plates (Nunc Maxisorp C™ break-apart strip wells, Inter Med, Denmark) via anti-human IgG, as described in Example 1 for phage ELISA. Binding assays were carried out with a constant amount of $^{125}$I-HRG-β1 177-244 (100-300 pM) and varying concentrations (100 pM-4 µM) of unlabeled Trx-variant fusion. Following incubation for 1-3 h at room temperature, plates were washed, and the amount of bound $^{125}$I-HRG-β1 177-244 in each well was counted on a gamma counter (Isodata, ICN Biomedic Systems, Huntsville, Ala.). For the ErbB-3 binding assays, the blocking buffer was TBST (0.025 M Tris-HCl [pH 7.5], 0.15 M NaCl, 0.02% Tween 20™) containing 1% BSA; the binding buffer was RPMI 1640™ cell culture media (Gibco-BRL, Gaithersburg, Md.) containing 2 mM glutamine, 100 U/mL penicillin, 100 µg/mL streptomycin, 10 mM HEPES buffer (pH 7.2), 0.2% BSA; and the wash buffer was TBST. For the ErbB-4 binding assays, PBS containing 1% BSA was used as the blocking and binding buffers, and the wash buffer was PBS containing 0.05% Tween 20™.

The results are shown in Tables 4 and 5.

TABLE 4

$EC_{50}$ Values for Phage and Soluble Alanine-Substituted Variant Binding to the ErbB-3 Receptor

| Variant* | Phage $EC_{50}$ (nM) | Sol $EC_{50}$ (nM) |
|---|---|---|
| HRG-β1# | 13 | 9 |
| TH-WT @ | | 47.6 |
| S177 | 67 | 129 |
| H178 | >1000 | 476 |
| L179 | ~1000 | 394 |
| F189 | 892 | 975 |
| N192 | >1000 | 1642 |
| G193 | >1000 | 26.9 |
| G194 | 500 | 1212 |
| E195 | >1000 | 42 |
| V199 | 27 | |
| K200 | 20 | 45.4 |
| P205 | 22 | 39.5 |
| R207 | >1000 | 245 |
| K211 | >1000 | 248 |
| E215 | 51 | 156 |
| F216 | 500 | 2550 |
| T217 | >1000 | 145 |
| G218 | >1000 | 668 |

TABLE 4-continued

EC$_{50}$ Values for Phage and Soluble Alanine-Substituted Variant Binding to the ErbB-3 Receptor

| Variant* | Phage EC$_{50}$ (nM) | Sol EC$_{50}$ (nM) |
|---|---|---|
| R220 | >1000 | no binding |
| Y224 | 865 | 339 |
| F229 | 6 | 177 |

*Variants are identified by the HRG-β1 residues mutated to alanine.
HRG-B1 is recombinantly produced HRG-β1 177-244.
@TH-WT is thioredoxin fused at its C-terminus to wild-type HRG-β1 146-244.

TABLE 5

EC$_{50}$ Values for Phage and Soluble Alanine-Substituted Variant Binding to the ErbB-4 Receptor

| Variant* | Phage EC$_{50}$ (nM) | Sol EC$_{50}$ (nM) |
|---|---|---|
| HRG-β1# | 19 | 14.8 |
| TH-WT @ |  | 15.4 |
| S177 | 83 | 54.6 |
| H178 | 32 | 138 |
| L179 | 56 | 51.7 |
| F189 | 106 | 565 |
| N192 | 188 | 696 |
| G193 | 23 | 76.3 |
| G194 | 65 | 275 |
| E195 | 24 | 13.2 |
| V199 | 47 | 246 |
| K200 | 25 | 16.9 |
| P205 | 8 | 34.2 |
| R207 | 30 | 24.3 |
| K211 | 59 | 124 |
| E215 | 32 | 104 |
| F216 | >1000 | 173 |
| T217 | 14.2 | 32.7 |
| G218 | >1000 | 608 |
| R220 | >1000 | no binding |
| Y224 | 51 | 24.5 |
| F229 | >1000 | 89.9 |

*Variants are identified by the HRG-β1 residues mutated to alanine.
HRG-B1 is recombinantly produced HRG-β1 177-244.
@TH-WT is thioredoxin fused at its C-terminus to wild-type HRG-β1 146-244.

Example 3

Selection of Heregulin-β1 EGF Domain Variants Using Monovalent Phage Display This example describes the selection HRG-β1 variants containing residues corresponding to the minimal EGF-like domain (HRG-β1 177-228). For these variants, residue numbers also are expressed, in parentheses, in terms of the position of the residue in the minimal EGF-like domain (i.e., HRG-β1 EGF 1-52).

Variants of HRG-β1 EGF were prepared and selected for binding to ErbB-3-Ig using monovalent phage display, according to the method of Bass et al., *Proteins* 8:309-14 (1990). As discussed in detail below, an HRG-β1 EGF phagemid vector was prepared, in which HRG-β1 EGF was fused to a C-terminal fragment of the M13 coat protein pIII. Kunkel mutagenesis was performed to introduce stop codons into this vector at sites selected for randomization. This step ensures that the starting vector is incapable of expressing the wild-type polypeptide. Stretches of four to six residues per library were randomized in a linear fashion, except for the six cysteines, Phe189 (HRG-β1 EGF Phe13) and the two most C-terminal residues (see FIG. 3). Phe189 was not altered because this residue is conserved as an aromatic residue in EGF and TGF-α and forms a stacking interaction with Tyr208 (HRG-β1 EGF Tyr32) Jacobsen et al., *Biochemistry* 35:3402-17 (1996). HRG-β1 EGF was thus covered in eight libraries, designated A-E, G, H and I.

Library E, covering HRG-β1 202-209 (HRG-β1 EGF 26-33), contained a three-residue deletion. The deleted region corresponds to a disordered turn between the second and third β-sheet of HRG-β1 EGF, and the equivalent amino acids are absent in EGF and TGF-α. An HRG-β1 EGF control variant in which HRG-β1 202-204 (HRG-β1 EGF 26-28) of HRG8 are deleted (HRG63) bound ErbB-3-Ig with an affinity similar to that of wild-type (Table 13).

An additional library (F) was created to randomize a surface patch composed of side chains from the first and second β-sheets, which included HRG-β1 178, 180, 196, and 200 (HRG-β1 EGF 2, 4, 22, and 24).

The selected sites in the starting vectors were randomized be Kunkel mutagenesis to produce HRG-β1 EGF libraries. Phage displaying mutated HRG-β1 EGFs were produced from the libraries under conditions such that, statistically, each phage particle displayed no more than one copy of the mutated HRG-β1 EGF. See Bass et al., supra. These phage were then selected for binding to (sorted against) ErbB-3-Ig immobilized on an ELISA plate. Bound phage were eluted and used to reinfect host cells, which were used to produce new phage for another round of sorting. This process was repeated six to seven times for each library. Twelve clones from the phase selected from each library were then sequenced.

Construction of Phage Libraries

Phage libraries were constructed by Kunkel mutagenesis using uracil-containing single-stranded DNA template prepared from pHRG8-g3. pHRG8-g3, which is described in Example 1, expressed HRG-β1 177-228 (HRG-β1 EGF 1-52) fused via a linker to pIII residue 323. For each library, TAA and TGA stop codons were installed at positions selected for randomization to generate custom templates that eliminated wild-type background from the pools. Positions were fully randomized by mutation to NNS codons (where N is any of the four bases and S is either G or C). One oligonucleotide was used for each library mutagenesis reaction except for Library F, for which two oligonucleotides (one randomizing HRG-β1 178 and 180 [HRG-β1 EGF 2 and 4] and the other randomizing HRGβ-1 198 and 200 [HRG-β1 EGF 22 and 24]), were used simultaneously. Mutagenesis oligonucleotides contained 16-base overhangs on either side of the randomized residues.

Mutagenesis reaction mixtures were electro-transformed into XL-1 blue cells (Stratagene, Inc., La Jolla, Calif.), according to the manufacturer's protocol. The transformed cells were then infected with $10^{14}$ pfu M13K07 helper phage (Promega Corp., Madison, Wis.), and phage stocks (about $10^{14}$ phagemid/mL) were prepared as described in Example 1.

Between $1.0 \times 10^8$ and $6.4 \times 10^8$ transformants were obtained for each library, meaning that the libraries containing five or fewer randomized codons had excellent representation of the possible amino acid sequence combinations ($3.36 \times 10^7$ possible DNA sequences; $3.2 \times 10^6$ possible amino acid sequences). Library B, containing six randomized codons ($1.1 \times 10^5$ DNA sequences), had $4.8 \times 10^8$ total transformants.

Selection of Phage for ErbB-3-Ig Binding

Monovalent phage were prepared and the selection performed on ErbB-3-Ig prebound to microtiter plates via capture with polyclonal antibodies to the human Fc fragment, as described in Example 1. Approximately $10^{12}$ phage in 100 µL binding buffer (PBS, 0.1% BSA, 0.05% Tween 20™) were applied to an ErbB-3-Ig-coated well and a control well to which no ErbB-3-Ig had been added. Following a 2 h incubation at room temperature, the plates were washed extensively (12×) and phage eluted by adding 100 µL of a solution of 50 mM HCl and 0.05% Tween™ 20 and shaking for 10 min.

Eluates were neutralized with 10 µL 1 M Tris-HCl (pH 8.0) and 20 µL used for titration on log-phase XL-1 blue cells. The remainder was used to infect 1 mL of log-phase XL-1 blue cells (30 min at 37° C.), which were then superinfected with $2 \times 10^{10}$ pfu M13KO7 phage and grown in 25 mL 2YT broth (16 g/L tryptone, 10 g/L yeast extract, 5 g/L NaCl) containing 50 µg/mL carbenicillin for 18-24 h. Phage were harvested as described above and the cycle repeated. The libraries enriched rapidly, such that by round six of selection the ratio of phage eluted from positive (ErbB-3-Ig-coated) wells to negative (anti-hu Fc precoat only) wells was between 39 and 9200.

After round six (libraries A, B, D-F) or round seven (libraries C, G-I) of selection, twelve clones from each library were randomly picked and sequenced by the dideoxy method. See Sanger et al., *PNAS USA* 74:5463-67 (1977). The amino acids at the randomized positions deduced from the DNA sequences are shown in Tables 6-12 (a "." indicates a residues that is identical to the wild-type reside). The consensus selected residues at each position are displayed graphically in FIG. 3. In general, there were a large number of mutations, in some cases with dramatic changes in the character of the side chains. At several positions that sorted to a particular residue, a mixture of DNA codons was found, providing confidence that the libraries had large diversity and that selection was at the protein level. In several of the libraries, there was a spontaneous mutation of HRG-β1 Met226Ile (HRG-β1 EGF Met50Ile) due to a one-base change in this codon. This mutation results in a significant affinity enhancement for ErbB-3-Ig binding. The sequencing results for each library are summarized below.

Library A—HRG-β1 177-181 (HRG-β1 EGF 1-5)

HRG-β1 177-181 (HRG-β1 EGF 1-5) is present in the first β-strand in the wild-type N-terminal subdomain. The amino acid changes in the variants selected from this library are shown in Table 6.

TABLE 6

Library A Variants

| | Position in HRG-β1 | | | | | |
|---|---|---|---|---|---|---|
| Variant No. | 177 | 178 | 179 | 180 | 181 | |
| Wild-type | S | H | L | V | K | (SEQ ID NO:38) |
| 1 | W | R | . | . | P | (SEQ ID NO:39) |
| 2 | W | S | . | Q | P | (SEQ ID NO:40) |
| 3, 5, 10 | W | E | . | . | P | (SEQ ID NO:41) |
| 4 | W | S | . | . | . | (SEQ ID NO:42) |
| 6 | W | S | . | I | P | (SEQ ID NO:43) |

TABLE 6-continued

Library A Variants

| | Position in HRG-β1 | | | | | |
|---|---|---|---|---|---|---|
| Variant No. | 177 | 178 | 179 | 180 | 181 | |
| 7 | W | R | . | . | A | (SEQ ID NO:44) |
| 8 | W | A | . | . | P | (SEQ ID NO:45) |
| 9 | W | S | . | Q | . | (SEQ ID NO:46) |
| 11 | W | E | . | . | A | (SEQ ID NO:47) |
| 12 | W | S | . | E | P | (SEQ ID NO:48) |

Upon randomization, Ser177 (Ser1) sorted exclusively to Trp. His178 (His2) sorted to mixed hydrophilic residues, but the wild-type residue was not among them. Leu179 (Leu3) was conserved in all variants sequenced. Val180 (Val4) sorted to wild-type in eight out of 12 variants, and the remaining variants had conservative substitutions at this position, with the exception of a Val180Glu (Val4Glu) mutation. At Lys181 (Lys5), Pro appeared in eight variants, and the wild-type residue was found in two variants.

Four variants from library A did not contain amino acid substitutions at positions randomized in library A. Instead, these variants contained amino acid substitutions at positions randomized in library B, and thus these variants are listed as variants B1-B4 in Table 7. Similarly, four variants from library B did not contain amino acid substitutions at positions randomized in library B, but rather contained substitutions at positions randomized in library A. These variants are listed as variants A5-A8 in Table 6.

Library E—HRG-β1 183-188 (HRG-β1 EGF 7-12)

HRG-β1 183-188 (HRG-β1 EGF 7-12) has a helical character in the wild-type protein. The amino acid changes in the variants selected from this library are shown in Table 7.

TABLE 7

Library B Variants

| | Position in HRG-β1 | | | | | | |
|---|---|---|---|---|---|---|---|
| Variant No. | 182 | 184 | 185 | 188 | 187 | 188 | |
| Wild-type | A | E | K | E | K | T | (SEQ ID NQ:49) |
| 1* | G | V | G | R | D | G | (SEQ ID NO:50) |
| 2* | G | G | E | R | E | G | (SEQ ID NO:51) |
| 3 | G | . | E | R | E | G | (SEQ ID NO:52) |
| 4*, 5* | G | W | D | R | E | G | (SEQ ID NO:53) |
| 6* | G | V | Q | R | E | G | (SEQ ID NO:54) |
| 7 | G | . | E | R | A | G | (SEQ ID NO:55) |
| 8 | G | K | E | R | E | G | (SF2 ID NO:56) |
| 9* | T | N | S | R | E | G | (SEQ ID NO:57) |
| 10* | D | K | S | R | E | G | (SEQ ID NO:58) |
| 11* | G | . | D | R | . | Q | (SEQ ID NO:59) |
| 12 | G | R | E | R | E | G | (SEQ ID NO:60) |

*Variant also contained Met226Ile.

Randomization of this region produced the most dramatic changes from the wild-type sequence, although the generally hydrophilic character of this region was maintained in the variants sequenced. In particular, this six-residue stretch sorted to Gly residues at the first and last positions, Ala183 and Thr188 (Ala7 and Thr12). There was also a change in registry of positive and negative charges at Lys185 (Lys9), which sorted to Glu and Asp, among others; Glu186 (Glu10), which sorted exclusively to Arg; and Lys187 (Lys11), which sorted to Glu and Asp. Glu184 (Glu8) sorted to a variety of different types of residues, indicating that this side chain does not play an important role in ErbB-3 receptor binding.

Library C—HRG-β1 191-195 (HRG-β1 EGF 15-19)

HRG-β1 191-195 (HRG-β1 EGF 15-19) includes the β-turn between the helix and the second β-strand. The amino acid changes in the variants selected from this library are shown in Table 8.

TABLE 8

Library C Variants

| Variant No. | Position in HRG-β1 | | | | | |
|---|---|---|---|---|---|---|
| | 191 | 192 | 193 | 194 | 195 | |
| Wild-type | V | N | G | G | E | (SEQ ID NO:61) |
| 1, 2, 4, 5, 7-12 | . | . | . | . | . | (SEQ ID NO:62) |
| 3 | . | . | . | . | V | (SEQ ID NO:63) |
| 6 | . | . | . | . | Q | (SEQ ID NO:64) |

Randomization and selection produced variants in which the wild-type amino acid sequence in this region was almost completely conserved. Mutations were found in only two variants, both at Glu195 (Glu19). This result is consistent with an important role for the wild-type residues in this region in ErbB-3 receptor binding.

Library D—HRG-β1 197-201 (HRG-β1 EGF 21-25)

HG-β1 197-201 (HRG-β1 EGF 21-25) is present in the second β-strand in the N-terminal subdomain. The amino aced changes in the variants selected from this library are shown in Table 9.

TABLE 9

Library D Variants

| Variant No. | Position in HRG-β1 | | | | | |
|---|---|---|---|---|---|---|
| | 197 | 198 | 199 | 200 | 201 | |
| Wild-type | F | M | V | K | D | (SEQ ID NO:65) |
| 1*, 2*, 8*, 12* | Y | K | . | R | I | (SEQ ID NO:66) |
| 3 | . | R | . | . | T | (SEQ ID NO:67) |
| 4, 5, 7, 9 | Y | R | . | . | T | (SEQ ID NO:68) |
| 6 | Y | . | I | . | Y | (SEQ ID NO:69) |
| 10 | Y | . | . | . | T | (SEQ ID NO:70) |
| 11 | M | R | . | R | T | (SEQ ID NO:71) |

*Variant also contained Met226Ile.

Randomization in this region yielded either a gain or loss of charge for two of the five residues. Phe197 (Phe21) sorted to Tyr in 10 out of 12 variants, maintaining aromaticity at this position. Met198 (Met22) sorted to a positively charged residue in 11 out of 12 variants. Val199 (Val23) was conserved in all variants, and Lys200 (Lys24) sorted either to wild-type or to Arg, retaining the positive charge at this position. Asp201 (Asp25) sorted to uncharged residues Thr or Ile, retaining the β-branch character of this position. Variants D1, D2, D8, D12 also included the spontaneous affinity-enhancing Met226Ile (Met50Ile) mutation.

Library E—HRG-β1 205-209 (HRG-β1 EGF 29-33)

HRG-β1 205-209 (HRG-β1 EGF 29-33) includes residues present in the third β-strand in the N-terminal subdomain. The amino acid changes in the variants selected from this library are shown in Table 10.

TABLE 10

Library E Variants

| Variant No. | Position in HRG-β1 | | | | | |
|---|---|---|---|---|---|---|
| | 205 | 206 | 207 | 208 | 209 | |
| Wild-type | P | S | R | Y | L | (SEQ ID NO:72) |
| 1 | T | P | Y | L | M | (SEQ ID NO:73) |
| 2, 4 | Y | G | Y | L | M | (SEQ ID NO:74) |
| 3* | Y | R | Y | R | M | (SEQ ID NQ:75) |
| 5, 12 | T | H | Y | R | G | (SEQ ID NO;76) |
| 6 | T | H | Y | R | M | (SEQ ID NO:77) |
| 7* | Y | K | Y | R | M | (SEQ ID NO:78) |
| 8, 9 | T | K | Y | R | G | (SEQ ID NO:79) |
| 10 | Y | K | Y | R | . | (SEQ ID NO:80) |
| 11# | | | | | | |

*Variant also contained Met226Ile.
Variant E11 was a contaminant from library F (identical to the other 12 library F variants)

Upon randomization, Pro205 (Pro29) sorted to Thr or Tyr. Ser206 (Ser30) sorted to mixed residues, predominantly those having basic side chains, although Gly also appears twice (in sequences derived from the same variant). An inversion of side chains occurred for Arg207 (Arg31) and Tyr208 (Tyr32), the first of which sorted exclusively to Tyr and the second of which sorted primarily to Arg (seven variants) and Leu (four variants). This finding was particularly unexpected, given that Tyr208 stacks with Phe189 (Phe13) in the structure and is conserved in the EGF sequence. See Jacobsen et al., *Biochemistry* 35:3402-17 (1996). At Leu209 (Leu33), the relatively conservative Met substitution was found in the majority of variants, but Gly was also found.

Library G—HRG-β1 211-216 (HRG-β1 EGF 35-40)

HRG-β1 211-216 (HRG-β1 EGF 35-40) includes the first β-strand of the C-terminal subdomain of HRG-β1 EGF. The amino acid changes in the variants selected from this library are shown in Table 11.

TABLE 11

Library G Variants

| | Position in HRG-β1 | | | | | | |
|---|---|---|---|---|---|---|---|
| Variant No. | 211 | 212 | 213 | 214 | 215 | 216 | |
| Wild-type | K | C | P | N | E | F | (SEQ ID NO:81) |
| 1, 5, 6, 10, 12 | R | . | S | L | . | . | (SEQ ID NO:82) |
| 2 | R | . | S | E | . | . | (SEQ ID NO:83) |
| 3 | . | . | . | K | . | M | (SEQ ID NO:84) |
| 4 | R | . | T | V | . | Y | (SEQ ID NO:85) |
| 7, 8 | R | . | T | V | . | Y | (SEQ ID NO:86) |
| 9 | . | . | N | S | . | . | (SEQ ID NO:87) |
| 11 | R | . | K | K | . | . | (SEQ ID NO:88) |

Upon randomization, 10 out of 12 variants contained a Lys211Arg (Lys35Arg) mutation, thus retaining a positive charge at this position, which lies between two cysteines. Pro213 (Pro37) sorted to mixed hydrophilic residues, and Asn214 (Asn38) sorted to a mixture of residues, with Leu and Val appearing most frequently. Glu215 (Glu39) was conserved in all variants, and Phe216 (Phe40) was retained in eight out of 12 variants with a conservative Tyr substitution in three of the remaining variants.

Library H—HRG-β1 217-220 (HRG-β1 41-44)

The HRG-β1 217-220 (HRG-β1 EGF 41-44) library proved vulnerable to contamination by a high-affinity variant from library B (variant B5). This variant was found in 11 out of 12 variants. In the single unaffected variant, the wild-type amino acid sequence was conserved except for an Asp219Glu (Asp43Glu) mutation. This result suggests that this region requires the wild-type or similar sequences for optimal binding.

Library I HRG-β1 222-226 (HRG-β1 EGF 46-50)

HRG-β1 222-226 (HRG-β1 EGF 46-50) includes a short strand of β-sheet that aligns with the strand of β-sheet at HRG-β1 213-216 (HRG-β1 EGF 38-40). The amino acid chances in the variants selected from this library are shown in Table 12.

TABLE 12

Library I Variants

| | Position in HRG-β1 | | | | | |
|---|---|---|---|---|---|---|
| Variant No. | 222 | 223 | 224 | 225 | 226 | |
| Wild-type | Q | N | Y | V | M | (SEQ ID NO:89) |
| 1, 4, 8 | . | W | . | . | I | (SEQ ID NO:90) |
| 2, 3, 5-7, 9-12 | . | H | . | . | I | (SEQ ID NO:91) |

Upon randomization of HRG-β1 222-226, only two types of variants were found in the 12 sequenced, both having wild-type residues conserved at Gln222 (Gln46), Tyr224 (Tyr48), and Val225 (Val49), and both having a Met226Ile (Met50Ile) mutation. Asn223 (Asn47) sorted to His (nine variants) or Trp (three variants). The strong affinity-enhancing effect of Met226Ile is evidenced by its presence in all variants sequenced from this library and a high frequency of occurrence in variants from several other libraries.

Library F—HRG-β1 178, 180, 198, and 200 (HRG-β1 EGF 2, 4, 22 and 24)

When His178 (His2), Val160 (Val4), Met196 (Met22), and Lys200 (Lys24) were simultaneously randomized, only one type of variant was found. His176, Val180, and Lys200 sorted to wild-type residues, and Met198 sorted to Lys. These variants additionally contained the spontaneous Met226Ile (Met50Ile) mutation, which gave the variants a significant selective advantage over other sequences. It is striking that the wild-type His was found at position 178 because none of the 12 variants sequenced from library A contained His178.

Conservation of HRG-β1 EGF Residues in Phage Display and Alanine Scanning Results Positions where alanine substitution strongly affected binding affinity tended to sort to the wild-type residue. See, for example, the data for positions at the junction between the N- and C-terminal subdomains, (i.e., the β-turn at HRG-β1 191-195 [HRG-β1 EGF 15-19] and the loop at HRG-β1 217-220 [HRG-β1 EGF 41-44]) Additionally, positions where alanine substitution produced less significant effects tended to undergo substantial mutation upon phage display, as seen for the helical stretch at HRG-β1 183-188 (HRG-β1 EGF 7-12).

Analysis of the Impact of Selected Mutations on Receptor Affinity and Specificity Individual variants from each library were chosen for phage production and further characterization of the mutated HRG-β1 EGFs ("variants") displayed on the phage. The choice of variants for further characterization was based on selection frequency, with a bias towards sequences not containing the advantageous Met226Ile (Met50Ile) substitution. In addition, phagemid vectors for use in producing phage displaying mutated HRG-β1 EGFs containing various combinations of the above mutations ("combination variants") were prepared by Kunkel mutagenesis, using templates prepared from several of the above-described variants. The amino acid substitutions in the combination variants are indicated in FIG. 4. The affinities of the variants and combination variants for binding to ErbB-3-Ig (relative to the affinity of wild-type HRG-β1 EGF) were determined by phage ELISA, as described in Example 1. The results are shown in Table 13. Some of the variants and combination variants were also tested for relative ErbB-4-Ig affinity to assess specificity.

TABLE 13

Affinities of Heregulin-β1 EGF Variants and Combination Variants for ErbB-3-Ig and ErbB-4-Ig as Determined by Phage ELISA

| Construct | Phage ErbB-3 $EC_{50}$ (wt)/$EC_{50}$ (mut)* | Phage ErbB-4 $EC_{50}$ (wt)/$EC_{50}$ (mut) |
|---|---|---|
| HRG8 | 1 | 1 |
| HRG63 | 1.1 ± 0.8 | |
| A1 | 0.55 ± 0.27 | |
| A2 | 0.87 ± 0.5 | |
| A3 | 0.96 ± 0.43 | 1.1 ± 0.4 |
| A4 | <0.3 | |
| B3 | 4.7 ± 0.77 | 1.7 ± 0.5 |
| B5 | 26 ± 20 | |
| B10 | 9.3 | |
| D1 | 11 ± 0.45 | |
| D4 | 2.9 ± 1.1 | 5.0 ± 3.7 |
| D10 | 2.1 | |
| E2 | 28 ± 13 | 7.6 |
| E3 | 16 | |
| E6 | 6.6 ± 3.0 | |
| E8 | 17 ± 2.3 | |
| G1 | 1.2 ± 0.36 | 1.6 |

TABLE 13-continued

Affinities of Heregulin-β1 EGF Variants and Combination Variants for ErbB-3-Ig and ErbB-4-Ig as Determined by Phage ELISA

| Construct | Phage ErbB-3 $EC_{50}$ (wt)/$EC_{50}$ (mut)* | Phage ErbB-4 $EC_{50}$ (wt)/$EC_{50}$ (mut) |
|---|---|---|
| G4 | 0.86 ± 0.19 | |
| H5 | 1.5 | |
| I1 | 13 ± 11 | |
| I2 | 20 ± 20 | 10 |
| F1 | 4.4 ± 3.3 | |
| HRG90 | 6.3 ± 3.1 | |
| HRG37 | 13 ± 15 | |
| HRG38 | <0.3 | |
| HRG40 | <0.3 | |
| HRG41 | <0.3 | |
| HRG48 | 49 ± 15 | |
| HRG53 | 26 ± 16 | |
| HRG54 | 12 ± 9.2 | |
| HRG55 | 13 ± 11 | |
| HRG56 | 31 ± 22 | |
| HRG57 | 24 ± 16 | |
| HRG58 | 58 ± 11 | 44 |
| HRG59 | 26 ± 14 | |
| HRG60 | 63 ± 11 | |
| HRG61 | 29 ± 25 | |
| HRG62 | 32 ± 14 | |
| HRG71 | 79 ± 56 | |
| HRG73 | 56 ± 6.6 | 16 |

*Based on the wild-type HRG-β1 EGF-phage $EC_{50}$ (=135 ± 104 nM for ErbB-3-Ig, 163 ± 112 nM for ErbB-4-Ig) determined on during the same assay run.
Shown are standard deviations for averages of 2-4 duplicate runs, or the average only for assays performed in duplicate for one run.

Variants from library A had $EC_{50}$ values very similar to wild-type HRG-β1 EGF. Variants from libraries B and D had significantly enhanced affinity for ErbB-3-Ig and ErbB-4-Ig, in the range of three to five times the wild-type affinity for selected variants not containing Met226Ile (Met50Ile). (See variants B3 and D4.) Substantially greater enhancements in affinity (up to 26-fold wild-type HRG-β1 EGF) were measured for variants that contained Met226Ile (Met50Ile). (See variants B5, B10, and D1).

Variants from library E showed even greater affinity enhancements. For example, variant E2, which differed from the library consensus sequence (FIG. 3) at HRG-β1 206 and 208 (HRG-β1 EGF 30 and 32), had an affinity enhancement of 28-fold. The effects appear to be associated with the amino acid substitutions at HRG-β1 205-209 (HRG-β1 EGF 29-33) rather than the adjacent three-residue deletion, since the affinity for ErbB-3-Ig of a Δ202-204 (Δ26-28) control variant (HRG63) was similar to that of wild-type HRG-β1 EGF (Table 13).

The single variant from library F, having Met196Lys (Met22Lys, and Met226Ile (Met50Ile) substitutions, showed an enhancement only slightly above that for Met226Ile alone, indicating a small effect attributable to the Met198Lys mutation. Variants from library G showed little, if any, ErbB-3-Ig affinity enhancement. The single Asp219Glu (Asp43Glu) mutation from the lone library H variant provided a modest increase in affinity. The two library I variants had significant enhancements in affinity for ErbB-3-Ig and ErbB-4-Ig. The enhancements were attributable to an approximately six-fold effect from the Met226Ile (Met50Ile) mutation (see variant HRG90), and an additional enhancement of about two- to three-fold from Asn223 (Asn47) to Trp or His mutations.

Phage displaying combination variants containing variant A3 mutations performed poorly. The A3-B3 combination had an $EC_{50}$ for ErbB-3-Ig similar to that of variant B3, but the other combinations tested did not bind with detectable affinity. This could be due to a disadvantageous interaction of the Ser177Trp, His178Glu, or Lys181Pro (Ser1Trp, His2Glu, or Lys5Pro) mutations with mutations from the other libraries. The combination of the B3 and E2 mutations yielded slightly diminished affinities relative to that of variant E2.

The combination of mutations from variants from the other libraries gave closer to additive behavior and resulted in the enhancement of $EC_{50}$ values by greater than 50-fold. The $EC_{50}$ values for the best combination variants were close to the lower limit of the assay at the receptor coating concentration used (approximately 4 nM). Using lower levels of receptor coat yielded sub-nanomolar $EC_{50}$ values for these combination variants, but did not allow measurement of wild-type affinity, due to minimal binding of wild-type HRG-β1 EGF phage. The best combination variants contained the D4 sequence, either the B3 or E2 sequence, and either the single Met50Ile mutation or the I2 sequence.

In general, variants that exhibited enhancements in affinity for ErbB-3-Ig also exhibited similar enhancements in affinity for ErbB-4-Ig.

Expression, Purification, and Assay of Soluble HRG-β1 EGF Variants

A number of variants were expressed in soluble form (i.e., mutated HRG-β1 EGFs were expressed free of M13 pIII). To facilitate periplasmic expression of soluble variants, TAG codons were installed following HRG-β1 226 (HRG-β1 EGF 52) in the corresponding phagemids by Kunkel mutagenesis, and the resulting constructs were transformed into 34B8 cells (genotype: tonAΔ phoAΔE15 Δ(argF-lac) 169 deoC2 ompTΔ degP41 (ΔPstI-kanR)). The constructs included those for expressing variants A3, E2, and F1) and combination variants HRG58 (D4+E2+M50I) and HRG73 (B3+D4+E2+I2), as well as the construct that expressed wild-type HRG-β1 EGF (HRG8).

Expression at levels of about 1 mg/L was achieved as follows. Cell cultures were grown to a density of $OD_{550}$=1.0 in LB medium containing 50 μg/mL carbenicillin and used to inoculate modified AP5 medium at a 1/100 dilution. (Modified AP5 medium contained: 1.5 g/L glucose, 11 g/L Hycase SF, 0.6 g/L yeast extract, 0.19 g/L anhydrous $MgSO_4$ or 0.394 g/L $MgSO_4$*$7H_2O$, 1.07 g/L ammonium chloride, 3.73 g/L KCl, 1.2 g/L NaCl, 120 mL/L 1 M triethanol-amine [pH 7.4].)

Wild-type HRG-β1 EGF and variants thereof were purified to homogeneity from periplasmic shockates in a single reverse-phase HPLC step. Briefly, cells were harvested after 24 h of growth at 30° C. ($OD_{550}$=1.2) by centrifugation at 4500 rpm, and the pellets were frozen in ethanol/dry ice for 2 h. Following resuspension and thawing in 5 mM $MgCl_2$, 75 mM $CaCl_2$, 1 mM phenyl methyl sulfonyl fluoride, and 10 mM Tris-HCl (pH 7.6), shocked cells were removed by centrifugation, leaving shockates. Shockates were filtered and chromatographed by semipreparative C18 reverse-phase HPLC using a gradient from 0-40% acetonitrile over 80 min, with a flow rate of 3 mL/min. Fractions shown by electrospray mass spectrometry to contain HRG-β1 EGF (or variants thereof) were lyophilized and resuspended in 1 mM EDTA, 10 mM Tris-HCl (pH 7.6). Proteins were found to be essentially homogeneous as determined by amino acid analysis and SDS-PAGE.

The affinities of the soluble variants for ErbB-Ig were determined by measuring inhibition of $^{125}$I-HRG binding to ErbB-2/3, -3 and -4 receptor-Ig fusions, as previously described in Example 1. Although the ErbB-2/3-Ig preparation also contains ErbB-2/2 and 3/3 homodimers (as a result of coexpression of ErbB-2- and -3-Ig's), the displacement of $^{125}$I-HRG should be predominantly from ErbB-2/3-Ig because of the approximately 100-fold higher affinity of wild-type HRG-β1 EGF for the 2/3-heterodimer versus the 3/3 homodimer.

The results are shown in Table 14.

TABLE 14

Binding and Activation Parameters for Soluble Heregulin-β1 EGF Variants

| Construct | ErbB-3-Ig EC$_{50}$ (nM) | ErbB-4-Ig EC$_{50}$ (nM) | ErbB-2/3-Ig EC$_{50}$ (nM) | KIRA EC$_{50}$ (nM) |
|---|---|---|---|---|
| HRG8 (WT) | 2.3 ± 0.2 | 1.5 ± 0.1 | 0.033 ± 0.003 | 0.212 |
| A3 | 4.3 ± 0.2 | 2.1 ± 0.1 | 0.067 ± 0.007 | 0.182 |
| E2 | 2.0 ± 0.2 | 2.4 ± 0.02 | 0.035 ± 0.007 | 0.092 |
| F1 | 0.60 ± 0.01 | 0.26 ± 0.011 | 0.061 ± 0.002 | 0.151 |
| HRG58 | 0.80 ± 0.01 | 0.30 ± 0.005 | 0.075 ± 0.006 | 0.129 |
| HRG73 | 2.7 ± 0.1 | 0.31 ± 0.003 | 0.20 ± 0.006 | 0.173 |

The variants showed higher affinity for ErbB-3-Ig than did wild-type HRG-β1 EGF (up to 4-fold), although the affinity enhancements were less dramatic that determined by phage ELISA. Analysis in this format also revealed that the E2 mutations confer greatly enhanced affinity, and that the additional D4 and Met50Ile mutations (in construct HRG58) do not contribute additively. As observed in the phage ELISAs, the variants showed enhancements in affinity for ErbB-4-Ig that were similar to affinity-enhancements for ErbB-3-Ig. Variant affinities for ErbB-2/3-Ig were similar to the affinity of wild-type HRG-β1 EGF for the 2/3-heterodimer, although the maximally substituted construct (HRG72) bound 6-fold more weakly to ErbB-2/3-Ig than did wild-type HRG-β1 EGF.

The soluble variants were also assayed for their ability to stimulate tyrosine phosphorylation of the ErbB-2 receptor on MCF7 breast cancer carcinoma cells. This was accomplished in a KIRA-ELISA format as described in Sadick et al., *Analyt. Biochem.* 235:207-214, in which the ErbB-2 phosphorylation detected is believed to be due primarily to the formation of ErbB-2/3 heterodimers.

Briefly, 2×10$^5$ MCF-7 cells were added to each well of a flat-bottom 96-well culture plate and cultured overnight. The following morning the culture medium was replaced with medium containing a variant or HRG8 (wild-type) at concentrations ranging from 0 to 10 nM. The cells were stimulated at 37° C. for 30 min, the culture medium was decanted. To lyse the cells and solubilize the receptors, 100 µl of lysis buffer was added to each well. Lysis buffer consisted of 150 mM NaCl, 50 mM HEPES, 0.5% Triton-X100, 0.01% thimerosol, 30 kIU/ml aprotinin (ICN Biochemicals, Aurora, Ohio), 1 mM 4-(2-aminoethyl)benzenesulfonyl fluoride hydrochloride (AEBSF; ICN Biochemicals), and 2 mM sodium orthovanadate. The plate was then agitated gently on a plate shaker (Bellco Instruments, Vineland, N.J.) for 60 min at room temperature.

While the cells were being solubilized, an ELISA microtiter plate (Nunc Maxisorp™, Inter Med, Denmark) that had been coated overnight at 4° C. with the affinity-purified polyclonal anti-ErbB-2 ECD antibody (1.0 µg/ml in 50 mM carbonate buffer (pH 9.6) was decanted, and blocked with block buffer (PBS, 0.5% BSA [Intergen Co., Purchase, N.Y.], 0.01% thimerosol) for 60 min at room temperature with gentle agitation. After 60 min, the anti-ErbB-2 ECD-antibody coated plate was washed six times with wash buffer (PBS, 0.05% Tween 20™, 0.01% thimerosol) using an automated plate washer (ScanWasher 300, Skatron Instruments, Inc., Sterling, Va.).

The lysate containing solubilized ErbB-2 from each cell-culture microtiter well was transferred to each anti-ErbB2 ECD antibody-coated and blocked ELISA well and incubated for 2 h at room temperature with gentle agitation. The unbound receptor was removed by washing with wash buffer, and 100 µl of biotinylated 4G10 (antiphosphotyrosine antibody) diluted to 0.2 µg/ml in dilution buffer (PBS, 0.5% BSA, 0.05% Tween 20™, 5 mM EDTA, 0.01% thimerosol) was added to each well. After incubation for 2 h at room temperature, the plate was washed, and 100 µl horseradish peroxidase-conjugated streptavidin (Zymed Laboratories, S. San Francisco, Calif.), diluted 1:50000 in dilution buffer, was added to each well. The plate was incubated for 30 min at room temperature with gentle agitation. The free avidin conjugate was washed away, and 100 µl freshly prepared substrate solution (tetramethyl benzidine, TMB, two-component substrate kit, Kirkegard and Perry, Gaithersburg, Md.) was added to each well. The reaction was allowed to proceed for 10 min, after which the color development was stopped by the addition on 1.0 M H$_3$PO$_4$.

The results are shown in Table 14. The EC$_{50}$ is the concentration of variant (or HRG8) required to achieve 50% maximal tyrosine phosphorylation. In general, the EC$_{50}$'s for stimulation of phosphorylation by the variants tested did not differ substantially from the EC$_{50}$ for wild-type HRG-β1 EGF. In addition, the values correlated well within the IC$_{50}$'s for binding to the receptor fusions above.

Example 4

Selection of Heregulin-β1 EGF Domain Variants for ErbB-4 Receptor Binding Using Monovalent Phage Display This example describes the selection of HRG-β1 variants for binding to the ErbB-4 receptor, and in particular, variants having a greater specificity for the ErbB-4 receptor, relative to the ErbB-3 receptor, than wild-type HRG-β1. Such variants have, for example, a lower variant:wild-type EC$_{50}$ ratio for binding to ErbB-4-Ig than for binding to ErbB-3-Ig. The variants studied contained residues corresponding to HRG-β1 177-244, which includes the minimal EGF-like domain (HRG-β1 177-226). In this example, "HRG-β1 EGF" refers to the region of the EGF-like domain extending from residues 177-244. Residue numbers are expressed in terms of position in 645-amino acid native human HRG-β1 and, in parentheses, in terms of position in HRG-β1 EGF (i.e., HRG-β1 EGF 1-68).

The variants were produced by randomization at His178, Leu179, and Arg207 (His2, Leu3, and Arg31). These residues were chosen because alanine scanning (Example 2) indicated that the substitution of alanine at these positions resulted in a significantly greater loss of affinity for the ErbB-3 receptor, as compared to the ErbB-4 receptor, suggesting that these residues may be more important for ErbB-3 receptor binding than for ErbB-4 receptor binding. Additionally, these residues are predicted to be proximal to one another on the surface of the HRG-β1 molecule, potentially forming a binding site.

Phage Library Screening for ErbB-4-Ig Binding

Variants of HRG-β1 EGF were prepared and selected for binding to ErbB-4-Ig using monovalent phage display, according to the method of Bass et al., *Proteins* 8:309-14 (1990). Briefly, the HRG-β1 EGF phagemid vector was pHRG2-p3 (described in Example 1), in which HRG-β1 177-244 was fused to a C-terminal fragment of the M13 coat protein pIII. Kunkel mutagenesis was performed to introduce stop codons into this vector at His178, Leu179, and Arg207 (His2, Leu3, and Arg31) to ensure that the starting vector could not express the wild-type polypeptide.

These sites were then randomized by Kunkel mutagenesis to produce an HRG-β1 EGF library. Phage displaying mutated HRG-β1 EGFs monovalently were produced from the library. See Bass et al., supra. These phage were then sorted against ErbB-4-Ig homodimers immobilized on an ELISA plate. Bound phage were eluted and used to reinfect host cells, which were used to produce new phage. Half of the phage from the first round of sorting was sorted against immobilized ErbB-4-Ig for three additional rounds of sorting. The other half of the phage from the first round was sorted against immobilized ErbB-4-Ig for three additional rounds in the presence of soluble ErbB-3-Ig (10 nM). Sorting the presence of soluble ErbB-3-Ig (i.e., "counter-selecting" against ErbB-3-Ig) was expected to remove variants with higher affinity for ErbB-3-Ig, allowing enrichment of those with higher affinity for ErbB-4-Ig in each round of sorting. After sorting, twelve clones from each of the two resultant libraries were sequenced.

Construction of Initial Phage Library

The initial phage library was constructed by Kunkel mutagenesis using uracil-containing single-stranded DNA template. TAA and TGA stop codons were installed at positions selected for randomization to generate a custom template that eliminated wild-type background from the pools. Positions were fully randomized by mutation to NNS codons (where N is any of the four bases and S is either G or C). Two mutagenesis oligonucleotides were used, one to randomize His178 and Leu179 (His2 and Leu3) and one to randomize Arg207 (Arg31). The oligonucleotides contained 15-base overhangs on either side of the randomized residues.

The final mutagenesis reaction mixture was electro-transformed into XL-1 blue cells (Stratagene, Inc., La Jolla, Calif.), according to the manufacturer's protocol. The transformed cells were then infected with $10^{11}$ pfu M13K07 helper phase (Promega Corp., Madison, Wis.), and phage stocks (about $10^{14}$ phagemid/mL) were prepared as described in Example 1.

At least $10^6$ transformants were obtained, indicating that the library had excellent representation of the possible amino acid sequence combinations.

Selection of Phage for ErbB-4-Ig Binding

Monovalent phage were prepared and the selection performed on ErbB-4-Ig prebound to microtiter plates via capture with polyclonal antibodies to the human Fc fragment, as described in Example 1. Approximately $10^{12}$ phage in 100 μL binding buffer (PBS, 0.1% BSA, 0.05% Tween 20™) were applied to an ErbB-4-Ig-coated well and a control well to which no ErbB-4-Ig had been added. After the first round of sorting, half of the resultant phage (hereafter the "counter-selected library") were sorted in the presence of 10 mM ErbB-3-Ig in the binding buffer. Following a 2 h incubation at room temperature, the plates were washed extensively (12×) and phage eluted by adding 100 μL of a solution of 50 mM HCl and 0.05% Tween™ 20 and shaking for 10 min.

Eluates were neutralized with 10 μL 1 M Tris-HCl (pH 8.0) and 20 μL used for titration on log-phase XL-1 blue cells. The remainder was used to infect 1 mL of log-phase XL-1 blue cells (30 min at 37° C.), which were then superinfected with $2 \times 10^{10}$ pfu M13KO7 phage and grown in 25 mL 2YT broth (16 g/L tryptone, 10 g/L yeast extract, 5 g/L NaCl) containing 50 μg/mL carbenicillin for 18-24 h. Phage were harvested as described above and the cycle repeated.

After round four of selection, twelve clones from each library were randomly picked and sequenced by the dideoxy method. See Sanger et al., PNAS USA 74:5463-67 (1977). The amino acids at the randomized positions deduced from the DNA sequences are shown in Table 15 (a "." indicates a residues that is identical to the wild-type residue).

TABLE 15

Mutations and Affinities for ErbB-3- and ErbB-4-Igs in Phage ELISA

| Wild-type | H | L | R | #Siblings[&] | ErbB-4 $EC_{50}$ Mut/WT[@] | ErbB-3 $EC_{50}$ Mut/WT |
|---|---|---|---|---|---|---|
| Four Rounds of Sorting for ErbB-4-Ig Binding (No Counter-Selection): | | | | | | |
| Clones | . | M | . | 7 | 1.5 | 1.2 |
|  | W | . | . | 2* | 1.7 | 1.2 |
|  | E | . | . | 2 | 1.7 | 9.5 |
|  | . | V | . | 1 | 1.6 | 1.5 |
| Four Rounds of Sorting for ErbB-4-Ig Binding With ErbB-3-Ig Counter-Selection: | | | | | | |
| Clones | . | . | P | 7 | 1.3 | 6.1 |
|  | L | . | . | 1* | 1.7 | 6.4 |
|  | L | . | . | 1 | 1.2 | 1.4 |
|  | D | V | . | 1 | 2.0 | 2.2 |
|  | E | V | . | 1 | 1.7 | 0.8 |
|  | T | M | . | 1 | 1.6 | 1.4 |

*HRG-β1 228-331 (HRG-β1 EGF 52-55) were spontaneously deleted and replaced by a single Met residue.
[&]Number of variants having this sequence (out of the twelve sequenced for each library).
[@]$EC_{50}$ for the variant divided by the $EC_{50}$ for wild-type HRG-β1 177-244 expressed monovalently on phage One variant predominated in each library, being represented in seven of the twelve clones sequenced from each library. The predominant variant from the library counter-selected against ErbB-3-Ig sorted back to the wild-type residue at positions His178 and Leu179 (His2 and Leu3) and had Pro at Arg207 (Arg31). The predominant variant from the library that was sorted without counter-selection sorted to wild-type at positions His175 and Arg207 (His2 and Arg31) and had Met at Leu179 (Leu3). In variants from each of the libraries, there was a spontaneous substitution of Met for HRG-β1 228-231 (HRG-β1 EGF 52-55).

Analysis of the Impact of Mutations on Receptor Affinity and Specificity

Receptor binding affinities were measured by phage ELISA for all unique variants from each library, as described in Example 1. The results are shown in Table 15. The affinities of the variants for ErbB-3-Ig and ErbB-4-Ig were determined to assess specificity.

The affinities of most variants for the ErbB receptor-Ig fusions were reduced between about 1.2-fold and 2.2-fold. Only one variant showed a slight enhancement in affinity, and only for ErbB-3-Ig. However, three variants had affinities for ErbB-4-Ig that were less than two-fold below the affinity of wild-type HRG-β1, whereas their affinities for ErbB-3-Ig were 6- to 9-fold below the affinity of wild-type HRG-β1. All of these variants sorted back to the wild-type residue at Leu179 (Leu3). One variant sorted to Glu at His178 (His2) and to wild-type at Arg207 (Arg31). Another variant sorted to wild-type at His178 (His2) and to Pro at Arg 207 (Arg31). This was the predominant variant in the counter-selected library.

The third variant sorted to Leu at His178 (His2) and to wild-type at Arg207 (Arg31) and also had the spontaneous substitution of Met for HRG-β1 228-231 (HRG-β1 EGF 52-55). The affinity of this variant for ErbB-3-Ig was reduced 6.4 fold, whereas another variant with the same sequence at His178, Leu179, and Arg207 (His2, Leu3, and Arg31), but lacking the spontaneous substitution, retained approximately wild-type affinity for ErbB-3-Ig. Thus, the reduction in affinity for ErbB-3-Ig binding is largely attributable to this spontaneous substitution. Because HRG-β1 228-231 (HRG-β1 EGF 52-55) is unlikely to be proximal to the randomized region on the surface of the HRG-β1 molecule, the data suggest that at least two distinct regions of HRG-β1 are important for ErbB receptor binding, namely residues His178, Leu179, and Arg207 (His2, Leu3, and Arg31) and HRG-β1 228-231 (HRG-β1 EGF 52-55).

Two of the three variants exhibiting enhanced specificity for ErbB-4-Ig binding accounted for eight of the twelve clones isolated from the counter-selected library. The other variant accounted for only two of the twelve clones isolated from the library that was sorted without counter-selection. Thus, counter-selection against ErbB-3-Ig produced a significant enrichment in variants exhibiting greater specificity for ErbB-4-Ig, relative to ErbB-3-Ig, than that of wild-type HRG-β1.

What is claimed is:

1. A method for binding an ErbB receptor comprising contacting a variant of a heregulin with a cell that expresses said ErbB receptor, said variant having an amino acid sequence not found in nature and the ability to bind an ErbB receptor, wherein said variant comprises a methionine residue in place of amino acid residues corresponding to residue numbers 228 to 231 of native human heregulin-β1 (SEQ ID NO: 93) numbered from the N-terminus and said heregulin variant comprises a portion that is at least 70% identical to the portion from about residue 175 to about residue 230 of native human heregulin-β1 (SEQ ID NO: 93), said heregulin variant having a greater specificity for the ErbB-4 receptor, relative to the ErbB-3 receptor, than a heregulin that differs from the heregulin variant only in that the heregulin comprises said amino acid residues corresponding to residue numbers 228 to 231 in place of said methionine.

2. The method of claim 1, wherein said cell is in cell culture.

3. The method of claim 1, wherein said cell is present in a mammal.

4. The method of claim 3, wherein said mammal is a human.

5. The method of claim 1, wherein said contacting enhances survival, proliferation, or differentiation of said cell.

6. The method of claim 5, wherein said cell is selected from a glial cell, a Schwann cell, and muscle cell.

7. The method of claim 1, wherein said heregulin variant is a variant of a human heregulin.

8. The method of claim 7, wherein said human heregulin is heregulin-β1.

9. The method of claim 1, wherein said heregulin variant is a fragment which comprises residues corresponding to a portion of human heregulin-β1 extending from about residue 175 to about residue 245.

10. The method of claim 1, wherein said heregulin variant is purified.

11. A method of determining whether a sample contains an ErbB receptor that binds a heregulin comprising:

(a) contacting a variant of a heregulin with said sample; and (b) determining whether said heregulin variant specifically binds a component of said sample as an indication of the presence of an ErbB receptor; said variant having an amino acid sequence not found in nature and the ability to bind an ErbB receptor, wherein said variant comprises a methionine residue in place of amino acid residues corresponding to residue numbers 228 to 231 of native human heregulin-β1 (SEQ ID NO: 93) numbered from the N-terminus and said heregulin variant comprises a portion that is at least 70% identical to the portion from about residue 175 to about residue 230 of native human heregulin-β1 (SEQ ID NO: 93), said heregulin variant having a greater specificity for the ErbB-4 receptor, relative to the ErbB-3 receptor, than a heregulin that differs from the heregulin variant only in that the heregulin comprises said amino acid residues corresponding to residue numbers 228 to 231 in place of said methionine.

12. The method of claim 11, wherein said heregulin variant is a variant of a human heregulin.

13. The method of claim 12, wherein said human heregulin is heregulin-β1.

14. The method of claim 11, wherein said heregulin variant is a fragment which comprises residues corresponding to a portion of human heregulin-β1 extending from about residue 175 to about residue 245.

15. The method of claim 11, wherein said heregulin variant is purified.

* * * * *

SEQUENCE LISTING

<160> NUMBER OF SEQ ID NOS: 116

<210> SEQ ID NO 1
<211> LENGTH: 71
<212> TYPE: PRT
<213> ORGANISM: Homo sapiens
<220> FEATURE:

<400> SEQUENCE: 1

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys His Leu Gly Ile Glu Phe Met Glu Ala
    50                  55                  60

Glu Glu Leu Tyr Gln Lys Arg
65                  70

<210> SEQ ID NO 2
<211> LENGTH: 66
<212> TYPE: PRT
<213> ORGANISM: Homo sapiens

<400> SEQUENCE: 2

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Asn Gln Glu Lys Ala Glu Glu Leu Tyr Gln
    50                  55                  60

Lys Arg
65

<210> SEQ ID NO 3
<211> LENGTH: 63
<212> TYPE: PRT
<213> ORGANISM: Homo sapiens

<400> SEQUENCE: 3

Ser His Leu Val Lys Cys Ala Glu Lys Glu Lys Thr Phe Cys Val Asn
1               5                   10                  15

```
Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
            35                  40                  45

Val Met Ala Ser Phe Tyr Lys Ala Glu Glu Leu Tyr Gln Lys Arg
            50                  55                  60

<210> SEQ ID NO 4
<211> LENGTH: 65
<212> TYPE: PRT
<213> ORGANISM: Homo sapiens

<400> SEQUENCE: 4

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
            35                  40                  45

Val Met Ala Ser Phe Tyr Ser Thr Ser Thr Pro Phe Leu Ser Leu Pro
            50                  55                  60

Glu
65

<210> SEQ ID NO 5
<211> LENGTH: 66
<212> TYPE: PRT
<213> ORGANISM: Rattus rattus

<400> SEQUENCE: 5

Ser His Leu Ile Lys Cys Ala Glu Lys Glu Lys Thr Phe Cys Val Asn
1               5                   10                  15

Gly Gly Glu Cys Phe Thr Val Lys Asp Leu Ser Asn Pro Ser Arg Tyr
            20                  25                  30

Leu Cys Lys Cys Gln Pro Gly Phe Thr Gly Ala Arg Cys Thr Glu Asn
            35                  40                  45

Val Pro Met Lys Val Gln Thr Gln Glu Lys Ala Glu Glu Leu Tyr Gln
            50                  55                  60

Lys Arg
65

<210> SEQ ID NO 6
<211> LENGTH: 71
<212> TYPE: PRT
<213> ORGANISM: Rattus rattus

<400> SEQUENCE: 6

Ser His Leu Ile Lys Cys Ala Glu Lys Glu Lys Thr Phe Cys Val Asn
1               5                   10                  15

Gly Gly Glu Cys Phe Thr Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
            35                  40                  45

Val Met Ala Ser Phe Tyr Lys His Leu Gly Ile Glu Phe Met Glu Ala
            50                  55                  60

Glu Glu Leu Tyr Gln Lys Arg
65                  70
```

<210> SEQ ID NO 7
<211> LENGTH: 63
<212> TYPE: PRT
<213> ORGANISM: Rattus rattus

<400> SEQUENCE: 7

Ser His Leu Ile Lys Cys Ala Glu Lys Glu Lys Thr Phe Cys Val Asn
1               5                   10                  15

Gly Gly Glu Cys Phe Thr Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln Lys Arg
    50                  55                  60

<210> SEQ ID NO 8
<211> LENGTH: 64
<212> TYPE: PRT
<213> ORGANISM: Rattus rattus

<400> SEQUENCE: 8

Ser His Leu Ile Lys Cys Ala Glu Lys Glu Lys Thr Phe Cys Val Asn
1               5                   10                  15

Gly Gly Glu Cys Phe Thr Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Phe Tyr Ser Thr Ser Thr Pro Phe Leu Ser Leu Pro Glu
    50                  55                  60

<210> SEQ ID NO 9
<211> LENGTH: 81
<212> TYPE: PRT
<213> ORGANISM: Rattus rattus

<400> SEQUENCE: 9

Ser His Leu Ile Lys Cys Ala Glu Lys Glu Lys Thr Phe Cys Val Asn
1               5                   10                  15

Gly Gly Glu Cys Phe Thr Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Phe Tyr Ser Met Thr Ser Arg Arg Lys Arg Gln Glu Thr
    50                  55                  60

Glu Lys Pro Leu Glu Arg Lys Leu Phe His Ser Leu Val Lys Glu Ser
65                  70                  75                  80

Lys

<210> SEQ ID NO 10
<211> LENGTH: 65
<212> TYPE: PRT
<213> ORGANISM: Homo sapiens

<400> SEQUENCE: 10

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr

```
                35                  40                  45
Val Met Ala Ser Phe Tyr Ser Thr Ser Thr Pro Phe Leu Ser Leu Pro
     50                  55                  60
Glu
65

<210> SEQ ID NO 11
<211> LENGTH: 65
<212> TYPE: PRT
<213> ORGANISM: Homo sapiens

<400> SEQUENCE: 11

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Ser Thr Ser Thr Pro Phe Leu Ser Leu Pro
     50                  55                  60

Glu
65

<210> SEQ ID NO 12
<211> LENGTH: 65
<212> TYPE: PRT
<213> ORGANISM: Homo sapiens

<400> SEQUENCE: 12

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Ser Thr Ser Thr Pro Phe Leu Ser Leu Pro
     50                  55                  60

Glu
65

<210> SEQ ID NO 13
<211> LENGTH: 71
<212> TYPE: PRT
<213> ORGANISM: Gallus domesticus

<400> SEQUENCE: 13

Ser His Leu Thr Lys Cys Asp Ile Lys Gln Lys Ala Phe Cys Val Asn
1               5                   10                  15

Gly Gly Glu Cys Tyr Met Val Lys Asp Leu Pro Asn Pro Pro Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys His Leu Gly Ile Glu Phe Met Glu Ala
     50                  55                  60

Glu Glu Leu Tyr Gln Lys Arg
65                  70

<210> SEQ ID NO 14
```

-continued

```
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain containing a deletion of human heregulin-beta1 residues
      202-204

<400> SEQUENCE: 14

Ser His Leu Val Lys Cys Ala Glu Lys Glu Lys Thr Phe Cys Val Asn
1               5                   10                  15

Gly Gly Glu Cys Phe Met Val Lys Asp Pro Ser Arg Tyr Leu Cys Lys
            20                  25                  30

Cys Pro Asn Glu Phe Thr Gly Asp Arg Cys Gln Asn Tyr Val Met Ala
        35                  40                  45

Ser

<210> SEQ ID NO 15
<211> LENGTH: 48
<212> TYPE: PRT
<213> ORGANISM: Homo sapiens

<400> SEQUENCE: 15

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Arg
        35                  40                  45

<210> SEQ ID NO 16
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 16

Ser His Leu Val Lys Cys Ala Glu Lys Glu Lys Thr Phe Cys Val Asn
1               5                   10                  15

Gly Gly Glu Cys Phe Met Val Lys Asp Pro Ser Arg Tyr Leu Cys Lys
            20                  25                  30

Cys Pro Asn Glu Phe Thr Gly Asp Arg Cys Gln Asn Tyr Val Ile Ala
        35                  40                  45

Ser

<210> SEQ ID NO 17
<211> LENGTH: 52
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 17

Trp Glu Leu Val Pro Cys Gly Trp Asp Arg Glu Gly Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45
```

```
Val Ile Ala Ser
    50

<210> SEQ ID NO 18
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 18

Trp Glu Leu Val Pro Cys Ala Glu Lys Glu Lys Thr Phe Cys Val Asn
1               5                   10                  15

Gly Gly Glu Cys Tyr Lys Val Arg Ile Tyr Gly Tyr Leu Met Cys Lys
            20                  25                  30

Cys Pro Asn Glu Phe Thr Gly Asp Arg Cys Gln Asn Tyr Val Ile Ala
        35                  40                  45

Ser

<210> SEQ ID NO 19
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 19

Trp Glu Leu Val Pro Cys Gly Trp Asp Arg Glu Gly Phe Cys Val Asn
1               5                   10                  15

Gly Gly Glu Cys Tyr Lys Val Arg Ile Tyr Gly Tyr Leu Met Cys Lys
            20                  25                  30

Cys Pro Asn Glu Phe Thr Gly Asp Arg Cys Gln Asn Tyr Val Ile Ala
        35                  40                  45

Ser

<210> SEQ ID NO 20
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 20

Trp Glu Leu Val Pro Cys Gly Trp Asp Arg Glu Gly Phe Cys Val Asn
1               5                   10                  15

Gly Gly Glu Cys Tyr Lys Val Arg Ile Tyr Arg Tyr Arg Met Cys Lys
            20                  25                  30

Cys Pro Asn Glu Phe Thr Gly Asp Arg Cys Gln Asn Tyr Val Ile Ala
        35                  40                  45

Ser

<210> SEQ ID NO 21
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain
```

<400> SEQUENCE: 21

Ser His Leu Val Lys Cys Ala Glu Lys Glu Thr Phe Cys Val Asn
1               5                   10                  15

Gly Gly Glu Cys Phe Met Val Lys Asp Tyr Gly Tyr Leu Met Cys Lys
            20                  25                  30

Cys Pro Asn Glu Phe Thr Gly Asp Arg Cys Gln Asn Tyr Val Ile Ala
        35                  40                  45

Ser

<210> SEQ ID NO 22
<211> LENGTH: 52
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 22

Ser His Leu Val Lys Cys Gly Glu Glu Arg Glu Gly Phe Cys Val Asn
1               5                   10                  15

Gly Gly Glu Cys Tyr Arg Val Lys Thr Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser
    50

<210> SEQ ID NO 23
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 23

Ser His Leu Val Lys Cys Gly Glu Glu Arg Glu Gly Phe Cys Val Asn
1               5                   10                  15

Gly Gly Glu Cys Phe Met Val Lys Asp Tyr Gly Tyr Leu Met Cys Lys
            20                  25                  30

Cys Pro Asn Glu Phe Thr Gly Asp Arg Cys Gln Asn Tyr Val Met Ala
        35                  40                  45

Ser

<210> SEQ ID NO 24
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 24

Ser His Leu Val Lys Cys Gly Glu Glu Arg Glu Gly Phe Cys Val Asn
1               5                   10                  15

Gly Gly Glu Cys Tyr Arg Val Lys Thr Tyr Gly Tyr Leu Met Cys Lys
            20                  25                  30

Cys Pro Asn Glu Phe Thr Gly Asp Arg Cys Gln Asn Tyr Val Met Ala
        35                  40                  45

Ser

```
<210> SEQ ID NO 25
<211> LENGTH: 52
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 25

Ser His Leu Val Lys Cys Gly Glu Arg Glu Gly Phe Cys Val Asn
 1               5                  10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Ile Ala Ser
    50

<210> SEQ ID NO 26
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 26

Ser His Leu Val Lys Cys Ala Glu Lys Glu Lys Thr Phe Cys Val Asn
 1               5                  10                  15

Gly Gly Glu Cys Tyr Arg Val Lys Thr Tyr Gly Tyr Leu Met Cys Lys
            20                  25                  30

Cys Pro Asn Glu Phe Thr Gly Asp Arg Cys Gln Asn Tyr Val Met Ala
        35                  40                  45

Ser

<210> SEQ ID NO 27
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 27

Ser His Leu Val Lys Cys Ala Glu Lys Glu Lys Thr Phe Cys Val Asn
 1               5                  10                  15

Gly Gly Glu Cys Tyr Arg Val Lys Thr Tyr Gly Tyr Leu Met Cys Lys
            20                  25                  30

Cys Pro Asn Glu Phe Thr Gly Asp Arg Cys Gln Asn Tyr Val Ile Ala
        35                  40                  45

Ser

<210> SEQ ID NO 28
<211> LENGTH: 52
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 28
```

```
Ser His Leu Val Lys Cys Ala Glu Lys Glu Lys Thr Phe Cys Val Asn
1               5                   10                  15

Gly Gly Glu Cys Tyr Arg Val Lys Thr Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Ile Ala Ser
    50

<210> SEQ ID NO 29
<211> LENGTH: 52
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 29

Ser His Leu Val Lys Cys Gly Glu Glu Arg Glu Gly Phe Cys Val Asn
1               5                   10                  15

Gly Gly Glu Cys Tyr Arg Val Lys Thr Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Ile Ala Ser
    50

<210> SEQ ID NO 30
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 30

Ser His Leu Val Lys Cys Gly Glu Glu Arg Glu Gly Phe Cys Val Asn
1               5                   10                  15

Gly Gly Glu Cys Phe Met Val Lys Asp Tyr Gly Tyr Leu Met Cys Lys
            20                  25                  30

Cys Pro Asn Glu Phe Thr Gly Asp Arg Cys Gln Asn Tyr Val Ile Ala
        35                  40                  45

Ser

<210> SEQ ID NO 31
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 31

Ser His Leu Val Lys Cys Gly Glu Glu Arg Glu Gly Phe Cys Val Asn
1               5                   10                  15

Gly Gly Glu Cys Tyr Arg Val Lys Thr Tyr Gly Tyr Leu Met Cys Lys
            20                  25                  30

Cys Pro Asn Glu Phe Thr Gly Asp Arg Cys Gln Asn Tyr Val Ile Ala
        35                  40                  45

Ser
```

```
<210> SEQ ID NO 32
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 32

Ser His Leu Val Lys Cys Ala Glu Lys Glu Lys Thr Phe Cys Val Asn
1               5                   10                  15

Gly Gly Glu Cys Tyr Arg Val Lys Thr Tyr Gly Tyr Leu Met Cys Lys
            20                  25                  30

Cys Pro Asn Glu Phe Thr Gly Asp Arg Cys Gln His Tyr Val Ile Ala
        35                  40                  45

Ser

<210> SEQ ID NO 33
<211> LENGTH: 49
<212> TYPE: PRT
<213> ORGANISM: Artificial Sequence
<220> FEATURE:
<223> OTHER INFORMATION: Variant of the human heregulin-beta1 EGF-like
      domain

<400> SEQUENCE: 33

Ser His Leu Val Lys Cys Gly Glu Glu Arg Glu Gly Phe Cys Val Asn
1               5                   10                  15

Gly Gly Glu Cys Tyr Arg Val Lys Thr Tyr Gly Tyr Leu Met Cys Lys
            20                  25                  30

Cys Pro Asn Glu Phe Thr Gly Asp Arg Cys Gln His Tyr Val Ile Ala
        35                  40                  45

Ser

<210> SEQ ID NO 34
<211> LENGTH: 4
<212> TYPE: PRT
<213> ORGANISM: Artificial Sequence
<220> FEATURE:
<223> OTHER INFORMATION: Repeat sequence in linker joining human
      heregulin-beta1 residues 177-228 to M13 pIII residue 323

<400> SEQUENCE: 34

Gly Gly Gly Ser
 1

<210> SEQ ID NO 35
<211> LENGTH: 7
<212> TYPE: PRT
<213> ORGANISM: Artificial Sequence
<220> FEATURE:
<223> OTHER INFORMATION: Linker joining human heregulin-beta1 residues
      177-230 to M13 pIII residue 247

<400> SEQUENCE: 35

Gly Gly Gly Ser Gly Gly Gly
 1               5

<210> SEQ ID NO 36
<211> LENGTH: 5
<212> TYPE: PRT
<213> ORGANISM: Artificial Sequence
<220> FEATURE:
<223> OTHER INFORMATION: Linker for ERbB-2 receptor-immunoglobulin
```

```
                             fusion proteins

<400> SEQUENCE: 36

Thr Arg Asp Lys Thr
1               5

<210> SEQ ID NO 37
<211> LENGTH: 5
<212> TYPE: PRT
<213> ORGANISM: Artificial Sequence
<220> FEATURE:
<223> OTHER INFORMATION: Enterokinase protease recognition site

<400> SEQUENCE: 37

Asp Asp Asp Asp Lys
1               5

<210> SEQ ID NO 38
<211> LENGTH: 5
<212> TYPE: PRT
<213> ORGANISM: Homo sapiens

<400> SEQUENCE: 38

Ser His Leu Val Lys
1               5

<210> SEQ ID NO 39
<211> LENGTH: 5
<212> TYPE: PRT
<213> ORGANISM: Artificial Sequence
<220> FEATURE:
<223> OTHER INFORMATION: Variant sequence at human heregulin-beta1
      residues 177-181

<400> SEQUENCE: 39

Trp Arg Leu Val Pro
1               5

<210> SEQ ID NO 40
<211> LENGTH: 5
<212> TYPE: PRT
<213> ORGANISM: Artificial Sequence
<220> FEATURE:
<223> OTHER INFORMATION: Variant sequence at human heregulin-beta1
      residues 177-181

<400> SEQUENCE: 40

Trp Ser Leu Gln Pro
1               5

<210> SEQ ID NO 41
<211> LENGTH: 5
<212> TYPE: PRT
<213> ORGANISM: Artificial Sequence
<220> FEATURE:
<223> OTHER INFORMATION: Variant sequence at human heregulin-beta1
      residues 177-181

<400> SEQUENCE: 41

Trp Glu Leu Val Pro
1               5

<210> SEQ ID NO 42
<211> LENGTH: 5
<212> TYPE: PRT
<213> ORGANISM: Artificial Sequence
<220> FEATURE:
```

-continued

<223> OTHER INFORMATION: Variant sequence at human heregulin-beta1
     residues 177-181

<400> SEQUENCE: 42

Trp Ser Leu Val Lys
1               5

<210> SEQ ID NO 43
<211> LENGTH: 5
<212> TYPE: PRT
<213> ORGANISM: Artificial Sequence
<220> FEATURE:
<223> OTHER INFORMATION: Variant sequence at human heregulin-beta1
     residues 177-181

<400> SEQUENCE: 43

Trp Ser Leu Ile Pro
1               5

<210> SEQ ID NO 44
<211> LENGTH: 5
<212> TYPE: PRT
<213> ORGANISM: Artificial Sequence
<220> FEATURE:
<223> OTHER INFORMATION: Variant sequence at human heregulin-beta1
     residues 177-181

<400> SEQUENCE: 44

Trp Arg Leu Val Ala
1               5

<210> SEQ ID NO 45
<211> LENGTH: 5
<212> TYPE: PRT
<213> ORGANISM: Artificial Sequence
<220> FEATURE:
<223> OTHER INFORMATION: Variant sequence at human heregulin-beta1
     residues 177-181

<400> SEQUENCE: 45

Trp Ala Leu Val Pro
1               5

<210> SEQ ID NO 46
<211> LENGTH: 5
<212> TYPE: PRT
<213> ORGANISM: Artificial Sequence
<220> FEATURE:
<223> OTHER INFORMATION: Variant sequence at human heregulin-beta1
     residues 177-181

<400> SEQUENCE: 46

Trp Ser Leu Gln Lys
1               5

<210> SEQ ID NO 47
<211> LENGTH: 5
<212> TYPE: PRT
<213> ORGANISM: Artificial Sequence
<220> FEATURE:
<223> OTHER INFORMATION: Variant sequence at human heregulin-beta1
     residues 177-181

<400> SEQUENCE: 47

Trp Glu Leu Val Ala
1               5

```
<210> SEQ ID NO 48
<211> LENGTH: 5
<212> TYPE: PRT
<213> ORGANISM: Artificial Sequence
<220> FEATURE:
<223> OTHER INFORMATION: Variant sequence at human heregulin-beta1
      residues 177-181

<400> SEQUENCE: 48

Trp Ser Leu Glu Pro
1               5

<210> SEQ ID NO 49
<211> LENGTH: 6
<212> TYPE: PRT
<213> ORGANISM: Homo sapiens

<400> SEQUENCE: 49

Ala Glu Lys Glu Lys Thr
1               5

<210> SEQ ID NO 50
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

<400> SEQUENCE: 50

Gly Val Gly Arg Asp Gly
1               5

<210> SEQ ID NO 51
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

<400> SEQUENCE: 51

Gly Gly Glu Arg Glu Gly
1               5

<210> SEQ ID NO 52
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

<400> SEQUENCE: 52

Gly Glu Glu Arg Glu Gly
1               5

<210> SEQ ID NO 53
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

<400> SEQUENCE: 53

Gly Trp Asp Arg Glu Gly
1               5
```

<210> SEQ ID NO 54
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

<400> SEQUENCE: 54

Gly Val Gln Arg Glu Gly
 1               5

<210> SEQ ID NO 55
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

<400> SEQUENCE: 55

Gly Glu Glu Arg Ala Gly
 1               5

<210> SEQ ID NO 56
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

<400> SEQUENCE: 56

Gly Lys Glu Arg Glu Gly
 1               5

<210> SEQ ID NO 57
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

<400> SEQUENCE: 57

Thr Asn Ser Arg Glu Gly
 1               5

<210> SEQ ID NO 58
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

<400> SEQUENCE: 58

Asp Lys Ser Arg Glu Gly
 1               5

<210> SEQ ID NO 59
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

```
<400> SEQUENCE: 59

Gly Glu Asp Arg Lys Gln
1               5

<210> SEQ ID NO 60
<211> LENGTH: 6
<212> TYPE: PRT
<213> ORGANISM: Artificial Sequence
<220> FEATURE:
<223> OTHER INFORMATION: Variant sequence at human heregulin-beta1
      residues 183-188

<400> SEQUENCE: 60

Gly Arg Glu Arg Glu Gly
1               5

<210> SEQ ID NO 61
<211> LENGTH: 5
<212> TYPE: PRT
<213> ORGANISM: Homo sapiens

<400> SEQUENCE: 61

Val Asn Gly Gly Glu
1               5

<210> SEQ ID NO 62
<211> LENGTH: 5
<212> TYPE: PRT
<213> ORGANISM: Artificial Sequence
<220> FEATURE:
<223> OTHER INFORMATION: Variant sequence at human heregulin-beta1
      residues 191-195

<400> SEQUENCE: 62

Val Asn Gly Gly Glu
1               5

<210> SEQ ID NO 63
<211> LENGTH: 5
<212> TYPE: PRT
<213> ORGANISM: Artificial Sequence
<220> FEATURE:
<223> OTHER INFORMATION: Variant sequence at human heregulin-beta1
      residues 191-195

<400> SEQUENCE: 63

Val Asn Gly Gly Val
1               5

<210> SEQ ID NO 64
<211> LENGTH: 5
<212> TYPE: PRT
<213> ORGANISM: Artificial Sequence
<220> FEATURE:
<223> OTHER INFORMATION: Variant sequence at human heregulin-beta1
      residues 191-195

<400> SEQUENCE: 64

Val Asn Gly Gly Gln
1               5

<210> SEQ ID NO 65
<211> LENGTH: 5
<212> TYPE: PRT
<213> ORGANISM: Homo sapiens
```

```
<400> SEQUENCE: 65

Phe Met Val Lys Asp
1               5

<210> SEQ ID NO 66
<211> LENGTH: 5
<212> TYPE: PRT
<213> ORGANISM: Artificial Sequence
<220> FEATURE:
<223> OTHER INFORMATION: Variant sequence at human heregulin-beta1
      residues 197-201

<400> SEQUENCE: 66

Tyr Lys Val Arg Ile
1               5

<210> SEQ ID NO 67
<211> LENGTH: 5
<212> TYPE: PRT
<213> ORGANISM: Artificial Sequence
<220> FEATURE:
<223> OTHER INFORMATION: Variant sequence at human heregulin-beta1
      residues 197-201

<400> SEQUENCE: 67

Phe Arg Val Lys Thr
1               5

<210> SEQ ID NO 68
<211> LENGTH: 5
<212> TYPE: PRT
<213> ORGANISM: Artificial Sequence
<220> FEATURE:
<223> OTHER INFORMATION: Variant sequence at human heregulin-beta1
      residues 197-201

<400> SEQUENCE: 68

Tyr Arg Val Lys Thr
1               5

<210> SEQ ID NO 69
<211> LENGTH: 5
<212> TYPE: PRT
<213> ORGANISM: Artificial Sequence
<220> FEATURE:
<223> OTHER INFORMATION: Variant sequence at human heregulin-beta1
      residues 197-201

<400> SEQUENCE: 69

Tyr Met Ile Lys Tyr
1               5

<210> SEQ ID NO 70
<211> LENGTH: 5
<212> TYPE: PRT
<213> ORGANISM: Artificial Sequence
<220> FEATURE:
<223> OTHER INFORMATION: Variant sequence at human heregulin-beta1
      residues 197-201

<400> SEQUENCE: 70

Tyr Met Val Lys Thr
1               5

<210> SEQ ID NO 71
<211> LENGTH: 5
<212> TYPE: PRT
```

```
<213> ORGANISM: Artificial Sequence
<220> FEATURE:
<223> OTHER INFORMATION: Variant sequence at human heregulin-beta1
      residues 197-201

<400> SEQUENCE: 71

Met Arg Val Arg Thr
1               5

<210> SEQ ID NO 72
<211> LENGTH: 5
<212> TYPE: PRT
<213> ORGANISM: Homo sapiens

<400> SEQUENCE: 72

Pro Ser Arg Tyr Leu
1               5

<210> SEQ ID NO 73
<211> LENGTH: 5
<212> TYPE: PRT
<213> ORGANISM: Artificial Sequence
<220> FEATURE:
<223> OTHER INFORMATION: Variant sequence at human heregulin-beta1
      residues 205-209

<400> SEQUENCE: 73

Thr Pro Tyr Leu Met
1               5

<210> SEQ ID NO 74
<211> LENGTH: 5
<212> TYPE: PRT
<213> ORGANISM: Artificial Sequence
<220> FEATURE:
<223> OTHER INFORMATION: Variant sequence at human heregulin-beta1
      residues 205-209

<400> SEQUENCE: 74

Tyr Gly Tyr Leu Met
1               5

<210> SEQ ID NO 75
<211> LENGTH: 5
<212> TYPE: PRT
<213> ORGANISM: Artificial Sequence
<220> FEATURE:
<223> OTHER INFORMATION: Variant sequence at human heregulin-beta1
      residues 205-209

<400> SEQUENCE: 75

Tyr Arg Tyr Arg Met
1               5

<210> SEQ ID NO 76
<211> LENGTH: 5
<212> TYPE: PRT
<213> ORGANISM: Artificial Sequence
<220> FEATURE:
<223> OTHER INFORMATION: Variant sequence at human heregulin-beta1
      residues 205-209

<400> SEQUENCE: 76

Thr His Tyr Arg Gly
1               5

<210> SEQ ID NO 77
```

```
<211> LENGTH: 5
<212> TYPE: PRT
<213> ORGANISM: Artificial Sequence
<220> FEATURE:
<223> OTHER INFORMATION: Variant sequence at human heregulin-beta1
      residues 205-209

<400> SEQUENCE: 77

Thr His Tyr Arg Met
1               5

<210> SEQ ID NO 78
<211> LENGTH: 5
<212> TYPE: PRT
<213> ORGANISM: Artificial Sequence
<220> FEATURE:
<223> OTHER INFORMATION: Variant sequence at human heregulin-beta1
      residues 205-209

<400> SEQUENCE: 78

Tyr Lys Tyr Arg Met
1               5

<210> SEQ ID NO 79
<211> LENGTH: 5
<212> TYPE: PRT
<213> ORGANISM: Artificial Sequence
<220> FEATURE:
<223> OTHER INFORMATION: Variant sequence at human heregulin-beta1
      residues 205-209

<400> SEQUENCE: 79

Thr Lys Tyr Arg Gly
1               5

<210> SEQ ID NO 80
<211> LENGTH: 5
<212> TYPE: PRT
<213> ORGANISM: Artificial Sequence
<220> FEATURE:
<223> OTHER INFORMATION: Variant sequence at human heregulin-beta1
      residues 205-209

<400> SEQUENCE: 80

Tyr Lys Tyr Arg Leu
1               5

<210> SEQ ID NO 81
<211> LENGTH: 6
<212> TYPE: PRT
<213> ORGANISM: Homo sapiens

<400> SEQUENCE: 81

Lys Cys Pro Asn Glu Phe
1               5

<210> SEQ ID NO 82
<211> LENGTH: 6
<212> TYPE: PRT
<213> ORGANISM: Artificial Sequence
<220> FEATURE:
<223> OTHER INFORMATION: Variant sequence at human heregulin-beta1
      residues 211-216

<400> SEQUENCE: 82

Arg Cys Ser Leu Glu Phe
1               5
```

<210> SEQ ID NO 83
<211> LENGTH: 6
<212> TYPE: PRT
<213> ORGANISM: Artificial Sequence
<220> FEATURE:
<223> OTHER INFORMATION: Variant sequence at human heregulin-beta1
      residues 211-216

<400> SEQUENCE: 83

Arg Cys Ser Glu Glu Phe
 1               5

<210> SEQ ID NO 84
<211> LENGTH: 6
<212> TYPE: PRT
<213> ORGANISM: Artificial Sequence
<220> FEATURE:
<223> OTHER INFORMATION: Variant sequence at human heregulin-beta1
      residues 211-216

<400> SEQUENCE: 84

Lys Cys Pro Lys Glu Met
 1               5

<210> SEQ ID NO 85
<211> LENGTH: 6
<212> TYPE: PRT
<213> ORGANISM: Artificial Sequence
<220> FEATURE:
<223> OTHER INFORMATION: Variant sequence at human heregulin-beta1
      residues 211-216

<400> SEQUENCE: 85

Arg Cys Thr Val Glu Tyr
 1               5

<210> SEQ ID NO 86
<211> LENGTH: 6
<212> TYPE: PRT
<213> ORGANISM: Artificial Sequence
<220> FEATURE:
<223> OTHER INFORMATION: Variant sequence at human heregulin-beta1
      residues 211-216

<400> SEQUENCE: 86

Arg Cys Thr Val Glu Tyr
 1               5

<210> SEQ ID NO 87
<211> LENGTH: 6
<212> TYPE: PRT
<213> ORGANISM: Artificial Sequence
<220> FEATURE:
<223> OTHER INFORMATION: Variant sequence at human heregulin-beta1
      residues 211-216

<400> SEQUENCE: 87

Lys Cys Asn Ser Glu Phe
 1               5

<210> SEQ ID NO 88
<211> LENGTH: 6
<212> TYPE: PRT
<213> ORGANISM: Artificial Sequence
<220> FEATURE:
<223> OTHER INFORMATION: Variant sequence at human heregulin-beta1
      residues 211-216

-continued

```
<400> SEQUENCE: 88

Arg Cys Lys Lys Glu Phe
1               5

<210> SEQ ID NO 89
<211> LENGTH: 5
<212> TYPE: PRT
<213> ORGANISM: Homo sapiens

<400> SEQUENCE: 89

Gln Asn Tyr Val Met
1               5

<210> SEQ ID NO 90
<211> LENGTH: 5
<212> TYPE: PRT
<213> ORGANISM: Artificial Sequence
<220> FEATURE:
<223> OTHER INFORMATION: Variant sequence at human heregulin-beta1
      residues 222-226

<400> SEQUENCE: 90

Gln Trp Tyr Val Ile
1               5

<210> SEQ ID NO 91
<211> LENGTH: 5
<212> TYPE: PRT
<213> ORGANISM: Artificial Sequence
<220> FEATURE:
<223> OTHER INFORMATION: Variant sequence at human heregulin-beta1
      residues 222-226

<400> SEQUENCE: 91

Gln His Tyr Val Ile
1               5

<210> SEQ ID NO 92
<211> LENGTH: 52
<212> TYPE: PRT
<213> ORGANISM: Homo sapiens

<400> SEQUENCE: 92

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser
    50

<210> SEQ ID NO 93
<211> LENGTH: 645
<212> TYPE: PRT
<213> ORGANISM: Homo sapiens

<400> SEQUENCE: 93

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Gln Leu Lys Glu Met Lys Ser Gln Glu Ser Ala
```

```
                 35                  40                  45
Ala Gly Ser Lys Leu Val Leu Arg Cys Glu Thr Ser Ser Glu Tyr Ser
             50                  55                  60

Ser Leu Arg Phe Lys Trp Phe Lys Asn Gly Asn Glu Leu Asn Arg Lys
 65                  70                  75                  80

Asn Lys Pro Gln Asn Ile Lys Ile Gln Lys Pro Gly Lys Ser Glu
                 85                  90                  95

Leu Arg Ile Asn Lys Ala Ser Leu Ala Asp Ser Gly Glu Tyr Met Cys
                100                 105                 110

Lys Val Ile Ser Lys Leu Gly Asn Asp Ser Ala Ser Ala Asn Ile Thr
                115                 120                 125

Ile Val Glu Ser Asn Glu Ile Ile Thr Gly Met Pro Ala Ser Thr Glu
                130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
                180                 185                 190

Gly Gly Glu Cys Phe Met Val Lys Asp Leu Ser Asn Pro Ser Arg Tyr
                195                 200                 205

Leu Cys Lys Cys Pro Asn Glu Phe Thr Gly Asp Arg Cys Gln Asn Tyr
                210                 215                 220

Val Met Ala Ser Phe Tyr Lys His Leu Gly Ile Glu Phe Met Glu Ala
225                 230                 235                 240

Glu Glu Leu Tyr Gln Lys Arg Val Leu Thr Ile Thr Gly Ile Cys Ile
                245                 250                 255

Ala Leu Leu Val Val Gly Ile Met Cys Val Val Ala Tyr Cys Lys Thr
                260                 265                 270

Lys Lys Gln Arg Lys Lys Leu His Asp Arg Leu Arg Gln Ser Leu Arg
                275                 280                 285

Ser Glu Arg Asn Asn Met Met Asn Ile Ala Asn Gly Pro His His Pro
                290                 295                 300

Asn Pro Pro Pro Glu Asn Val Gln Leu Val Asn Gln Tyr Val Ser Lys
305                 310                 315                 320

Asn Val Ile Ser Ser Glu His Ile Val Glu Arg Glu Ala Glu Thr Ser
                325                 330                 335

Phe Ser Thr Ser His Tyr Thr Ser Thr Ala His His Ser Thr Thr Val
                340                 345                 350

Thr Gln Thr Pro Ser His Ser Trp Ser Asn Gly His Thr Glu Ser Ile
                355                 360                 365

Leu Ser Glu Ser His Ser Val Ile Val Met Ser Ser Val Glu Asn Ser
                370                 375                 380

Arg His Ser Ser Pro Thr Gly Gly Pro Arg Gly Arg Leu Asn Gly Thr
385                 390                 395                 400

Gly Gly Pro Arg Glu Cys Asn Ser Phe Leu Arg His Ala Arg Glu Thr
                405                 410                 415

Pro Asp Ser Tyr Arg Asp Ser Pro His Ser Glu Arg Tyr Val Ser Ala
                420                 425                 430

Met Thr Thr Pro Ala Arg Met Ser Pro Val Asp Phe His Thr Pro Ser
                435                 440                 445

Ser Pro Lys Ser Pro Pro Ser Glu Met Ser Pro Pro Val Ser Ser Met
                450                 455                 460
```

```
Thr Val Ser Met Pro Ser Met Ala Val Ser Pro Phe Met Glu Glu Glu
465                 470                 475                 480

Arg Pro Leu Leu Val Thr Pro Pro Arg Leu Arg Glu Lys Lys Phe
            485                 490                 495

Asp His His Pro Gln Gln Phe Ser Ser Phe His His Asn Pro Ala His
            500                 505                 510

Asp Ser Asn Ser Leu Pro Ala Ser Pro Leu Arg Ile Val Glu Asp Glu
            515                 520                 525

Glu Tyr Glu Thr Thr Gln Glu Tyr Glu Pro Ala Gln Glu Pro Val Lys
            530                 535                 540

Lys Leu Ala Asn Ser Arg Arg Ala Lys Arg Thr Lys Pro Asn Gly His
545                 550                 555                 560

Ile Ala Asn Arg Leu Glu Val Asp Ser Asn Thr Ser Ser Gln Ser Ser
                565                 570                 575

Asn Ser Glu Ser Glu Thr Glu Asp Glu Arg Val Gly Glu Asp Thr Pro
            580                 585                 590

Phe Leu Gly Ile Gln Asn Pro Leu Ala Ala Ser Leu Glu Ala Thr Pro
            595                 600                 605

Ala Phe Arg Leu Ala Asp Ser Arg Thr Asn Pro Ala Gly Arg Phe Ser
610                 615                 620

Thr Gln Glu Glu Ile Gln Ala Arg Leu Ser Ser Val Ile Ala Asn Gln
625                 630                 635                 640

Asp Pro Ile Ala Val
                645

<210> SEQ ID NO 94
<211> LENGTH: 56
<212> TYPE: PRT
<213> ORGANISM: Homo sapiens

<400> SEQUENCE: 94

Gly Thr Ser His Leu Val Lys Cys Gly Trp Asp Arg Glu Gly Phe Cys
1               5                   10                  15

Val Asn Gly Gly Glu Cys Phe Met Val Lys Asp Leu Ser Asn Pro Ser
            20                  25                  30

Arg Tyr Leu Cys Lys Cys Pro Asn Glu Phe Thr Gly Asp Arg Cys Gln
        35                  40                  45

Asn Tyr Val Ile Ala Ser Phe Tyr
    50                  55

<210> SEQ ID NO 95
<211> LENGTH: 56
<212> TYPE: PRT
<213> ORGANISM: Homo sapiens

<400> SEQUENCE: 95

Gly Thr Ser His Leu Val Lys Cys Asp Lys Ser Arg Glu Gly Phe Cys
1               5                   10                  15

Val Asn Gly Gly Glu Cys Phe Met Val Lys Asp Leu Ser Asn Pro Ser
            20                  25                  30

Arg Tyr Leu Cys Lys Cys Pro Asn Glu Phe Thr Gly Asp Arg Cys Gln
        35                  40                  45

Asn Tyr Val Ile Ala Ser Phe Tyr
    50                  55

<210> SEQ ID NO 96
```

<211> LENGTH: 56
<212> TYPE: PRT
<213> ORGANISM: Homo sapiens

<400> SEQUENCE: 96

Gly Thr Ser His Leu Val Lys Cys Ala Glu Lys Glu Lys Thr Phe Cys
1               5                   10                  15

Val Asn Gly Gly Glu Cys Tyr Lys Val Arg Ile Leu Ser Asn Pro Ser
            20                  25                  30

Arg Tyr Leu Cys Lys Cys Pro Asn Glu Phe Thr Gly Asp Arg Cys Gln
        35                  40                  45

Asn Tyr Val Ile Ala Ser Phe Tyr
    50                  55

<210> SEQ ID NO 97
<211> LENGTH: 56
<212> TYPE: PRT
<213> ORGANISM: Homo sapiens

<400> SEQUENCE: 97

Gly Thr Ser His Leu Val Lys Cys Ala Glu Lys Glu Lys Thr Phe Cys
1               5                   10                  15

Val Asn Gly Gly Glu Cys Phe Met Val Lys Asp Leu Ser Asn Tyr Gly
            20                  25                  30

Tyr Leu Met Cys Lys Cys Pro Asn Glu Phe Thr Gly Asp Arg Cys Gln
        35                  40                  45

Asn Tyr Val Met Ala Ser Phe Tyr
    50                  55

<210> SEQ ID NO 98
<211> LENGTH: 56
<212> TYPE: PRT
<213> ORGANISM: Homo sapiens

<400> SEQUENCE: 98

Gly Thr Ser His Leu Val Lys Cys Ala Glu Lys Glu Lys Thr Phe Cys
1               5                   10                  15

Val Asn Gly Gly Glu Cys Phe Met Val Lys Asp Leu Ser Asn Tyr Arg
            20                  25                  30

Tyr Arg Met Cys Lys Cys Pro Asn Glu Phe Thr Gly Asp Arg Cys Gln
        35                  40                  45

Asn Tyr Val Ile Ala Ser Phe Tyr
    50                  55

<210> SEQ ID NO 99
<211> LENGTH: 56
<212> TYPE: PRT
<213> ORGANISM: Homo sapiens

<400> SEQUENCE: 99

Gly Thr Ser His Leu Val Lys Cys Ala Glu Lys Glu Lys Thr Phe Cys
1               5                   10                  15

Val Asn Gly Gly Glu Cys Phe Met Val Lys Asp Leu Ser Asn Thr His
            20                  25                  30

Tyr Arg Met Cys Lys Cys Pro Asn Glu Phe Thr Gly Asp Arg Cys Gln
        35                  40                  45

Asn Tyr Val Met Ala Ser Phe Tyr
    50                  55

```
<210> SEQ ID NO 100
<211> LENGTH: 56
<212> TYPE: PRT
<213> ORGANISM: Homo sapiens

<400> SEQUENCE: 100

Gly Thr Ser His Leu Val Lys Cys Ala Glu Lys Glu Lys Thr Phe Cys
 1               5                  10                  15

Val Asn Gly Gly Glu Cys Phe Met Val Lys Asp Leu Ser Asn Thr Lys
                20                  25                  30

Tyr Arg Gly Cys Lys Cys Pro Asn Glu Phe Thr Gly Asp Arg Cys Gln
            35                  40                  45

Asn Tyr Val Met Ala Ser Phe Tyr
    50                  55

<210> SEQ ID NO 101
<211> LENGTH: 56
<212> TYPE: PRT
<213> ORGANISM: Homo sapiens

<400> SEQUENCE: 101

Gly Thr Ser His Leu Val Lys Cys Ala Glu Lys Glu Lys Thr Phe Cys
 1               5                  10                  15

Val Asn Gly Gly Glu Cys Phe Met Val Lys Asp Leu Ser Asn Pro Ser
                20                  25                  30

Arg Tyr Leu Cys Lys Cys Pro Asn Glu Phe Thr Gly Asp Arg Cys Gln
            35                  40                  45

Trp Tyr Val Ile Ala Ser Phe Tyr
    50                  55

<210> SEQ ID NO 102
<211> LENGTH: 56
<212> TYPE: PRT
<213> ORGANISM: Homo sapiens

<400> SEQUENCE: 102

Gly Thr Ser His Leu Val Lys Cys Ala Glu Lys Glu Lys Thr Phe Cys
 1               5                  10                  15

Val Asn Gly Gly Glu Cys Phe Met Val Lys Asp Leu Ser Asn Pro Ser
                20                  25                  30

Arg Tyr Leu Cys Lys Cys Pro Asn Glu Phe Thr Gly Asp Arg Cys Gln
            35                  40                  45

His Tyr Val Ile Ala Ser Phe Tyr
    50                  55

<210> SEQ ID NO 103
<211> LENGTH: 56
<212> TYPE: PRT
<213> ORGANISM: Homo sapiens

<400> SEQUENCE: 103

Gly Thr Trp Glu Leu Val Pro Cys Gly Trp Asp Arg Glu Gly Phe Cys
 1               5                  10                  15

Val Asn Gly Gly Glu Cys Phe Met Val Lys Asp Leu Ser Asn Pro Ser
                20                  25                  30

Arg Tyr Leu Cys Lys Cys Pro Asn Glu Phe Thr Gly Asp Arg Cys Gln
            35                  40                  45

Asn Tyr Val Ile Ala Ser Phe Tyr
    50                  55
```

<210> SEQ ID NO 104
<211> LENGTH: 56
<212> TYPE: PRT
<213> ORGANISM: Homo sapiens

<400> SEQUENCE: 104

Gly Thr Ser His Leu Val Lys Cys Ala Glu Lys Glu Lys Thr Phe Cys
1               5                   10                  15

Val Asn Gly Gly Glu Cys Phe Met Val Lys Asp Leu Ser Asn Tyr Gly
            20                  25                  30

Tyr Leu Met Cys Lys Cys Pro Asn Glu Phe Thr Gly Asp Arg Cys Gln
        35                  40                  45

Asn Tyr Val Ile Ala Ser Phe Tyr
    50                  55

<210> SEQ ID NO 105
<211> LENGTH: 56
<212> TYPE: PRT
<213> ORGANISM: Homo sapiens

<400> SEQUENCE: 105

Gly Thr Ser His Leu Val Lys Cys Gly Glu Glu Arg Glu Gly Phe Cys
1               5                   10                  15

Val Asn Gly Gly Glu Cys Tyr Arg Val Lys Thr Leu Ser Asn Pro Ser
            20                  25                  30

Arg Tyr Leu Cys Lys Cys Pro Asn Glu Phe Thr Gly Asp Arg Cys Gln
        35                  40                  45

Asn Tyr Val Met Ala Ser Phe Tyr
    50                  55

<210> SEQ ID NO 106
<211> LENGTH: 56
<212> TYPE: PRT
<213> ORGANISM: Homo sapiens

<400> SEQUENCE: 106

Gly Thr Ser His Leu Val Lys Cys Gly Glu Glu Arg Glu Gly Phe Cys
1               5                   10                  15

Val Asn Gly Gly Glu Cys Phe Met Val Lys Asp Leu Ser Asn Tyr Gly
            20                  25                  30

Tyr Leu Met Cys Lys Cys Pro Asn Glu Phe Thr Gly Asp Arg Cys Gln
        35                  40                  45

Asn Tyr Val Met Ala Ser Phe Tyr
    50                  55

<210> SEQ ID NO 107
<211> LENGTH: 56
<212> TYPE: PRT
<213> ORGANISM: Homo sapiens

<400> SEQUENCE: 107

Gly Thr Ser His Leu Val Lys Cys Gly Glu Glu Arg Glu Gly Phe Cys
1               5                   10                  15

Val Asn Gly Gly Glu Cys Tyr Arg Val Lys Thr Leu Ser Asn Tyr Gly
            20                  25                  30

Tyr Leu Met Cys Lys Cys Pro Asn Glu Phe Thr Gly Asp Arg Cys Gln
        35                  40                  45

Asn Tyr Val Met Ala Ser Phe Tyr
    50                  55

<210> SEQ ID NO 108
<211> LENGTH: 56
<212> TYPE: PRT
<213> ORGANISM: Homo sapiens

<400> SEQUENCE: 108

Gly Thr Ser His Leu Val Lys Cys Gly Glu Glu Arg Glu Gly Phe Cys
1               5                   10                  15

Val Asn Gly Gly Glu Cys Phe Met Val Lys Asp Leu Ser Asn Pro Ser
            20                  25                  30

Arg Tyr Leu Cys Lys Cys Pro Asn Glu Phe Thr Gly Asp Arg Cys Gln
        35                  40                  45

Asn Tyr Val Ile Ala Ser Phe Tyr
    50                  55

<210> SEQ ID NO 109
<211> LENGTH: 56
<212> TYPE: PRT
<213> ORGANISM: Homo sapiens

<400> SEQUENCE: 109

Gly Thr Ser His Leu Val Lys Cys Ala Glu Lys Glu Lys Thr Phe Cys
1               5                   10                  15

Val Asn Gly Gly Glu Cys Tyr Arg Val Lys Thr Leu Ser Asn Tyr Gly
            20                  25                  30

Tyr Leu Met Cys Lys Cys Pro Asn Glu Phe Thr Gly Asp Arg Cys Gln
        35                  40                  45

Asn Tyr Val Met Ala Ser Phe Tyr
    50                  55

<210> SEQ ID NO 110
<211> LENGTH: 56
<212> TYPE: PRT
<213> ORGANISM: Homo sapiens

<400> SEQUENCE: 110

Gly Thr Ser His Leu Val Lys Cys Ala Glu Lys Glu Lys Thr Phe Cys
1               5                   10                  15

Val Asn Gly Gly Glu Cys Tyr Arg Val Lys Thr Leu Ser Asn Tyr Gly
            20                  25                  30

Tyr Leu Met Cys Lys Cys Pro Asn Glu Phe Thr Gly Asp Arg Cys Gln
        35                  40                  45

Asn Tyr Val Ile Ala Ser Phe Tyr
    50                  55

<210> SEQ ID NO 111
<211> LENGTH: 56
<212> TYPE: PRT
<213> ORGANISM: Homo sapiens

<400> SEQUENCE: 111

Gly Thr Ser His Leu Val Lys Cys Ala Glu Lys Glu Lys Thr Phe Cys
1               5                   10                  15

Val Asn Gly Gly Glu Cys Tyr Arg Val Lys Thr Leu Ser Asn Pro Ser
            20                  25                  30

Arg Tyr Leu Cys Lys Cys Pro Asn Glu Phe Thr Gly Asp Arg Cys Gln
        35                  40                  45

Asn Tyr Val Ile Ala Ser Phe Tyr

```
        50                  55

<210> SEQ ID NO 112
<211> LENGTH: 56
<212> TYPE: PRT
<213> ORGANISM: Homo sapiens

<400> SEQUENCE: 112

Gly Thr Ser His Leu Val Lys Cys Gly Glu Glu Arg Glu Gly Phe Cys
1               5                   10                  15

Val Asn Gly Gly Glu Cys Tyr Arg Val Lys Thr Leu Ser Asn Pro Ser
            20                  25                  30

Arg Tyr Leu Cys Lys Cys Pro Asn Glu Phe Thr Gly Asp Arg Cys Gln
        35                  40                  45

Asn Tyr Val Ile Ala Ser Phe Tyr
    50                  55

<210> SEQ ID NO 113
<211> LENGTH: 56
<212> TYPE: PRT
<213> ORGANISM: Homo sapiens

<400> SEQUENCE: 113

Gly Thr Ser His Leu Val Lys Cys Gly Glu Glu Arg Glu Gly Phe Cys
1               5                   10                  15

Val Asn Gly Gly Glu Cys Phe Met Val Lys Asp Leu Ser Asn Tyr Gly
            20                  25                  30

Tyr Leu Met Cys Lys Cys Pro Asn Glu Phe Thr Gly Asp Arg Cys Gln
        35                  40                  45

Asn Tyr Val Ile Ala Ser Phe Tyr
    50                  55

<210> SEQ ID NO 114
<211> LENGTH: 56
<212> TYPE: PRT
<213> ORGANISM: Homo sapiens

<400> SEQUENCE: 114

Gly Thr Ser His Leu Val Lys Cys Gly Glu Glu Arg Glu Gly Phe Cys
1               5                   10                  15

Val Asn Gly Gly Glu Cys Tyr Arg Val Lys Thr Leu Ser Asn Tyr Gly
            20                  25                  30

Tyr Leu Met Cys Lys Cys Pro Asn Glu Phe Thr Gly Asp Arg Cys Gln
        35                  40                  45

Asn Tyr Val Ile Ala Ser Phe Tyr
    50                  55

<210> SEQ ID NO 115
<211> LENGTH: 56
<212> TYPE: PRT
<213> ORGANISM: Homo sapiens

<400> SEQUENCE: 115

Gly Thr Ser His Leu Val Lys Cys Ala Glu Lys Glu Lys Thr Phe Cys
1               5                   10                  15

Val Asn Gly Gly Glu Cys Tyr Arg Val Lys Thr Leu Ser Asn Tyr Gly
            20                  25                  30

Tyr Leu Met Cys Lys Cys Pro Asn Glu Phe Thr Gly Asp Arg Cys Gln
        35                  40                  45
```

```
-continued

His Tyr Val Ile Ala Ser Phe Tyr
    50              55

<210> SEQ ID NO 116
<211> LENGTH: 56
<212> TYPE: PRT
<213> ORGANISM: Homo sapiens

<400> SEQUENCE: 116

Gly Thr Ser His Leu Val Lys Cys Gly Glu Glu Arg Glu Gly Phe Cys
 1               5                  10                  15

Val Asn Gly Gly Glu Cys Tyr Arg Val Lys Thr Leu Ser Asn Tyr Gly
            20                  25                  30

Tyr Leu Met Cys Lys Cys Pro Asn Glu Phe Thr Gly Asp Arg Cys Gln
         35                  40                  45

His Tyr Val Ile Ala Ser Phe Tyr
    50              55
```